US006833367B2

(12) United States Patent
Kinder, Jr. et al.

(10) Patent No.: US 6,833,367 B2
(45) Date of Patent: Dec. 21, 2004

(54) CERTAIN SUBSTITUTED POLYKETIDES, PHARMACEUTICAL COMPOSITIONS CONTAINING THEM AND THEIR USE IN TREATING TUMORS

(75) Inventors: Frederick R. Kinder, Jr., Morristown, NJ (US); Kenneth W. Bair, Mountain Lakes, NJ (US); Timothy M. Ramsey, Sparta, NJ (US); Michael L. Sabio, Randolph, NJ (US)

(73) Assignee: Novartis AC, Basel (CH)

( * ) Notice: Subject to any disclaimer, the term of this patent is extended or adjusted under 35 U.S.C. 154(b) by 71 days.

(21) Appl. No.: 10/292,134

(22) Filed: Nov. 12, 2002

(65) Prior Publication Data

US 2003/0153601 A1 Aug. 14, 2003

Related U.S. Application Data

(60) Provisional application No. 60/343,394, filed on Dec. 21, 2001, and provisional application No. 60/332,399, filed on Nov. 16, 2001.

(51) Int. Cl.[7] .................... A61K 31/366; A61P 35/00; C07D 309/30
(52) U.S. Cl. .................... 514/231.5; 514/336; 514/365; 514/374; 514/378; 514/397; 514/444; 544/149; 546/282.1; 548/204; 548/236; 548/247; 548/311.1
(58) Field of Search .................... 544/149; 546/282.1; 548/204, 236, 247, 311.1; 549/60, 292; 514/231.5, 336, 365, 374, 378, 397, 444

(56) References Cited

U.S. PATENT DOCUMENTS

| 6,096,904 A | 8/2000 | Smith, III et al. |
| 6,127,406 A | 10/2000 | Gunasekera et al. |
| 6,242,616 B1 * | 6/2001 | Smith et al. ................. 549/292 |

FOREIGN PATENT DOCUMENTS

| WO | WO 98/24429 | 6/1998 |
| WO | WO 00/04865 | 2/2000 |
| WO | WO 01 42179 A | 6/2001 |
| WO | WO 02/46150 A2 | 6/2002 |

OTHER PUBLICATIONS

Gunasekera S.P. et al., "Five New Discodermolide Analogues from the Marine Sponge Discodermia Species", Journal of Natural Products, pp. A–F, (2002).
Smith A.B. et al., "Gram–Scale Synthesis of (+)–Discodermolide", Organic Letters, vol. 1, No. 11, pp. 1823–1826 (1999).
Martello, L.A. et al., "The relationship between Taxol and (+)–discodermolide: synthetic analogs and modelling studies", Chemistry & Biology, vol. 8/9, pp. 843–855 (2001).
Marshall J.A. et al., "Total Synthesis of (+)–Discodermolide", J.Org.Chem., vol. 63, No. 22, pp. 7885–7892 (1998).
Harried S.S. et al., "Total Synthesis of (−)–Discodermolide: An Application of a Chelation–Controlled Alkylation Reaction", J.Org.Chem., vol. 62, No. 18, pp. 6098–6099 (1997).
Smith A.B. et al., "Total Synthesis of (−)–Discodermolide", J.Am.Chem.Soc., vol. 117, No. 48, pp. 12011–12012 (1995).
Nerenberg J.B. et al., "Total Synthesis of the Immunosuppressive Agent (−)–Discodermolide", J.Am.Chem.Soc., vol. 115, No. 126, pp. 12621–12622 (1993).
Hung D.T. et al., "Syntheses of Discodermolides Useful for Investigating Microtubule Binding and Stabilization", J.Am.Chem.Soc., vol. 118, No. 45, pp. 11054–11080 (1996).
Paterson I. et al., "Total Synthesis of the Antimocrotubule Agent . . . Aldol Reactions of Chiral Ketones", Angew.Chem.Int.End., vol. 39, No. 2, pp. 377–380 (2000).
Curran D.P. et al., "Simultaneous Preparation of Four Truncated Analogues . . . Fluorous Mixture Synthesis", Organic Letters, vol. 4, No. 13, pp. 2233–2235 (2002).
Abstract, 01694771, Halstead, David Patrick, vol. 60/03–B of Dissertation Abstracts International, p. 1087.
Gunasekera S.P. et al., "Semisynthetic Analogues of the Microtubule–Stabilizing Agent Discodermolide: Preparation and Biological Activity", J.Nat.Prod., vol. 65, pp. 1830–1837 (2002).
Youseung S. et al., "Discodermolide/Dictyostatin Hybrids: Synthesis and Biological Evaluation", Organic Letters, pp. A–D, (2002).
Hung D. T. et al., "Syntheses of Discodermolides Useful for Investigating Microtubule Binding and Stabilization", Journal of the Americal Chemical Society, vol. 118, No. 45, pp. 11054–11080, (1996) XP 000652059 *.

* cited by examiner

Primary Examiner—Fiona T. Powers
(74) Attorney, Agent, or Firm—Lydia T. McNally; Joseph J. Borovian

(57) ABSTRACT

The present invention relates to certain substituted polyketides of formula I,

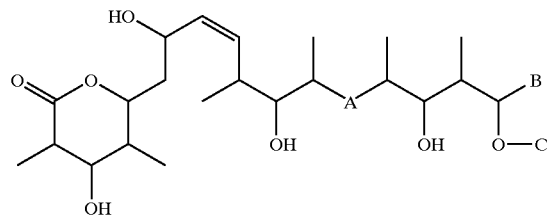

wherein A, B and C are as defined herein, pharmaceutical compositions containing said compounds, and the use of said compounds in treating tumors.

16 Claims, No Drawings

CERTAIN SUBSTITUTED POLYKETIDES, PHARMACEUTICAL COMPOSITIONS CONTAINING THEM AND THEIR USE IN TREATING TUMORS

This application claims the benefit of Provisional Application No. 60/343,394, filed Dec. 21, 2001, and Provisional Application No. 60/332,399, filed Nov. 16, 2001, both of the contents of which are incorporated herein by reference.

FIELD OF THE INVENTION

The present invention relates to the area of chemotherapeutic agents and, more particularly, relates to certain substituted polyketides, and the use of said polyketides in treating tumors.

BACKGROUND OF THE INVENTION

Cancer is a serious health problem throughout the world. For example, cancer incidence in the U.S. has increased 30% during the past 30 years, and is expected to continue to increase into the next century. This is attributable to the increased prevalence of cigarette smoking in women compared to men, general aging of the population, and enhanced diagnostic capabilities, as well as potential decreases in mortality from other causes. As a result, an extensive number of research endeavors has been undertaken in an effort to develop therapies appropriate to the treatment and alleviation of cancer in humans.

In the chemotherapeutic area, research has been conducted to develop anti-tumor agents effective against various types of cancer. Oftentimes, anti-tumor agents which have been developed and found effective against cancer cells are, unfortunately, also toxic to normal cells. This toxicity manifests itself in weight loss, nausea, vomiting, hair loss, fatigue, itching, hallucinations, loss of appetite, etc., upon administration of the anti-tumor agent to a patient in need of cancer chemotherapy.

Furthermore, conventionally used chemotherapeutic agents do not have the effectiveness desired or are not as broadly effective against different types of cancers as desired. As a result, a great need exists for chemotherapeutic agents which are not only more effective against all types of cancer, but which have a higher degree of selectivity for killing cancer cells with no or minimal effect on normal healthy cells. In addition, highly effective and selective anti-tumor agents, in particular, against cancers of the colon, bladder, prostate, stomach, pancreas, breast, lung, liver, brain, testis, ovary, cervix, skin, vulva and small intestine are desired. Moreover, anti-tumor activity against colon, breast, lung and prostate cancers as well as melanomas are particularly desired because of the lack of any particular effective therapy at the present time.

(+)-Discodermolide is a novel polyketide natural product that was isolated from extracts of the marine sponge *Discodermia dissoluta* by researchers at the Harbor Branch Oceanographic Institution (HBOI) (Gunasekera S P, Gunasekera M, Longley R E, Schulte G K. Discodermolide: a new bioactive polyhydroxylated lactone from the marine sponge *Discodermia dissoluta*. [published erratum appears in J. Org. Chem. 1991;56:1346]. J. Org. Chem. 1990;55:4912–15.). Discodermolide lacks obvious structural resemblance to paclitaxel, yet it shares with paclitaxel (the active substance in the drug Taxol) the ability to stabilize microtubules. In mechanism-based assays, discodermolide is more effective than paclitaxel. In fact, of the handful of compounds known to induce polymerization of purified tubulin, discodermolide is the most potent. However, microtubules, the major structural component in cells, are not simple equilibrium polymers of tubulin. They exist as regulated GTP-driven dynamic assemblies of heterodimers of $\alpha$ and $\beta$ tubulin. Although the dynamics are relatively slow in interphase cells, upon entering mitosis, the rate of growing and shortening increases 20- to 100-fold— the average microtubule turns over half the tubulin subunits every ten seconds. This change in rate allows the cytoskeletal microtubule network to dismantle and a bipolar spindle-shaped array of microtubules to assemble. The spindle attaches to chromosomes and moves them apart. The response to complete suppression of microtubule dynamics in cells is death. However, mitotic cells are more sensitive and the tolerance threshold appears to be cell-type specific. Molecules like paclitaxel that bind with high affinity to microtubules disrupt the dynamics process in tumor cells with lethal results even when the ratio of bound drug to tubulin is very low. Discodermolide binds to tubulin competitively with paclitaxel. Since paclitaxel has proven to be useful in treating some cancers, other compounds of the same mechanistic class may have utility against hyperproliferative disorders.

Development of discodermolide or structurally related analogues is hindered by the lack of a reliable natural source of the compound or a feasible synthetic route. Naturally occurring discodermolide is scarce and harvesting the producing organism presents logistical problems. There is an ever-growing need for improved syntheses that enable production of multi-gram amounts of discodermolide and structurally related analogues.

DESCRIPTION OF THE PRIOR ART

Martello L A, LaMarche M J, He L, Beauchamp T J, Smith A B, Horwitz S B. The relationship between Taxol and (+)-discodermolide: synthetic analogs and modeling studies. Chem. Biol. 2001;8(9):843–855.

Nerenberg J B, Hung D T, Somers P K, Schreiber S L. Total synthesis of the immunosuppressive agent (−)-discodermolide. J. Am. Chem. Soc. 1993;115:12621–622.

Hung D T, Nerenberg J B, Schreiber S L. Syntheses of discodermolides useful for investigating microtubule binding and stabilization. J. Am. Chem. Soc. 1996;118:11054–11080.

Smith A B, Qiu Y, Jones D R, Kobayashi K. Total synthesis of (−)-discodermolide. J. Am. Chem. Soc. 1995; 117:12011–12012.

Harried S S, Yang G, Strawn M A, Myles D C. Total synthesis of (−)-discodermolide: an application of a chelation-controlled alkylation reaction., J. Org. Chem. 1997;62:6098–6099.

Marshall J A, Johns B A. Total synthesis of (+)-discodermolide. J. Org. Chem. 1998;63:7885–7892.

Halstead D P. I. Total synthesis of (+)-miyakolide II. Total synthesis of (−)-discodermolide III. Total synthesis of (+)-discodermolide (dissertation). Cambridge (Mass): Harvard University, 1998.

Smith A B III, Kaufman M D, Beauchamp T J, LaMarche M J, Arimoto H. Gram-Scale Synthesis of (+)-Discodermolide. Org. Lett. 1999;1:1823–1826.

Paterson I, Florence G J, Gerlach K, Scott J. Total synthesis of the antimicrotubule agent (+)-discodermolide using boron-mediated aldol reactions of chiral ketones. Angew. Chem., Int. Ed. 2000;39:377–380.

Smith A B III, Qiu Y, Kaufman M, Arimoto H, Jones D R, Kobayashi K, Beauchamp T J. Preparation of intermediates for the synthesis of discodermolides and their polyhydroxy dienyl lactone derivatives for pharmaceutical use. U.S. (2000), 83 pp., Cont.-in-part of U.S. Pat. No. 5,789,605. CODEN: USXXAM U.S. Pat. No. 6,096,904 A 20000801 CAN 133:135166 AN 2000:531688.

Smith A B III, Qiu Y, Kaufman M, Arimoto H, Jones D R, Kobayashi K, Beauchamp, T J. Preparation of intermediates for the synthesis of discodermolides and their polyhydroxy dienyl lactone derivatives for pharmaceutical use. PCT Int. Appl. (2000), 201 pp. CODEN: PIXXD2 WO 0004865 A2 20000203 CAN 132:137207 AN 2000:84572.

Smith A B III Qiu Y, Kaufman M, Arimoto H, Jones D R, Kobayashi K. Synthetic techniques and intermediates for polyhydroxydienyllactones and mimics thereof. PCT Int. Appl. (1998), 194 pp. CODEN: PIXXD2 WO 9824429 A1 19980611 CAN 129:67649 AN 1998:394202.

Gunasekera S P, Longley R E. Synthesis, antitumor activity and formulations of discodermolide acetates. U.S. (2000), 9 pp. CODEN: USXXAM U.S. Pat. No. 6,127,406 A 20001003 CAN 133:281651 AN 2000:699192.

SUMMARY OF THE INVENTION

The present invention provides new anti-tumor agents which are effective against a variety of cancer cells. More particularly, the present invention relates to certain substituted polyketides which exhibit a higher degree of selectivity in killing cancer cells. In addition, the present invention provides pharmaceutical compositions useful in treating tumors comprising a therapeutically effective amount of a certain substituted polyketide. Moreover, the present invention provides a method of treating tumors comprising administering to a mammal afflicted therewith a therapeutically effective amount of a certain substituted polyketide.

DETAILED DESCRIPTION OF THE INVENTION

The essence of the instant invention is the discovery that certain substituted polyketides are useful in treating tumors. In one embodiment, the instant invention provides new anti-tumor agents of formula I:

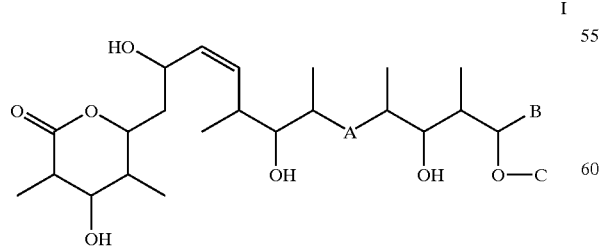

where A is —CH=C($R_1$)$CH_2$—, —$CH_2$N($R_2$)C(O)—, —C(O)N($R_2$)$CH_2$—, —$CH_2$N($R_2$)$CH_2$—, —$CH_2$N($CO_2R_3$)$CH_2$— or —$CH_2$N($COR_2$)$CH_2$—;

B is —CH($R_1$)CH=CHCH=$CH_2$, —CH($R_2$)$R_1$, —CH($R_1$)CH=CH$R_2$, —CH($R_1$)CH=CHC(O)$OR_2$, —CH($R_1$)CH=CHC(O)N($R_1$)$R_2$, —CH($R_1$)$CH_2OR_2$ or Ar;

C is H, —C(O)N($R_1$)$R_2$, —C(O)NHCH$_2$(CH$_2$)$_n$N(CH$_3$)$_2$ or —C(O)NHCH$_2$(CH$_2$)$_n$-4-morpholino;

$R_1$ is H or ($C_{1-6}$)alkyl;

$R_2$ is H, ($C_{1-6}$)alkyl, ($C_{2-6}$)alkenyl, ($C_{2-6}$)alkynyl, ($C_{1-6}$)alkyl-Ar or Ar;

$R_3$ is ($C_{1-6}$)alkyl, ($C_{1-6}$)alkyl-Ar or Ar;

Ar is an aromatic or heteroaromatic ring selected from

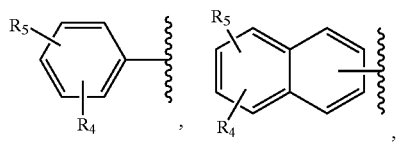

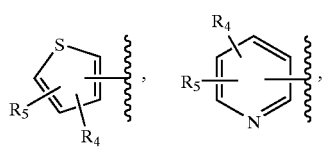

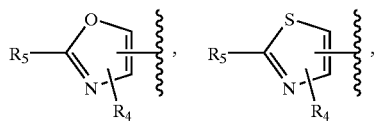

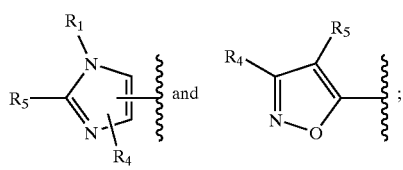

$R_4$ and $R_5$ are, independently, H, ($C_{1-6}$)alkyl, OH, O($C_{1-6}$)alkyl, $OCH_2$($CH_2$)$_n$OH, O($CH_2$)$_n$$CO_2$H, $OCH_2$($CH_2$)$_n$N(CH$_3$)$_2$, $OCH_2$($CH_2$)$_n$-4-morpholino, F, Cl, Br or $CF_3$; and n is 1 or 2;

with the proviso that when A is —CH=C(CH$_3$)$CH_2$— or —CH=CHCH$_2$—, then either:

B cannot be —CH(CH$_3$)CH=CHCH=$CH_2$, —CH(CH$_3$)$CH_2$Ph, —CH(CH$_3$)Ph, —CH(CH$_3$)-n-Bu,

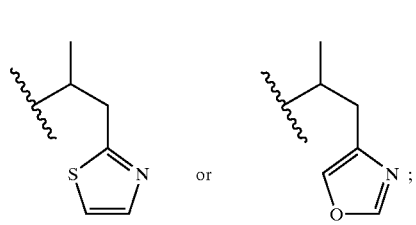

or C cannot be —C(O)N($R_1$)$R_2$ or H;

or an acid or base addition salt thereof, where possible.

Preferred compounds are those of formula Ia:

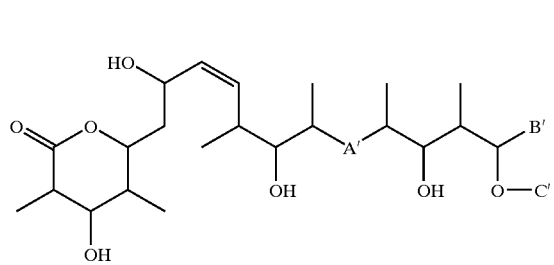

where A' is —CH=C(R$_1$')CH$_2$—, —CH$_2$N(R$_2$')C(O)—, —C(O)N(R$_2$')CH$_2$—, —CH$_2$N(CO$_2$R$_3$')CH$_2$— or —CH$_2$N(COR$_2$')CH$_2$—;
B' is —CH(R$_1$')CH=CHCH=CH$_2$, —CH(R$_2$')R$_1$', —CH(R$_1$')CH=CHR$_2$', —CH(R$_1$')CH$_2$OR$_2$' or Ar';
C' is H, —C(O)N(R$_1$')R$_2$', —C(O)NHCH$_2$(CH$_2$)$_n$N(CH$_3$)$_2$ or —C(O)NHCH$_2$(CH$_2$)$_n$-4-morpholino;
R$_1$' is H or (C$_{1-6}$)alkyl;
R$_2$' is H, (C$_{1-6}$)alkyl, (C$_{2-6}$)alkenyl, (C$_{2-6}$)alkynyl, (C$_{1-6}$)alkyl-Ar' or Ar';
R$_3$' is (C$_{1-6}$)alkyl, (C$_{1-6}$)alkyl-Ar' or Ar';
Ar' is an aromatic or heteroaromatic ring selected from

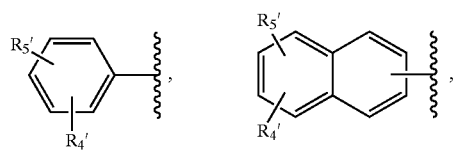

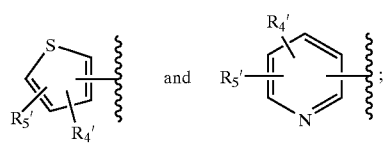

R$_4$' and R$_5$' are,
independently, H, (C$_{1-6}$)alkyl, OH, O(C$_{1-6}$)alkyl, OCH$_2$(CH$_2$)$_n$OH, O(CH$_2$)$_n$CO$_2$H, OCH$_2$(CH$_2$)$_n$N(CH$_3$)$_2$, OCH$_2$(CH$_2$)$_n$-4-morpholino, F, Cl, Br or CF$_3$; and
n is 1 or 2;
with the proviso that when A' is —CH=C(CH$_3$)CH$_2$— or —CH=CHCH$_2$—,
then either:
B' cannot be —CH(CH$_3$)CH=CHCH=CH$_2$, —CH(CH$_3$)CH$_2$Ph, —CH(CH$_3$)Ph, —CH(CH$_3$)-n-Bu,

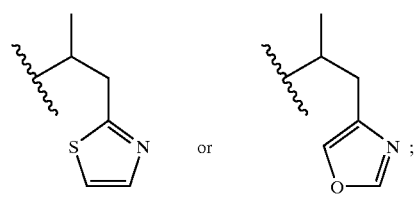

or C' cannot be —C(O)N(R$_1$')R$_2$' or H;
or an acid or base addition salt thereof, where possible.

More preferred compounds are those of formula Ib:

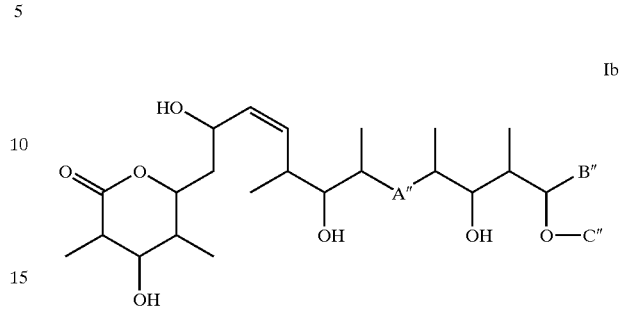

where A" is —CH=C(R$_1$")CH$_2$—, —CH$_2$N(R$_2$")C(O)— or —C(O)N(R$_2$")CH$_2$—;
B" is —CH(R$_1$")CH=CHCH=CH$_2$, —CH(R$_2$")R$_1$", —CH(R$_1$")CH=CHR$_2$", —CH(R$_1$")CH$_2$OR$_2$" or Ar";
C" is H, —C(O)N(R$_1$")R$_2$", —C(O)NHCH$_2$(CH$_2$)$_n$N(CH$_3$)$_2$ or —C(O)NHCH$_2$(CH$_2$)$_n$-4-morpholino;
R$_1$" is H or —CH$_3$;
R$_2$" is H, (C$_{1-6}$)alkyl, (C$_{2-6}$)alkenyl, (C$_{2-6}$)alkynyl, (C$_{1-6}$)alkyl-Ar" or Ar";
Ar" is an aromatic or heteroaromatic ring selected from

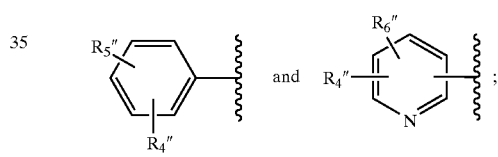

R$_4$" and R$_5$" are,
independently, H, (C$_{1-6}$)alkyl, OH, O(C$_{1-6}$)alkyl, OCH$_2$(CH$_2$)$_n$OH, O(CH$_2$)$_n$, CO$_2$H, OCH$_2$(CH$_2$), N(CH$_3$)$_2$, OCH$_2$(CH$_2$)$_n$-4-morpholino, F, Cl, Br or CF$_3$; and
n is 1 or 2;
with the proviso that when A" is —CH=C(CH$_3$)CH$_2$— or —CH=CHCH$_2$—,
then either:
B" cannot be —CH(CH$_3$)CH=CHCH=CH$_2$, —CH(CH$_3$)CH$_2$Ph, —CH(CH$_3$)Ph, —CH(CH$_3$)-n-Bu,

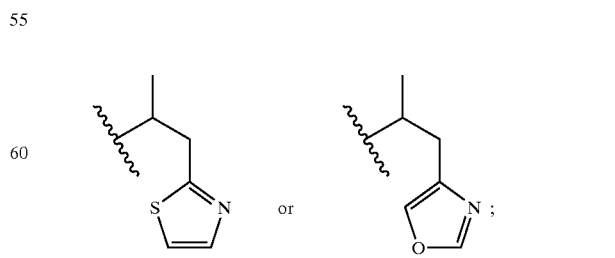

or C" cannot be —C(O)N(R$_1$")R$_2$" or H;
or an acid or base addition salt thereof, where possible.

Even more preferred compounds are those of formula Ic:

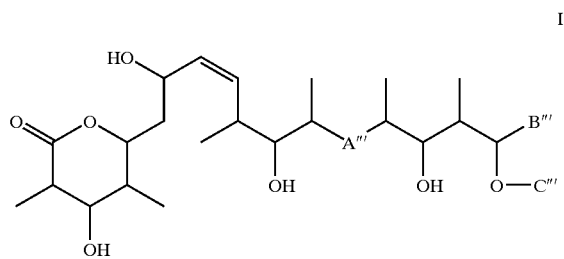

where A''' is —CH=C(R$_1$''')CH$_2$—, —CH$_2$N(R$_2$''')C(O)— or —C(O)N(R$_2$''')CH$_2$—;
B''' is —CH(R$_1$''')CH=CHCH=CH$_2$, —CH(R$_2$''')R$_1$''', —CH(R$_1$''')CH=CHR$_2$''', —CH(R$_1$''')CH$_2$OR$_2$''' or Ar''';
C''' is H or —C(O)N(R$_1$''')R$_2$''';
R$_1$''' is H or CH$_3$;
R$_2$''' is H, (C$_{1-6}$)alkyl, (C$_{2-6}$)alkenyl, (C$_{2-6}$)alkynyl, (C$_{1-6}$)alkyl-Ar''' or Ar''';
Ar''' is an aromatic ring having the formula

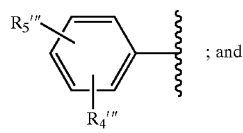 ; and

R$_4$''' and R$_5$''' are, independently, H, (C$_{1-6}$)alkyl, OH, O(C$_{1-6}$)alkyl, F, Cl, Br or CF$_3$;
with the proviso that when A''' is —CH=C(CH$_3$)CH$_2$— or —CH=CHCH$_2$—,
then either:
B''' cannot be —CH(CH$_3$)CH=CHCH=CH$_2$, —CH(CH$_3$)CH$_2$Ph, —CH(CH$_3$)Ph, —CH(CH$_3$)-n-Bu,

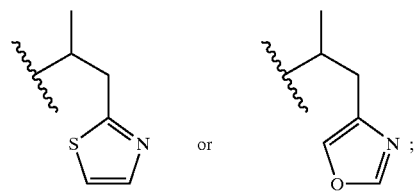

or C''' cannot be —C(O)N(R$_1$''')R$_2$''' or H;
or an acid or base addition salt thereof, where possible.

In another embodiment, the instant invention provides pharmaceutical compositions useful in treating tumors comprising a pharmaceutically acceptable carrier or diluent and a therapeutically effective amount of a compound of formula I above, or a pharmaceutically acceptable acid or base addition salt thereof, where possible, preferably a compound of formula Ia above, or a pharmaceutically acceptable acid or base salt thereof, where possible, more preferably a compound of formula Ib above, or a pharmaceutically acceptable acid or base salt thereof, where possible, and even more preferably a compound of formula Ic above, or a pharmaceutically acceptable acid or base addition salt thereof, where possible.

In still another embodiment, the instant invention provides a method for treating tumors comprising administering to a mammal in need of such treatment a therapeutically effective amount of a compound of formula I above, or a pharmaceutically acceptable acid or base addition salt thereof, where possible, preferably a compound of formula Ia above, or a pharmaceutically acceptable acid or base addition salt thereof, where possible, more preferably a compound of formula Ib above, or a pharmaceutically acceptable acid or base addition salt thereof, where possible, and even more preferably a compound of formula Ic above, or a pharmaceutically acceptable acid or base addition salt thereof, where possible.

In the above definitions: 1) the alkyl groups containing 1 to 6 carbon atoms are either straight or branched chain or cycloalkane, of which examples include isopropyl, isobutyl, t-butyl, isopentyl, neopentyl, isohexyl, 3-methylpentyl, 2,2-dimethylbutyl, 2,3-dimethylbutyl, 1,1,2,2-tetramethylethyl, cyclopentyl and cyclohexyl.

Although the pharmaceutically acceptable acid or base addition salts are preferred, it should be understood that all of the acid or base addition salts of the compounds of formula I are intended to be included within the scope of the present invention.

The acid addition salts of the compounds of formula I may be those of pharmaceutically acceptable organic or inorganic acids. Although the preferred acid addition salts are those of hydrochloric and methanesulfonic acid, salts of sulfuric, phosphoric, citric, fumaric, maleic, benzoic, benzenesulfonic, succinic, tartaric, lactic and acetic acid may also be utilized.

Likewise, the base addition salts of the compounds of formula I may be those of pharmaceutically acceptable organic or inorganic bases. Preferred base addition salts are those derived from pharmaceutically acceptable inorganic bases, more preferably ammonium hydroxide or an alkali or alkaline earth metal hydroxide, e.g, lithium hydroxide, sodium hydroxide, potassium hydroxide, calcium hydroxide, magnesium hydroxide and manganese hydroxide.

The substituted polyketides of formula I may be prepared as depicted below. In the event that the groups A-F contain free hydroxy groups, then the asterisk designation (e.g., A*) indicates that those groups are protected with acid labile protecting groups (e.g., TBS). All acid labile protecting groups covered by the asterisk are removed in the final step (HCl).

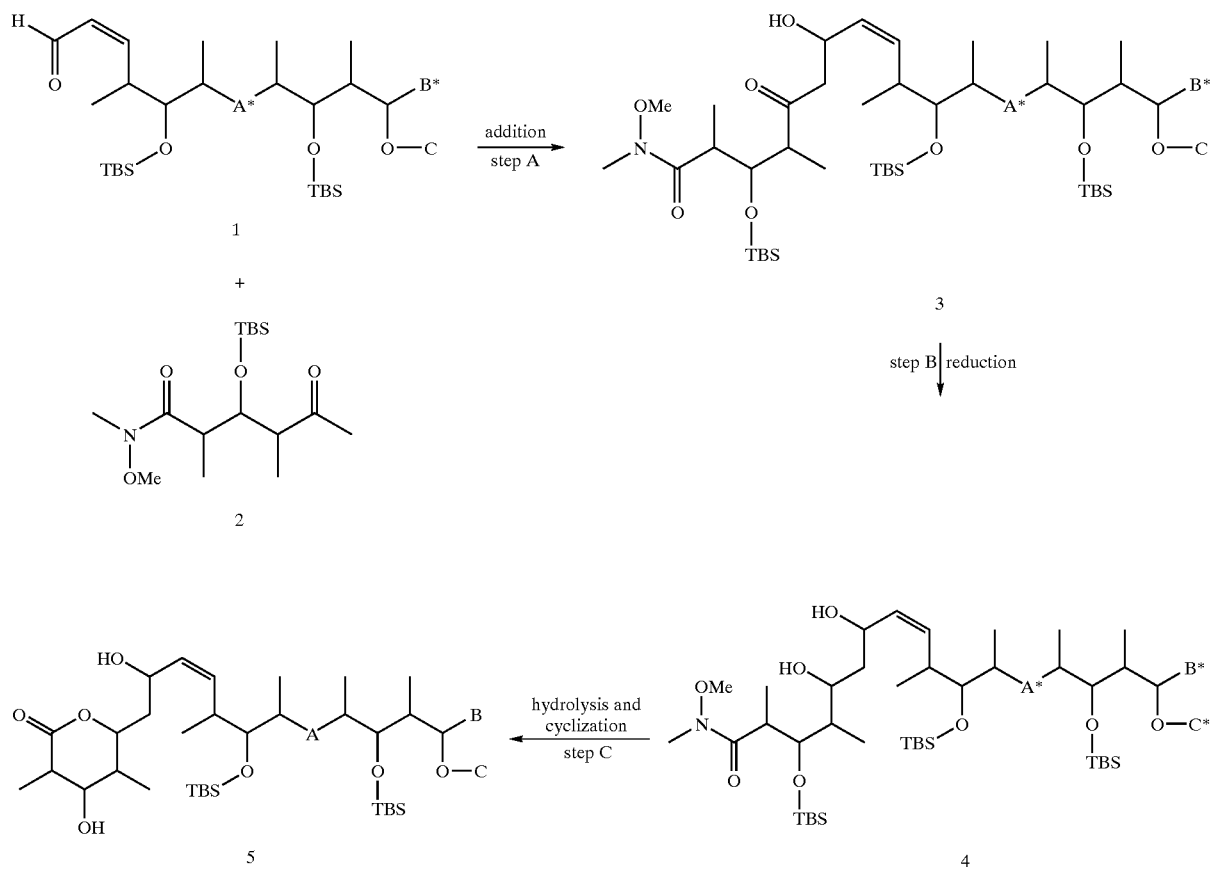

Scheme 1

As to the individual steps in Scheme 1, Step A involves the addition of a ketone of formula 2 to an aldehyde of formula 1 to obtain a hydroxyketone of formula 3. The addition requires between 1 and 20 equivalents of 2 relative to aldehyde 1, preferably between 5 and 15 equivalents of 2 relative to aldehyde 1. The coupling is conducted in the presence of: 1) a dialkylboron halide or triflate, preferably a chiral boron chloride or triflate, more preferably B-chlorodiisopinocampheylborane; 2) a base, preferably an amine, more preferably triethylamine; and 3) a polar organic solvent, preferably an ether, more preferably diethyl ether, at a temperature of between −100° C. and 20° C., preferably between −78° C. and −20° C., for a period of between 2 and 72 hours, preferably for 16 hours.

Step B concerns the reduction of the hydroxyketone of formula 3, to obtain a 1,3-diol compound of formula 4. The reduction is conducted in the presence of: 1) a ketone reducing agent, preferably a borohydride such as tetramethylammonium triacetoxyborohydride; 2) a polar organic solvent, preferably acetonitrile; and 3) a protic solvent, preferably a carboxylic acid, such as acetic acid, at a temperature of between −78° C. and 20° C., preferably between −40° C. and −10° C., for a period of between 2 and 72 hours, preferably for 16 hours.

Step C concerns the hydrolysis and cyclization of the 1,3-diol compound 4 to a substituted polyketide of formula 5. The hydrolysis reaction is conducted in the presence of: 1) a protic acid, preferably an aqueous protic acid solution, preferably an aqueous hydrogen halide solution, such as aqueous hydrogen chloride; and 2) a polar organic solvent, preferably a mixture of polar organic solvents, preferably a mixture of an aliphatic alcohol and an ether, such as methanol and tetrahydrofuran, at a temperature of between −20° C. and 40° C., preferably between 20° C. and 25° C., for a period of 8 hours and 7 days, preferably between 16 and 72 hours, more preferably between 24 and 48 hours.

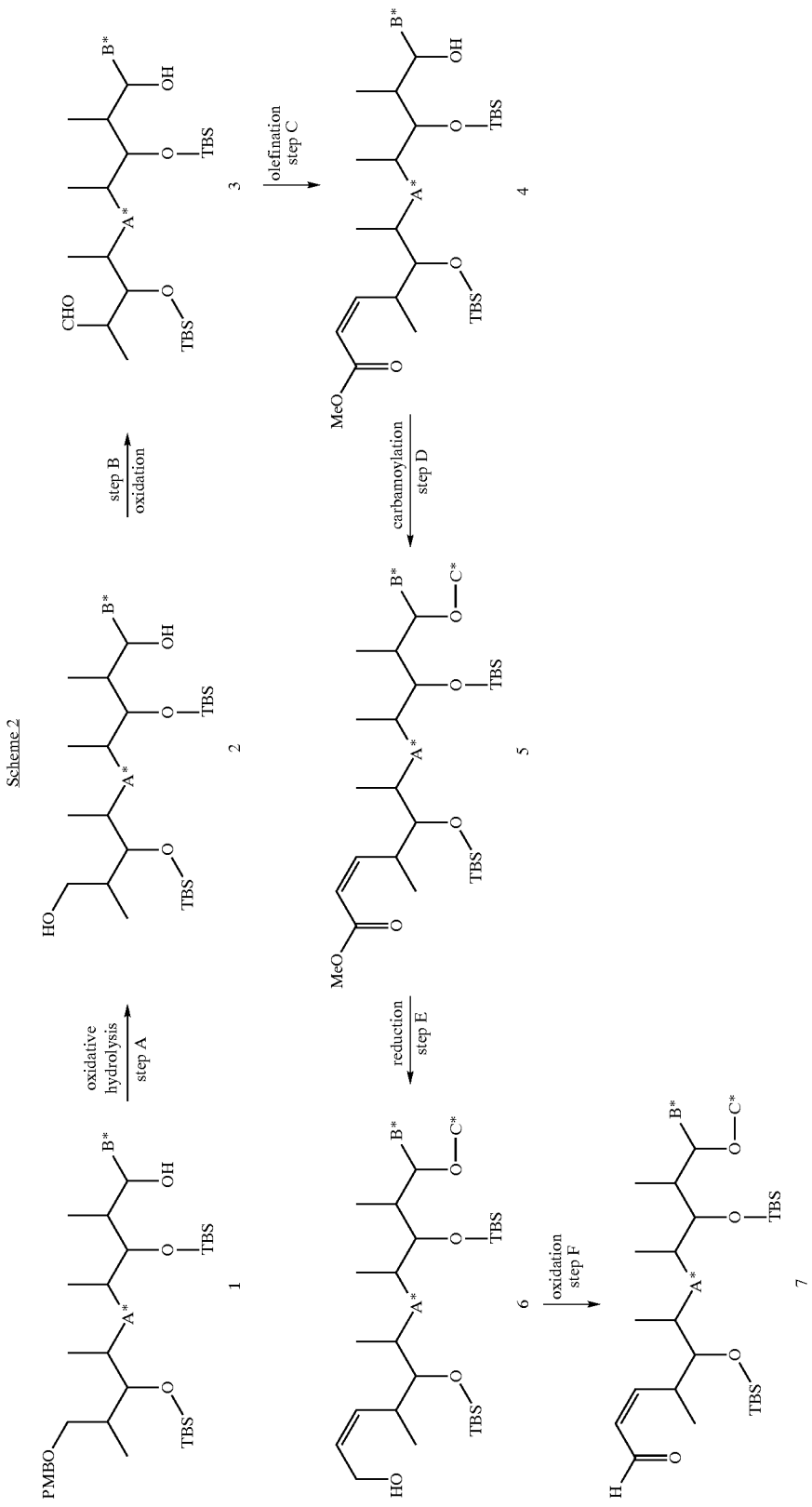

As to the individual steps in Scheme 2, Step A involves the oxidative hydrolysis of a para-methoxybenzyl ether of formula 1 to a diol of formula 2. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

Step B involves the oxidation of an alcohol of formula 2 to obtain an aldehyde of formula 3. The oxidation is conducted in the presence of: 1) an oxidizing reagent, preferably a mild oxidizing reagent such as the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for 3 hours.

Step C involves the olefination of an aldehyde of formula 3 with an olefinating reagent, preferably $(CF_3CH_2O)_2P(O)CH_2CO_2CH_3$, to obtain an olefin of formula 4. The olefination is conducted in the presence of: 1) a strong base, preferably an alkali metal salt such as potassium hexamethyldisilazide or butyllithium; and 2) an inert organic solvent, preferably a hydrocarbon such as toluene, or an ether such as tetrahydrofuran, at a temperature of between −78° C. and 25° C., preferably at 0° C., for a period of between 10 minutes and 48 hours, preferably for 3 hours.

Step D concerns the carbamoylation of the olefin of formula 4 with an isocyanate either of formula C*NCO or $Cl_3C(O)NCO$ to give a carbamate of formula 5. In the case of using C*NCO, the carbamoylation is conducted in the presence of a Lewis acid such as $Bu_2Sn(OAc)_2$ or a weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using $Cl_3C(O)NCO$, which produces substituted polyketides of formula I where C=H, the carbamoylation is conducted in the presence of a polar aprotic solvent, preferably a halogenated solvent such as methylene chloride, at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step E involves the reduction of a carbamate of formula 5 to obtain an alcohol of formula 6. The reduction is conducted in the presence of: 1) a reducing reagent, preferably an aluminum hydride reagent such as diisobutylaluminum hydride; and 2) an inert organic solvent, preferably a polar organic solvent such as methylene chloride, at a temperature of between −100° C. and 0° C., preferably at −78° C., for a period of between 10 minutes and 48 hours, preferably for 2 hours.

Step F involves the oxidation of an alcohol of formula 6 to obtain an aldehyde of formula 7. The oxidation is conducted in the presence of: 1) an oxidizing reagent, preferably a mild oxidizing reagent such as the Dess-Martin periodinane reagent; or the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for a period of between 1 and 3 hours.

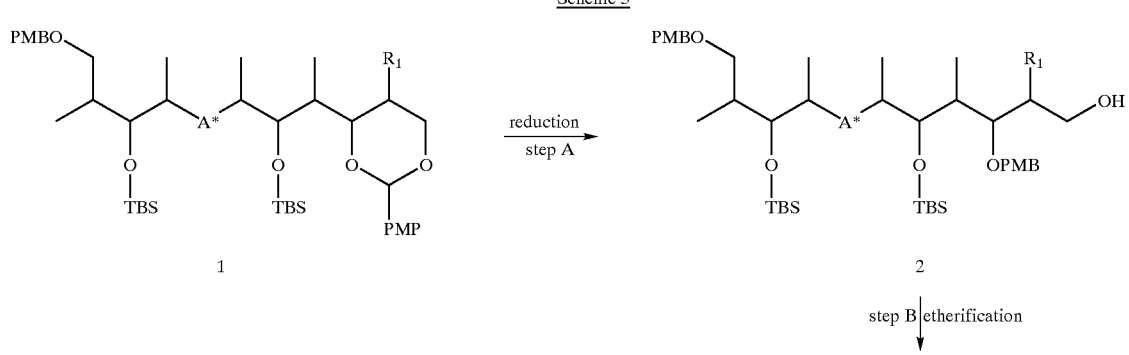

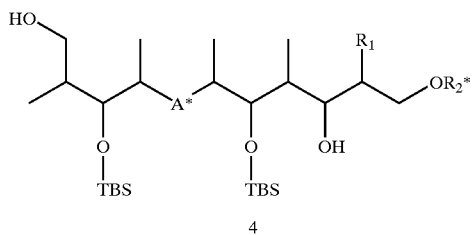

4

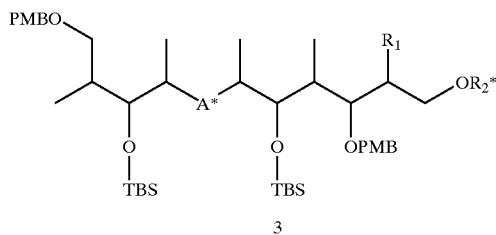

3

As to the individual steps in Scheme 3, Step A involves the reduction of a cyclic para-methoxyphenyl acetal of formula 1 to obtain an alcohol of formula 2. The reduction is conducted in the presence of: 1) a metal hydride, preferably an aluminum hydride such as diisobutylaluminum hydride; and 2) an aprotic organic solvent, preferably an ether such as tetrahydrofuran, at a temperature of between −100° C. and 10° C., preferably from −78° C. to 0° C., for a period of between 10 minutes and 8 hours, preferably for 2 hours.

Step B involves the etherification of an alcohol of formula 2 to obtain an ether of formula 3. The etherification is conducted in the presence of: 1) an alcohol of formula $R_2^*OH$, where $R_2^*$ is as described above; 2) a coupling reagent such as diethyl azodicarboxylate; 3) a phosphine such as triphenylphosphine; and 4) a polar organic solvent, such tetrahydrofuran, at a temperature of between −78° C. and 60° C., preferably between −20° C. and 40° C., for a period of between 2 and 72 hours, preferably for 16 hours. Alternatively, $R_2^*OH$ is replaced with an $R_2^*$halide or $R_2^*$sulfonate. In this case, the etherification is conducted in the presence of: 1) a base, preferably an alkali metal base, such as sodium hydride; 2) a polar organic solvent, such as N,N-dimethylformamide; and 3) an optional catalytic amount of an iodide salt, such as potassium iodide, at a temperature of between −78° C. and 60° C., preferably between −20° C. and 40° C., for a period of between 2 and 72 hours, preferably for 16 hours.

Step C involves the oxidative hydrolysis of an ether of formula 3 to a diol of formula 4. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

Scheme 4

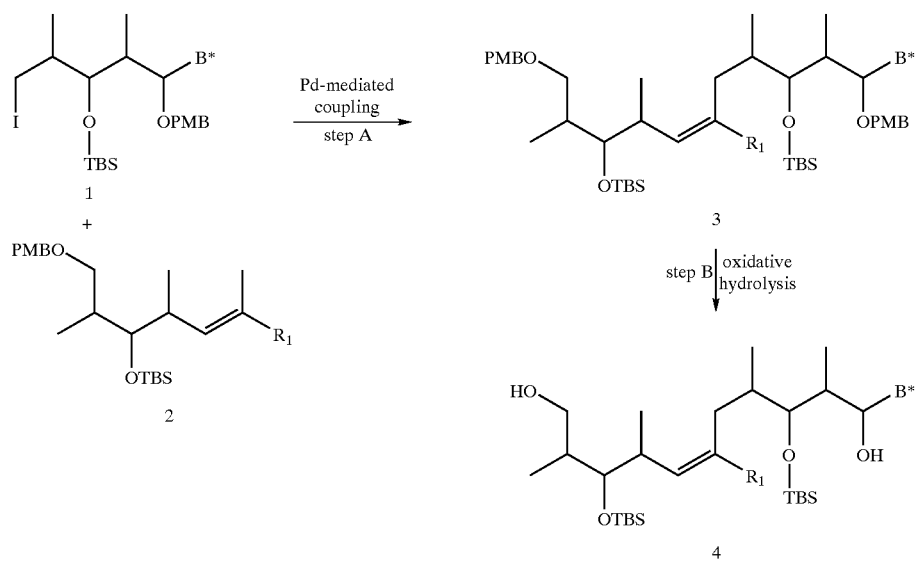

As to the individual steps in Scheme 4, Step A involves the palladium-mediated coupling of an alkyl iodide of formula 1 and a vinyl iodide of formula 2 to obtain an alkene of formula 3. The palladium-mediated coupling is conducted in the presence of: 1) a hindered organometallic reagent, preferably a hindered organolithium reagent such as t-butyllithium; 2) either a zinc halide such as zinc chloride or a hindered boron reagent such as 9-methoxy-9-borabicyclo[3.3.1]nonane; 3) a palladium reagent such as tetrakis(triphenylphosphine)palladium(0) or [1,1'-bis(diphenylphosphino)ferrocene]-dichloropalladium(II); and 4) a polar organic solvent, preferably an ether such as diethyl ether, at a temperature of between −78° C. and 25° C., for a period of between 1 hour and 72 hours.

Step B involves the oxidative hydrolysis of an alkene of formula 3 to a diol of formula 4. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

yldisilazide or butyllithium; and 2) an inert organic solvent, preferably a hydrocarbon such as toluene, or an ether such as tetrahydrofuran, at a temperature of between −78° C. and 25° C., preferably at 0° C., for a period of between 10 minutes and 48 hours, preferably for 3 hours.

Step B involves the oxidative hydrolysis of an alkene of formula 3 to a diol of formula 4. The oxidative hydrolysis is conducted in the presence of: 1) an oxidant, preferably a quinone such as 2,3-dichloro-5,6-dicyano-1,4-benzo-

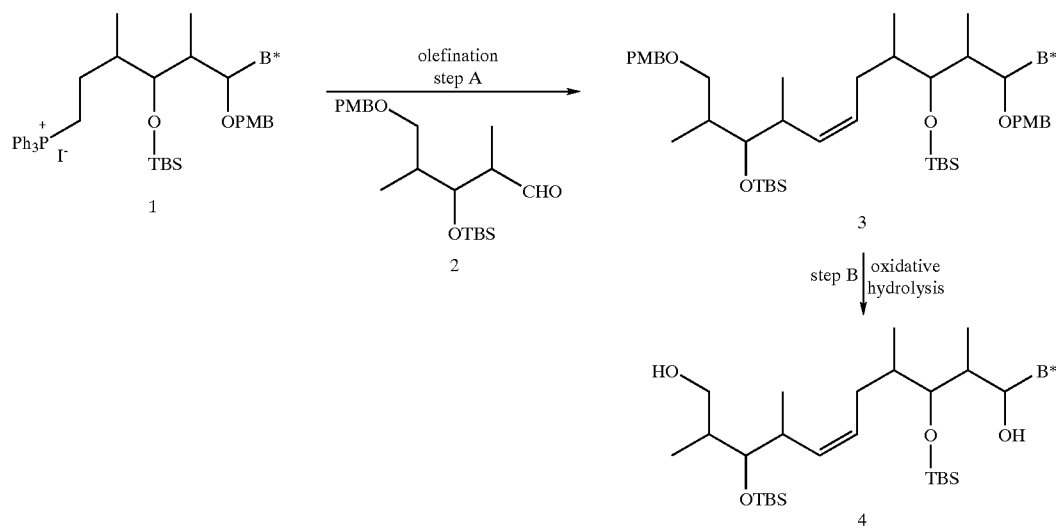

Scheme 5

As to the individual steps in Scheme 5, Step A involves the olefination of an aldehyde of formula 2 with a phosphonium salt of formula 1 to obtain an alkene of formula 3. The olefination is conducted in the presence of: 1) a strong base, preferably an alkali metal salt such as potassium hexamethyldisilazide or butyllithium; and 2) an inert organic solvent, preferably a hydrocarbon such as toluene, or an ether such as tetrahydrofuran, at a temperature of between −78° C. and 25° C., preferably at 0° C., for a period of between 10 minutes and 48 hours, preferably for 3 hours.

quinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

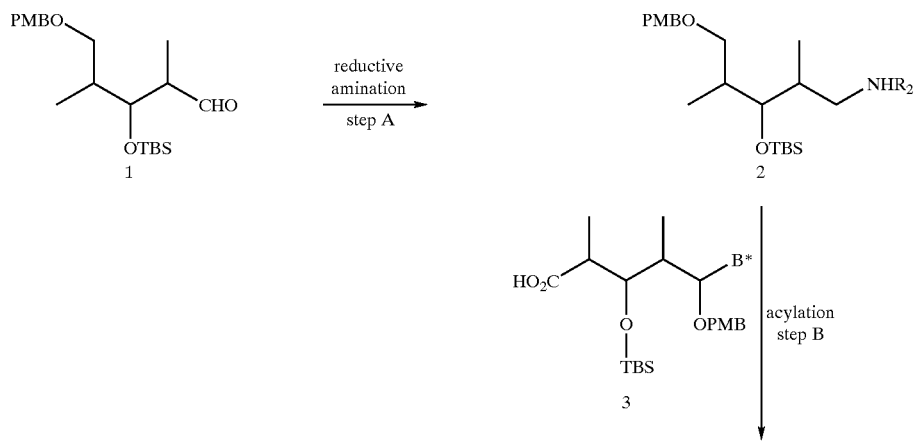

Scheme 6

-continued

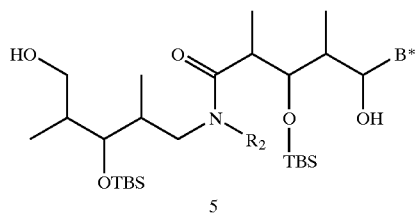

5

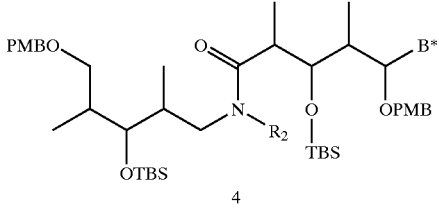

4

As to the individual steps in Scheme 6, Step A involves the reductive amination of an aldehyde of formula 1 to obtain an amine of formula 2. The reductive amination is conducted in the presence of: 1) an amine of formula $R_5NH_2$ where $R_5$ is as defined above; 2) a reducing agent, preferably a hydride, more preferably a borohydride salt such as sodium borohydride; and 3) a polar organic solvent, preferably a protic organic solvent such as ethanol, at a temperature of between 0° C. and 40° C., preferably from 5° C. to 25° C., for a period of between 10 minutes and 48 hours, preferably for 16 hours.

Step B involves the acylation of an amine of formula 2 to obtain an amide of formula 4. The acylation is conducted in the presence of: 1) a carboxylic acid of formula 3; 2) a carboxylic acid coupling reagent, preferably a diimide such as 1-(3-dimethylaminopropyl)-3-ethylcarbodiimide hydrochloride, and a suitable activating agent common to diimide coupling reactions, such as 1-hydroxybenzotriazole; and 3) a polar organic solvent, preferably a low molecular weight amide such as DMF, at a temperature of between 0° C. and 40° C., preferably at 25° C., for a period of between 1 and 24 hours.

Step C involves the oxidative hydrolysis of an amide of formula 4 to a diol of formula 5. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

Scheme 7

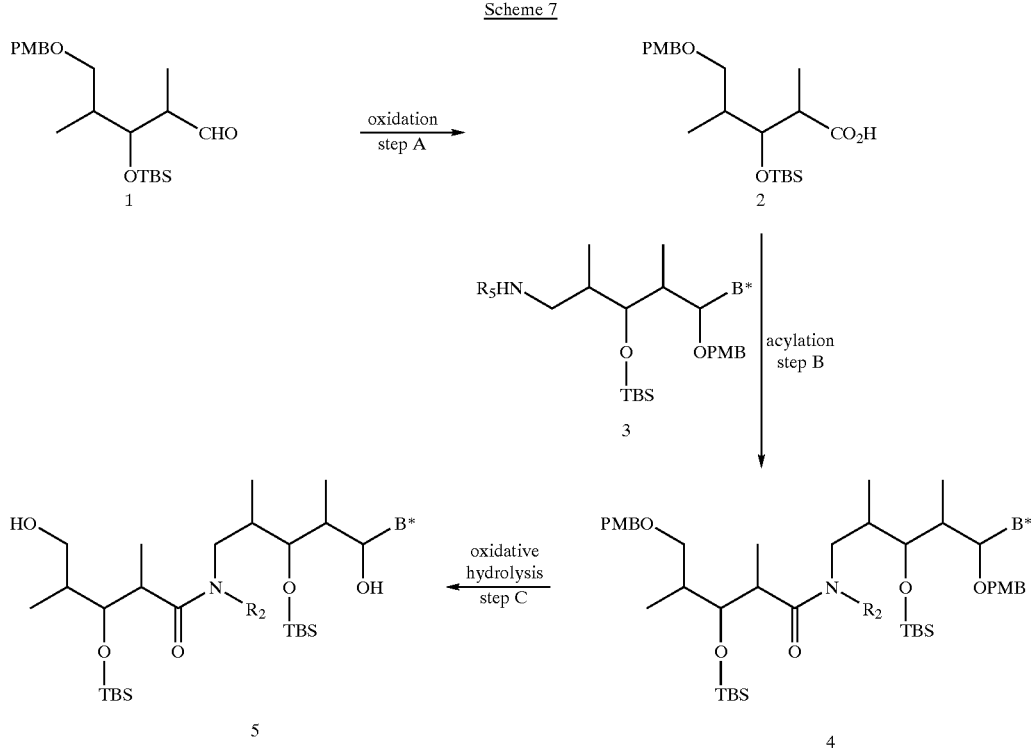

As to the individual steps in Scheme 7, Step A involves the oxidation of an aldehyde of formula 1 to obtain a carboxylic acid of formula 2. The oxidation is conducted in the presence of: 1) an oxidizing agent such as sodium chlorite; 2) a phosphate salt, preferably sodium dihydrogenphosphate; 3) a protic organic solvent, preferably an alcohol such as t-butanol; and 4) an alkene, preferably 2-methylpropene, at a temperature of between 0° C. and 40° C., preferably at 25° C., for a period of between 10 minutes and 8 hours, preferably for 1 hour.

Step B involves the acylation of an amine of formula 3 to obtain an amide of formula 4. The acylation is conducted in the presence of: 1) a carboxylic acid of formula 2; 2) a carboxylic acid coupling reagent, preferably a diimide such as 1-(3-dimethylaminopropyl)-3-ethylcarbodiimide hydrochloride, and a suitable activating agent common to diimide coupling reactions, such as 1-hydroxybenzotriazole; and 3) a polar organic solvent, preferably a low molcular weight amide such as DMF, at a temperature of between 0° C. and 40° C., preferably at 25° C., for a period of between 1 and 24 hours.

Step C involves the oxidative hydrolysis of an amide of formula 4 to a diol of formula 5. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

organic solvent, preferably a lower alkanol such as ethanol, at a temperature of between 0° C. and 40° C., preferably from 5° C. to 25° C., for a period of between 10 minutes and 48 hours, preferably for 16 hours.

Step B involves the acylation of an amine of formula 3 to obtain an amide of formula 4. The acylation is conducted in the presence of: 1) a carboxylic acid of formula $R_2{}^*CO_2H$ where $R_2{}^*$ is defined above; 2) a carboxylic acid coupling reagent, preferably a diimide such as 1-(3-dimethylaminopropyl)-3-ethylcarbodiimide hydrochloride, and a suitable activating agent common to diimide coupling reactions, such as 1-hydroxybenzotriazole; and 3) a polar organic solvent, preferably a low molcular weight amide such as DMF, at a temperature of between 0° C. and 40° C., preferably at 25° C., for a period of between 1 and 24 hours.

Step C involves the oxidative hydrolysis of an amide of formula 4 to a diol of formula 5. The oxidative hydrolysis is conducted in the presence of: 1) an oxidant, preferably a quinone such as 2,3-dichloro-5,6-dicyano-1,4-benzo-

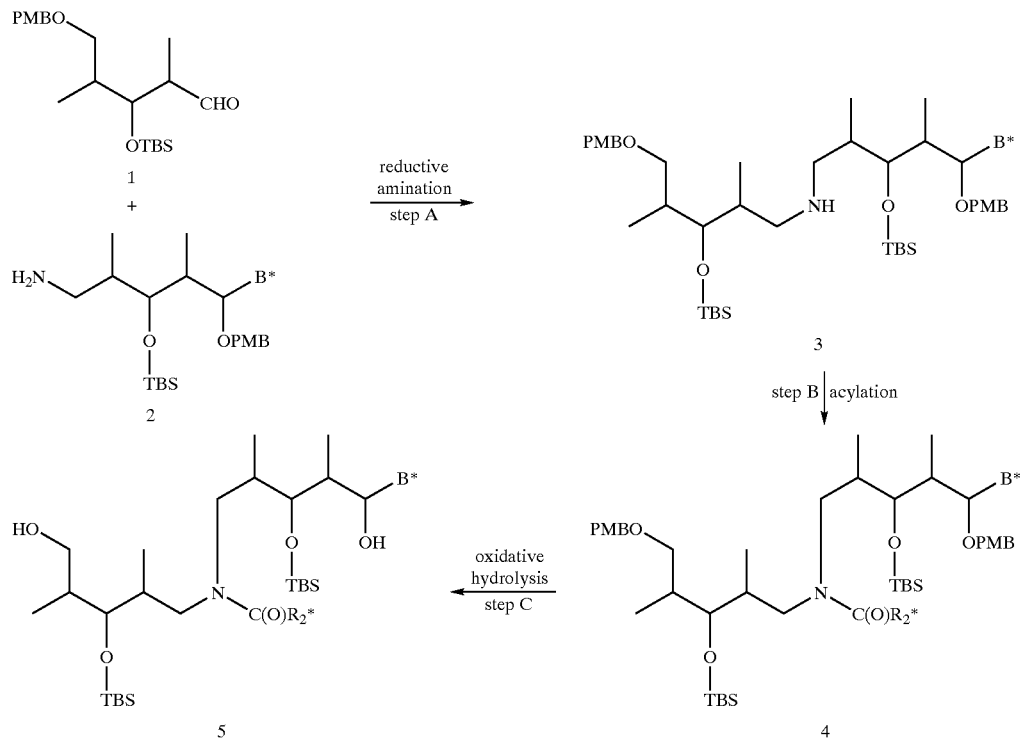

Scheme 8

As to the individual steps in Scheme 8, Step A involves the reductive amination of an aldehyde of formula 1 to obtain an amine of formula 3. The reductive amination is conducted in the presence of: 1) an amine of formula 2; 2) a reducing agent, preferably a hydride, more preferably a borohydride salt such as sodium borohydride; and 3) a polar quinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

Scheme 9

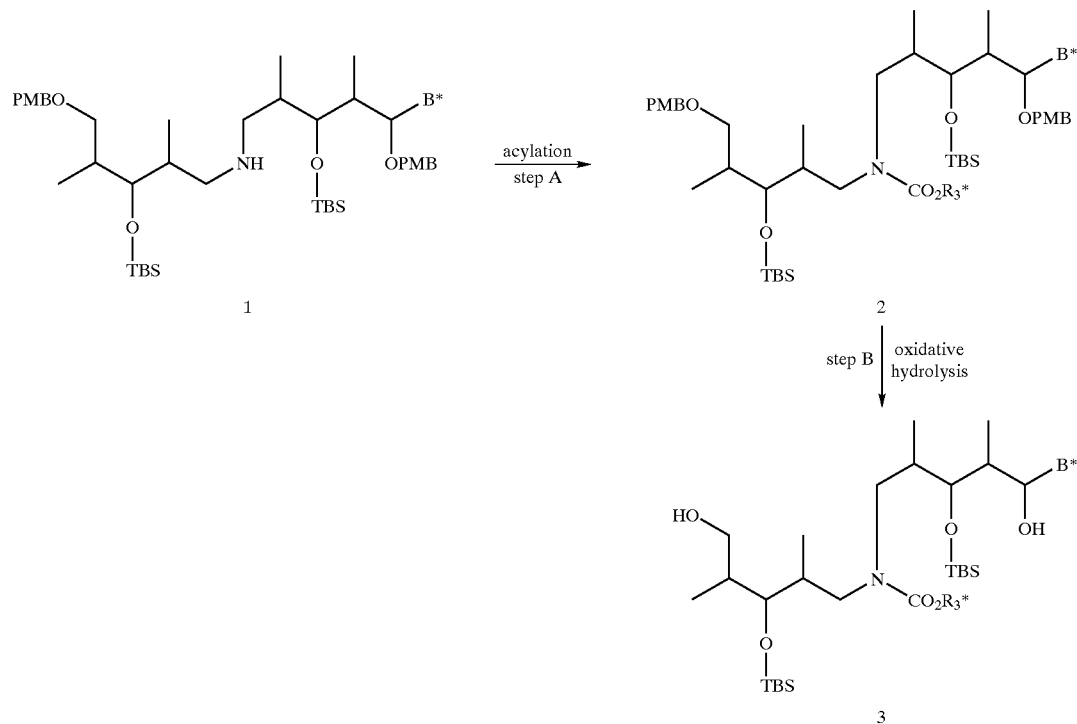

As to the individual steps in Scheme 9, Step A involves the acylation of an amine of formula 1 to obtain a carbamate of formula 2. The acylation is conducted in the presence of: 1) a chloroformate of formula $ClCO_2R_3^*$ where $R_3^*$ is defined above; 2) a weak base, preferably an amine such as triethylamine; and 3) a polar organic solvent, preferably a halogenated hydrocarbon such as methylene chloride, at a temperature of between −78° C. and 40° C., preferably at 5° C., for a period of between 1 and 24 hours.

Step B involves the oxidative hydrolysis of a carbamate of formula 2 to a diol of formula 3. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

Scheme 10

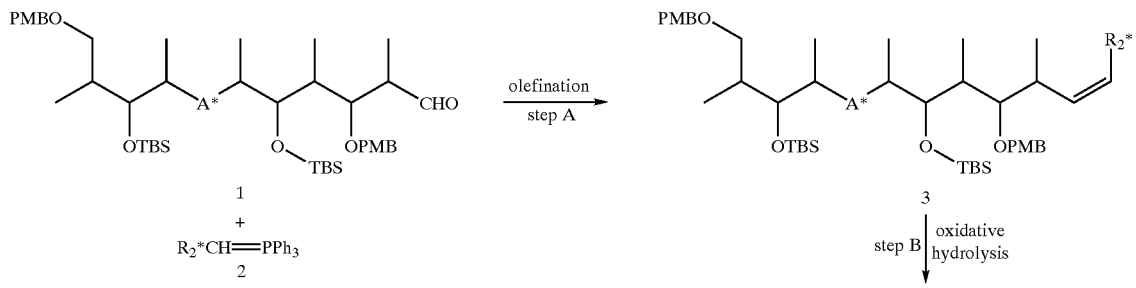

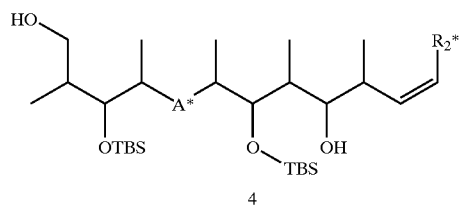

4

As to the individual steps in Scheme 10, Step A involves the olefination of an aldehyde of formula 1 with a phosphonium salt of formula 2 to obtain an alkene of formula 3. The olefination is conducted in the presence of: 1) a strong base, preferably an alkali metal salt such as potassium hexamethyldisilazide or butyllithium; and 2) an inert organic solvent, preferably a hydrocarbon such as toluene, or an ether such as tetrahydrofuran, at a temperature of between −78° C. and 25° C., preferably at 0° C., for a period of between 10 minutes and 48 hours, preferably for 3 hours.

Step B involves the oxidative hydrolysis of an alkene of formula 3 to a diol of formula 4. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

As to the individual steps in Scheme 11, Step A involves the olefination of an aldehyde of formula 1 with a phosphonate of formula 2 to obtain an olefin of formula 3. The olefination is conducted in the presence of: 1) a strong base, preferably a potassium salt such as potassium hexamethyldisilazide; 2) a crown ether such as 18-crown-6; and 3) an inert organic solvent, preferably a hydrocarbon such as toluene, at a temperature of between −78° C. and 25° C., preferably at 0° C., for a period of between 10 minutes and 48 hours, preferably for 3 hours.

Step B involves the oxidative hydrolysis of an alkene of formula 3 to a diol of formula 4. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

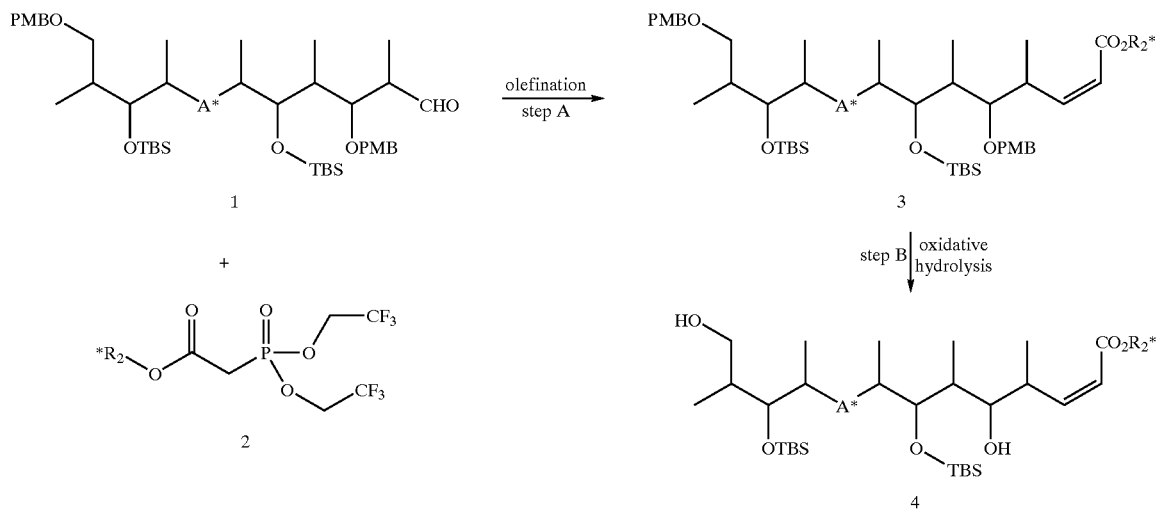

Scheme 11

Scheme 12

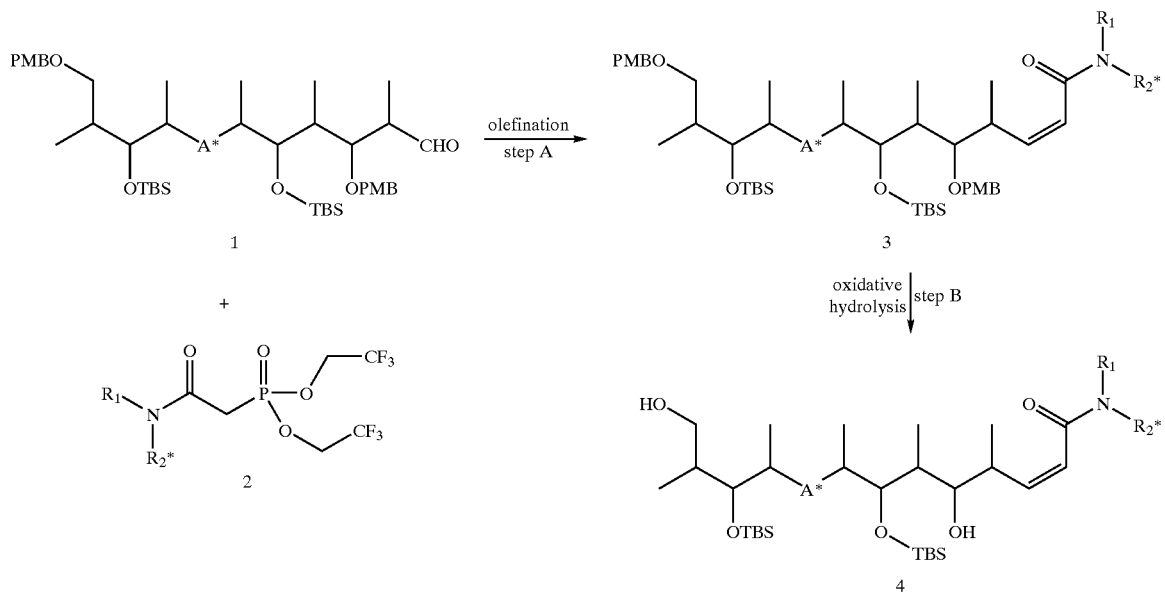

As to the individual steps in Scheme 12, Step A involves the olefination of an aldehyde of formula 1 with a phosphonate of formula 2 to obtain an olefin of formula 3. The olefination is conducted in the presence of: 1) a strong base, preferably a potassium salt such as potassium hexamethyldisilazide; 2) a crown ether such as 18-crown-6; and 3) an inert organic solvent, preferably a hydrocarbon such as toluene, at a temperature of between −78° C. and 25° C., preferably at 0° C., for a period of between 10 minutes and 48 hours, preferably for 3 hours.

Step B involves the oxidative hydrolysis of an alkene of formula 3 to a diol of formula 4. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

Scheme 13

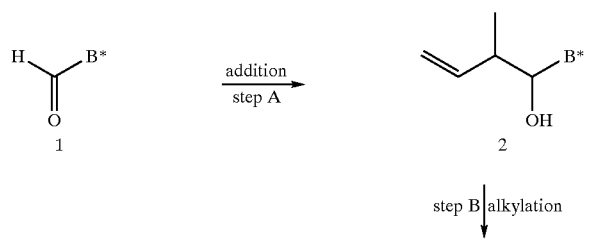

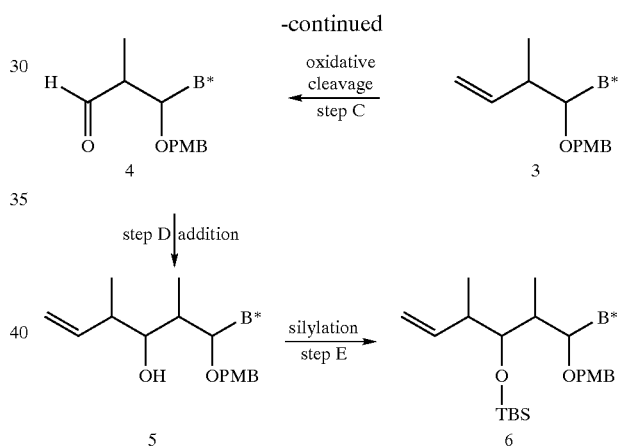

The syntheses described in Scheme 13 may be applied when B* is not —CH(R₁)CH=CH—CH=CH₂ or —CH(R₁)CH=CH₂. As to the individual steps in Scheme 13, Step A involves the addition of a butene group to an aldehyde of formula 1 to obtain an alcohol of formula 2. The addition is conducted in the presence of: 1) a crotylboron reagent, preferably a chiral crotylboron reagent, more preferably a Z-crotylboronate derived from diisopropyl tartrate; 2) an optional drying reagent such as molcular sieves; and 3) an inert organic solvent, preferably a hydrocarbon such as toluene, at a temperature of between −100° C. and 5° C., preferably at −78° C., for a period of between 10 minutes and 48 hours, preferably for 3 hours.

Step B involves the alkylation of an alcohol of formula 2 to obtain an alcohol of formula 3. The alkylation is conducted in the presence of: 1) a reactive benzylating reagent, preferably a reactive para-methoxybenzylating reagent such as p-methoxybenzyl-2,2,2-trichloroacetimidate; 2) a proton source, preferably a sulfonic acid such as pyridinium p-toluenesulfonate; and 3) a polar organic solvent, preferably a halogenated hydrocarbon such as methylene chloride, at a temperature of between −78° C. and 25° C., preferably at 0° C., for a period of between 10 minutes and 48 hours, preferably for 3 hours.

Step C involves the two stage oxidative cleavage of an alcohol of formula 3 to obtain an aldehyde of formula 4. The first stage of the oxidative cleavage is conducted in the presence of: 1) a dihydroxylating reagent, preferably an osmium reagent such as osmium tetroxide; 2) a cooxidant such as N-morpholine-N-oxide; and 3) a mixture of aprotic polar and protic solvents such as a mixture of acetone, water, and t-butanol, at a temperature of between −20° C. and 40° C., preferably at 25° C., for a period of between 10 minutes and 48 hours, preferably for 3 hours. The second stage of the oxidative cleavage is conducted in the presence of: 1) a periodate salt such as sodium periodate; and 2) a mixture of aprotic polar and protic solvents such as a mixture of tetrahydrofuran and water, at a temperature of between −20° C. and 40° C., preferably at 25° C., for a period of between 10 minutes and 48 hours, preferably for 3 hours.

Step D involves the addition of a butene group to an aldehyde of formula 4 to obtain an alcohol of formula 5. The addition is conducted in the presence of: 1) a crotyl addition reagent, preferably a crotyltin reagent such as crotyltributyltin; 2) a Lewis acid such as borontrifluoride etherate; and 3) an inert organic solvent, preferably a halogenated hydrocarbon such as methylene chloride, at a temperature of between −100° C. and 5° C., preferably at −78° C., for a period of between 10 minutes and 48 hours, preferably for 2 hours.

Step E involves the silylation of an alcohol of formula 5 to obtain a silyl ether of formula 6. The silylation is conducted in the presence of: 1) a silylating reagent, preferably a t-butyldimethylsilylating reagent such as t-butyldimethylsilyltriflate; 2) a weak base, preferably a nitrogen-containing base, more preferably a pyridine base such as 2,6-lutidine; and 3) an inert organic solvent, preferably a halogenated hydrocarbon such as methylene chloride, at a temperature of between −100° C. and 5° C., preferably at −20° C., for a period of between 10 minutes and 48 hours, preferably for 2 hours.

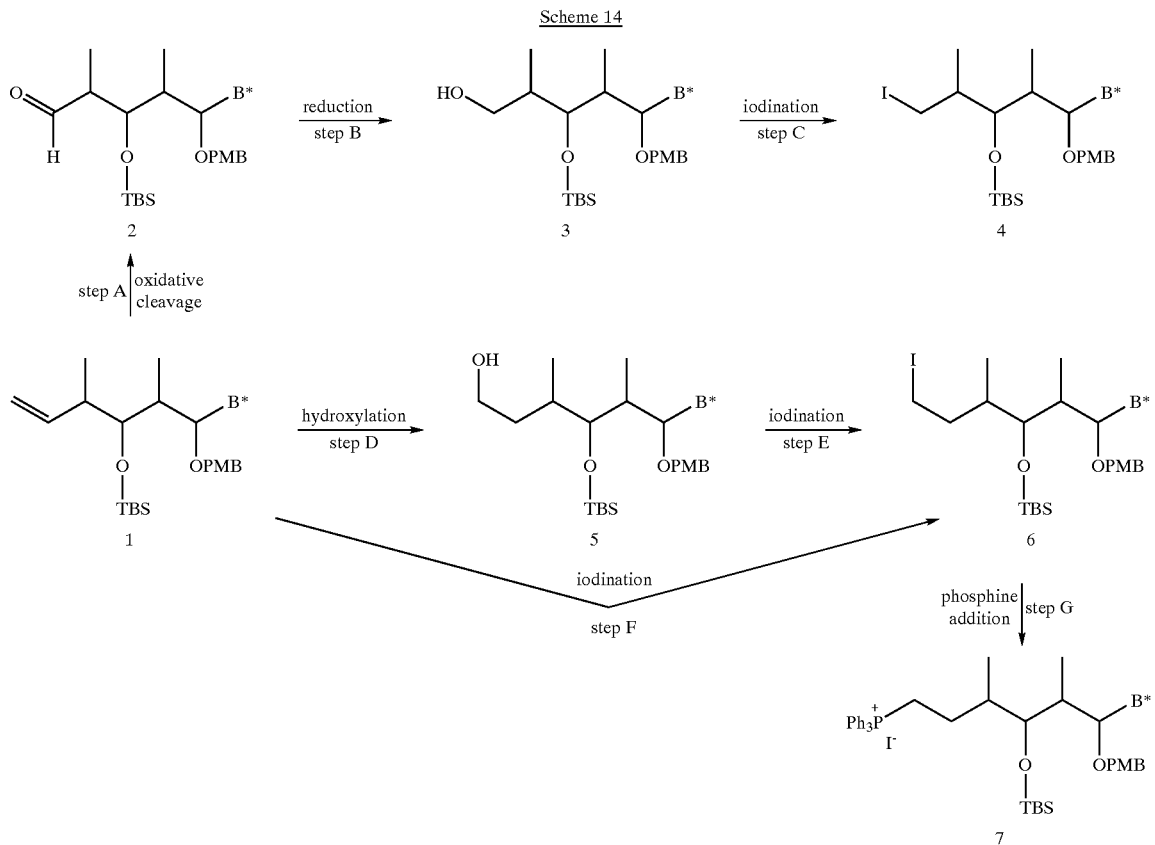

Scheme 14

The syntheses described in Scheme 14 may be applied when B* is not —CH($R_1$)CH=CH—CH=$CH_2$ or —CH($R_1$)CH=$CH_2$. As to the individual steps in Scheme 14, Step A involves the two stage oxidative cleavage of an alkene of formula 1 to obtain an aldehyde of formula 2. The first stage of the oxidative cleavage is conducted in the presence of: 1) a dihydroxylating reagent, preferably an osmium reagent such as osmium tetroxide; 2) a cooxidant such as N-morpholine-N-oxide; and 3) a mixture of aprotic polar and protic solvents such as a mixture of acetone, water, and t-butanol, at a temperature of between −20° C. and 40° C., preferably at 25° C., for a period of between 10 minutes and 48 hours, preferably for 3 hours. The second stage of the oxidative cleavage is conducted in the presence of: 1) a periodate salt such as sodium periodate; and 2) a mixture of aprotic polar and protic solvents such as a mixture of tetrahydrofuran and water, at a temperature of between −20° C. and 40° C., preferably at 25° C., for a period of between 10 minutes and 48 hours, preferably for 3 hours.

Step B involves the reduction of an aldehyde of formula 2 to obtain an alcohol of formula 3. The reduction is conducted in the presence of: 1) a hydride reducing agent, preferably an aluminum hydride such as lithium aluminum hydride or diisobutylaluminum hydride, or a borohydride such as sodium borohydride; and 2) a polar organic solvent, preferably an ether such as tetrahydrofuran, at a temperature of between −100° C. and 40° C., preferably from −20° C. to 25° C., for a period of between 10 minutes and 48 hours, preferably for 2 hours.

Step C involves the iodination of an alcohol of formula 3 to obtain an iodide of formula 4. The iodination is conducted in the presence of: 1) an iodinating reagent such as $I_2$; 2) a phosphorus-containing compound such as triphenylphoshine; 3) a weak base, preferably a weak nitrogen-containing base such as imidazole; and 4) a polar organic solvent, preferably an ester such as ethyl acetate, at a temperature of between −10° C. and 40° C., preferably at 25° C., for a period of between 10 minutes and 48 hours, preferably for 2 hours.

Step D involves the two stage hydroxylation of an alkene of formula 1 to obtain an alcohol of formula 5. The first stage of the hydroxylation is conducted in the presence of: 1) a borane such as 9-borabicyclo[3.3.1]nonane; and 2) a polar organic solvent, preferably an ether such as tetrahydrofuran, at a temperature of between −10° C. and 40° C., preferably at 0° C., for a period of between 1 hour and 48 hours, preferably for 24 hours. The second stage of the hydroxylation is conducted in the presence of: 1) an oxidant, preferably a peroxide such as hydrogen peroxide; 2) a strong alkali base, preferably a hydroxide base such as sodium hydroxide; and 3) a polar organic solvent, preferably an ether such as tetrahydrofuran, at a temperature of between −10° C. and 40° C., preferably at 0° C., for a period of between 10 minutes and 8 hours, preferably for 1 hour.

Step E involves the iodination of an alcohol of formula 5 to obtain an iodide of formula 6. The iodination is conducted in the presence of: 1) an iodinating reagent such as $I_2$; 2) a phosphorus-containing compound such as triphenylphoshine; 3) a weak base, preferably a weak nitrogen-containing base such as imidazole; and 4) a polar organic solvent, preferably an ester such as ethyl acetate, at a temperature of between −10° C. and 40° C., preferably at 25° C., for a period of between 10 minutes and 48 hours, preferably for 2 hours.

Step F involves the two stage iodination of an alkene of formula 1 to obtain an iodide of formula 6. The first stage of the iodination is conducted in the presence of: 1) a borane such as 9-borabicyclo[3.3.1]nonane; and 2) a polar organic solvent, preferably an ether such as tetrahydrofuran, at a temperature of between −10° C. and 40° C., preferably at 0° C., for a period of between 1 hour and 48 hours, preferably for 24 hours. The second stage of the iodination is conducted in the presence of $I_2$; and 2) a polar organic solvent, preferably an ether such as tetrahydrofuran, at a temperature of between −10° C. and 40° C., preferably at 0° C., for a period of between 10 minutes and 8 hours.

Step G involves the phoshine addition reaction of an iodide of formula 6 to obtain a phosphonium iodide salt of formula 7. The phoshine addition reaction is conducted in the presence of: 1) a phosphorus reagent such as triphenylphosphine; 2) a base, preferably an amine base such as diisopropylethylamine; and 3) an organic solvent, preferably a polar aprotic solvent such as acetonitrile, at a temperature of between 25° C. and 150° C., preferably at 90° C., for a period of between 1 hour and 72 hours, preferably for 18 hours.

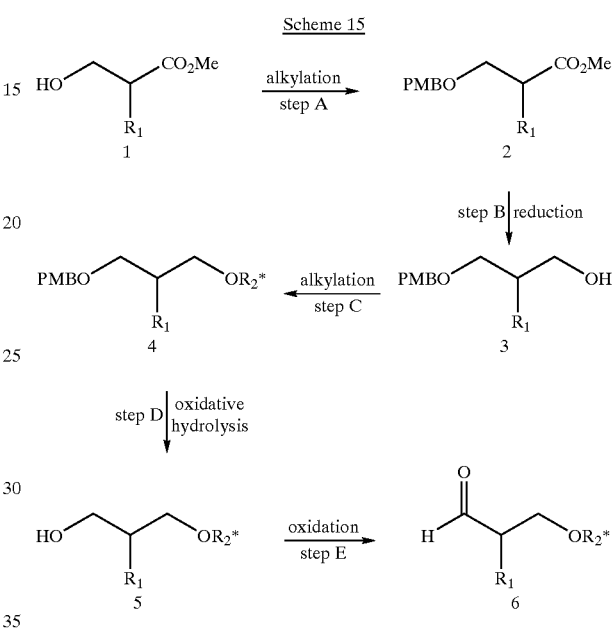

Scheme 15

As to the individual steps in Scheme 15, Step A involves the alkylation of an alcohol of formula 1 to obtain an ether of formula 2. The alkylation is conducted in the presence of: 1) a reactive benzylating reagent, preferably a reactive para-methoxybenzylating reagent such as p-methoxybenzyl-2,2,2trichloroacetimidate; 2) a proton source, preferably a sulfonic acid such as pyridinium p-toluenesulfonate; and 3) a polar organic solvent, preferably a halogenated hydrocarbon such as methylene chloride, at a temperature of between −78° C. and 25° C., preferably at 0° C., for a period of between 10 minutes and 48 hours, preferably for 3 hours.

Step B involves the reduction of an ether of formula 2 to obtain an alcohol of formula 3. The reduction is conducted in the presence of: 1) a metal hydride, preferably an aluminum hydride such as lithium aluminum hydride or diisobutylaluminum hydride; and 2) a polar organic solvent, preferably an ether such as tetrahydrofuran, at a temperature of between −100° C. and 10° C., preferably from −78° C. to 0° C., for a period of between 10 minutes and 8 hours, preferably for 2 hours.

Step C involves the alkylation of an alcohol of formula 3 to obtain an ether of formula 4. The alkylation is conducted in the presence of: 1) an alcohol of formula A*OH, where A* is as described above; 2) a coupling reagent such as diethyl azodicarboxylate; 3) a phosphine such as triphenylphosphine; and 4) a polar organic solvent, such tetrahydrofuran, at a temperature of between −78° C. and 60° C., preferably between −20° C. and 40° C., for a period of between 2 and 72 hours, preferably for 16 hours.

Step D involves the oxidative hydrolysis of an ether of formula 4 to an alcohol of formula 5. The oxidative hydrolysis is conducted in the presence of: 1) an oxidant, preferably a quinone such as 2,3-dichloro-5,6-dicyano-1,4-benzoquinone; 2) water; and 3) a polar organic solvent, preferably a halogenated hydrocarbon such as methylene chloride, at a temperature of between −20° C. and 40° C., preferably at 25° C., for a period of between 1 hour and 72 hours, preferably for 1 hour.

Step E involves the oxidation of an alcohol of formula 5 to obtain an aldehyde of formula 6. The oxidation is conducted in the presence of: 1) an oxidizing reagent, preferably a mild oxidizing reagent such as the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for 3 hours.

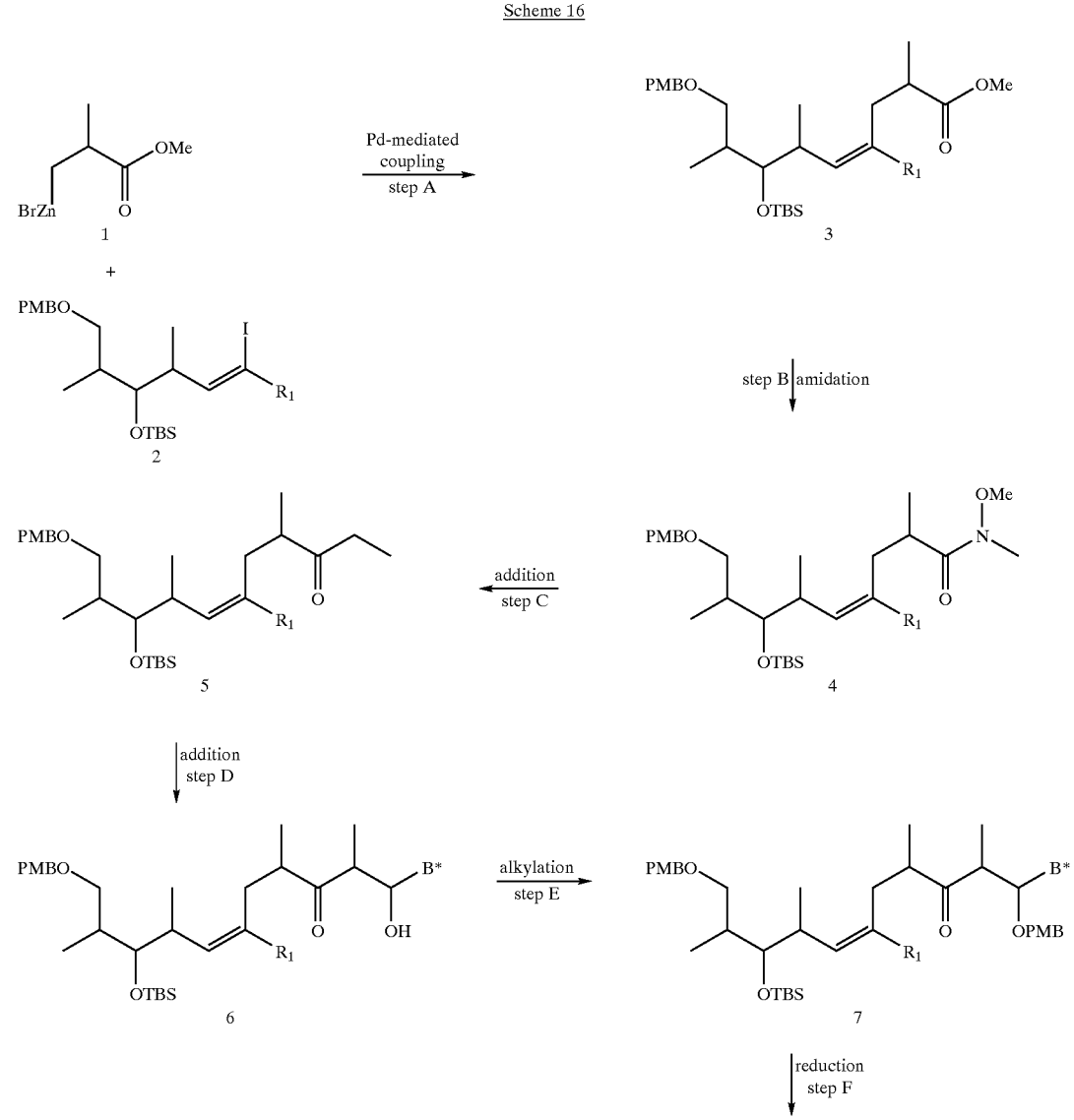

Scheme 16

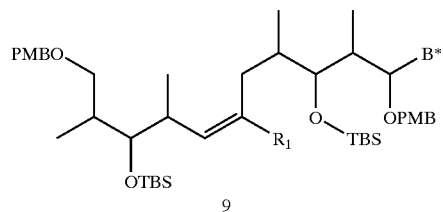

9

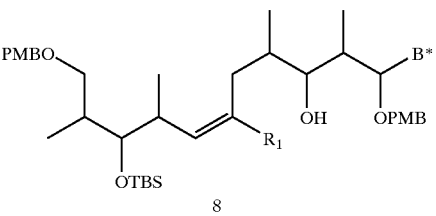

8

As to the individual steps in Scheme 16, Step A involves the palladium-mediated coupling of an alkyl zinc bromide of formula 1 and a vinyl iodide of formula 2 to obtain an alkene of formula 3. The palladium-mediated coupling is conducted in the presence of: 1) a palladium reagent such as tetrakis(triphenylphosphine)palladium(0); and 2) a polar organic solvent, preferably an ether such as diethyl ether or tetrahydrofuran, at a temperature of between −78° C. and 25° C., for a period of between 1 hour and 72 hours.

Step B involves the amidation of an alkene of formula 3 to obtain an amide of formula 4. The amidation is conducted in the presence of: 1) an O,N-dialkylated hydroxylamine such as N,N-dimethylhydroxylamine hydrochloride; 2) an organometallic reagent, preferably an alkylmagnesium halide or a trialkylaluminum reagent such as trimethylaluminum; and 3) an organic solvent, preferably a hydrocarbon such as toluene or hexane, or a mixture of the two, at a temperature of between −20° C. and 40° C., preferably at 25° C., for a period of between 1 hour and 72 hours, preferably for 1 hour.

Step C involves the addition reaction of an amide of formula 4 with a metalloalkane, preferably an alkyllithium or alkylmagnesium halide reagent such as ethylmagnesium bromide, to obtain a ketone of formula 5. The addition reaction is conducted in the presence of a polar organic solvent such as tetrahydrofuran, at a temperature of between −100° C. and 0° C., preferably at −78° C., for a period of between 1 hour and 72 hours, preferably for 4 hours.

Step D involves the addition reaction of a ketone of formula 5 with an aldehyde of formula B*CHO, where B is as described above, to obtain a hydroxyketone of formula 6. The addition reaction is conducted in the presence of: 1) a Lewis acid, preferably a boron or titanium reagent such as trisopropoxytitanium chloride; and 2) a polar organic solvent, preferably an ether such as diethyl ether or tetrahydrofuran, at a temperature of between −100° C. and 0° C., preferably at −78° C., for a period of between 1 hour and 72 hours, preferably for 16 hours.

Step E involves the alkylation of a hydroxyketone of formula 6 to obtain an ether of formula 7. The alkylation is conducted in the presence of: 1) a reactive benzylating reagent, preferably a reactive para-methoxybenzylating reagent such as p-methoxybenzyl-2,2,2-trichloroacetimidate; 2) a proton source, preferably a sulfonic acid such as pyridinium p-toluenesulfonate; and 3) a polar organic solvent, preferably a halogenated hydrocarbon such as methylene chloride, at a temperature of between −78° C. and 25° C., preferably at 0° C., for a period of between 10 minutes and 48 hours, preferably for 3 hours.

Step F involves the reduction of an ether of formula 7 to obtain an alcohol of formula 8. The reduction is conducted in the presence of: 1) a reducing agent, preferably an aluminum hydride or borohydride, such as lithium tri-t-butoxyaluminum hydride; 2) a polar organic solvent, preferably an ether such as diethyl ether or tetrahydrofuran, at a temperature of between −100° C. and 0° C., preferably at −78° C., for a period of between 1 hour and 72 hours, preferably for 16 hours.

Step G involves the silylation of an alcohol of formula 8 to obtain an ether of formula 9. The silylation is conducted in the presence of: 1) a silylating reagent, preferably a t-butyldimethylsilylating reagent such as t-butyldimethylsilyltriflate; 2) a weak base, preferably a nitrogen-containing base, more preferably a pyridine base such as 2,6-lutidine; and 3) an inert organic solvent, preferably a halogenated hydrocarbon such as methylene chloride, at a temperature of between −100° C. and 5° C., preferably at −20° C., for a period of between 10 minutes and 48 hours, preferably for 2 hours.

Scheme 17

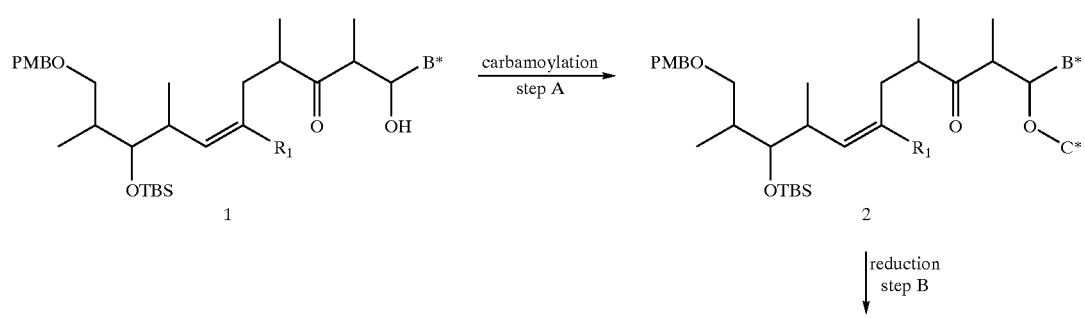

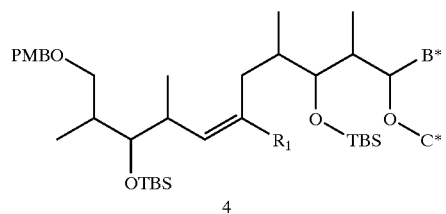

4

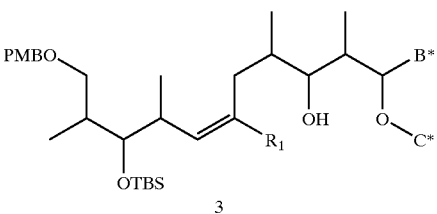

3

As to the individual steps in Scheme 17, Step A concerns the carbamoylation of the olefin of formula 1 with a an isocyanate either of formula C*NCO or Cl$_3$C(O)NCO to give a carbamate of formula 2. In the case of using C*NCO, the carbamoylation is conducted in the presence of a Lewis acid such as Bu$_2$Sn(OAc)$_2$ or a weak base such as triethylamine, in a polar aprotic solvent, preferably a halogenated solvent such as methylene chloride at a temperature of between −20° C. and 100° C., preferably between 0° C. and 50° C., for a period of between 5 minutes and 72 hours, preferably between 1 hour and 24 hours. In the case using Cl$_3$C(O)NCO, which produces substituted polyketides of formula I where C═H, the carbamoylation is conducted in the presence of a polar aprotic solvent, preferably a halogenated solvent such as methylene chloride at a temperature of between −20° C. and 100° C., preferably at 25° C., for a period of between 5 minutes and 72 hours, preferably between 1 hour and 8 hours; the work-up of this step is conducted in the presence of a protic organic solvent, preferably an alcohol such as methanol, in the presence of a base, for example, a carbonate such as potassium carbonate, at a temperature of between between 0° C. and 100° C., preferably at 25° C., for a period of between 5 minutes and 72 hours, preferably between 1 hour and 8 hours.

Step B involves the reduction of a carbamate of formula 2 to obtain an alcohol of formula 3. The reduction is conducted in the presence of: 1) a reducing agent, preferably an aluminum hydride or borohydride, such as lithium tri-t-butoxyaluminum hydride; and 2) a polar organic solvent, preferably an ether such as diethyl ether or tetrahydrofuran, at a temperature of between −100° C. and 0° C., preferably at −78° C., for a period of between 1 hour and 72 hours, preferably for 16 hours.

Step C involves the silylation of an alcohol of formula 3 to obtain an ether of formula 4. The silylation is conducted in the presence of: 1) a silylating reagent, preferably a t-butyldimethylsilylating reagent such as t-butyldimethylsilyltriflate; 2) a weak base, preferably a nitrogen-containing base, more preferably a pyridine base such as 2,6-lutidine; and 3) an inert organic solvent, preferably a halogenated hydrocarbon such as methylene chloride, at a temperature of between −100° C. and 5° C., preferably at −20° C., for a period of between 10 minutes and 48 hours, preferably for 2 hours.

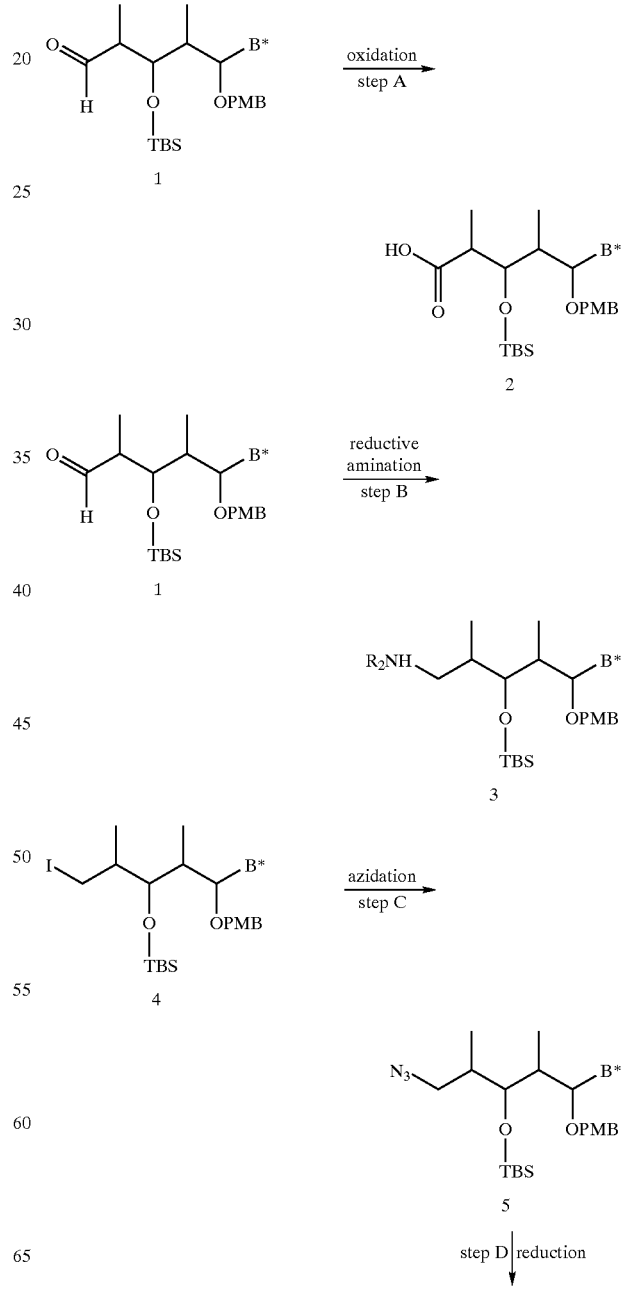

39

-continued

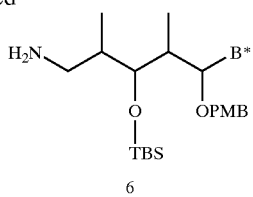

6

As to the individual steps in Scheme 18, Step A involves the oxidation an aldehyde of formula 1 to obtain a carboxylic acid of formula 2. The oxidation is conducted in the presence of: 1) an oxidizing agent such as sodium chlorite; 2) a phosphate salt, preferably sodium dihydrogenphosphate; 3) a protic organic solvent, preferably an alcohol such as t-butanol; and 4) an alkene, preferably 2-methylpropene, at a temperature of between 0° C. and 40° C., preferably at 25° C., for a period of between 10 minutes and 8 hours, preferably for 1 hour.

Step B involves the reductive amination of an aldehyde of formula 1 to obtain an amine of formula 3. The reductive amination is conducted in the presence of: 1) an amine of formula $R_5NH_2$, where $R_5$ is as defined above; 2) a reducing agent, preferably a hydride, more preferably a borohydride salt such as sodium borohydride; and 3) a polar organic solvent, preferably a protic organic solvent such as ethanol, at a temperature of between 0° C. and 40° C., preferably from 5° C. to 25° C., for a period of between 10 minutes and 48 hours, preferably for 16 hours.

Step C involves the azidation of an iodide of formula 4 to obtain an azide of formula 5. The azidation is conducted in the presence of: 1) an azide salt such as sodium azide; and 2) a polar organic solvent such as DMF, at a temperature of between 25° C. and 150° C., preferably at 90° C., for a period of between 10 minutes and 48 hours, preferably for 16 hours.

Step D involves the reduction of an azide of formula 5 to obtain an amine of formula 6. The azidation is conducted in the presence of: 1) a reducing agent, preferably a phosphine such as triphenylphoshine in the presence of water; and 2) a polar organic solvent such as tetrahydrofuran, at a temperature of between 0° C. and 100° C., preferably from 25° C. to 60° C., for a period of between 10 minutes and 48 hours, preferably for 16 hours.

Scheme 19

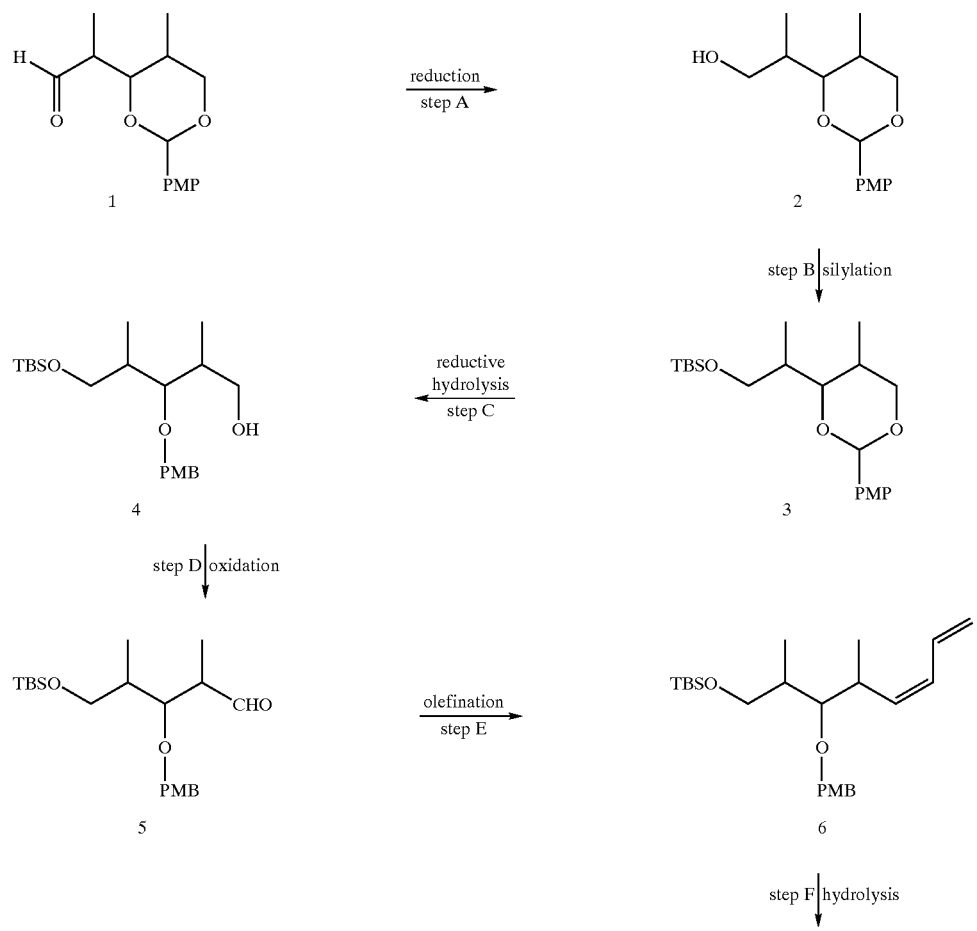

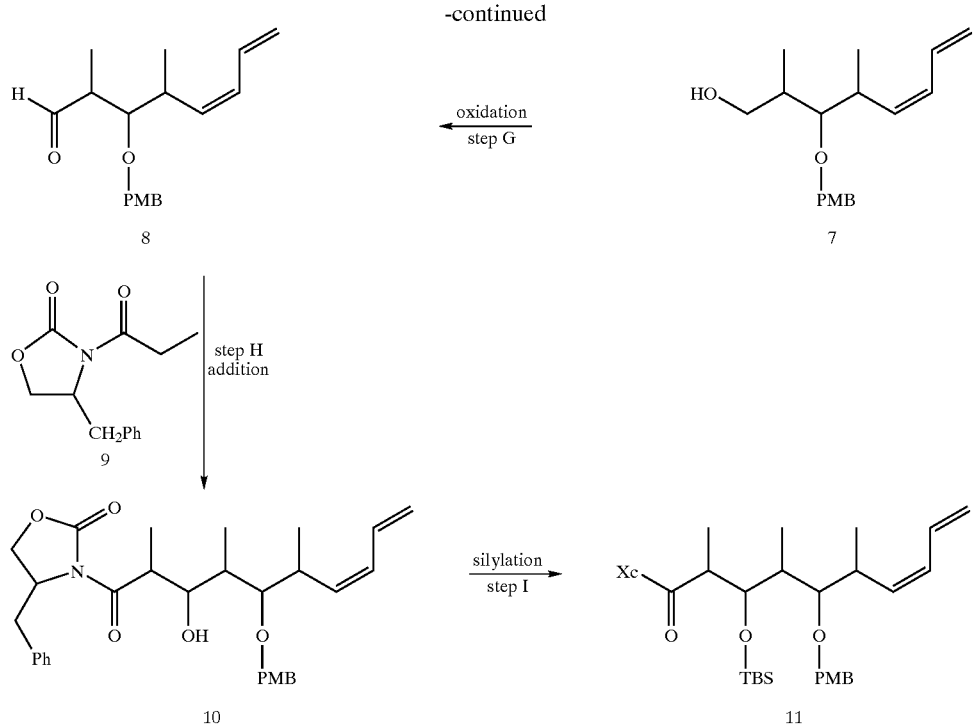

As to the individual steps in Scheme 19, Step A involves the reduction of an aldehyde of formula 1 to obtain an alcohol of formula 2. The reduction is conducted in the presence of: 1) a hydride reducing agent reagent, preferably an aluminum hydride such as lithium aluminum hydride or diisobutylaluminum hydride, or a borohydride such as sodium borohydride; and 2), a polar organic solvent, preferably an ether such as tetrahydrofuran, at a temperature of between −100° C. and 40° C., preferably from −20° C. to 25° C., for a period of between 10 minutes and 48 hours, preferably for 2 hours.

Step B involves the silylation of an alcohol of formula 2 to obtain a silyl ether of formula 3. The silylation is conducted in the presence of: 1) a silylating reagent, preferably a t-butyldimethylsilylating reagent such as t-butyldimethylsilyltriflate; 2) a weak base, preferably a nitrogen-containing base, more preferably a pyridine base such as 2,6-lutidine; and 3) an inert organic solvent, preferably a halogenated hydrocarbon such as methylene chloride, at a temperature of between −100° C. and 5° C., preferably at −20° C., for a period of between 10 minutes and 48 hours, preferably for 2 hours.

Step C involves the reductive hydrolysis of a silyl ether of formula 3 to obtain an alcohol of formula 4. The reductive hydrolysis is conducted in the presence of: 1) a Lewis acidic hydride, preferably an aluminum hydride such as diisobutylaluminumhydride; and 2) a polar organic solvent, preferably a halogenated hydrocarbon such as methylene chloride, at a temperature of between −100° C. and 5° C., preferably at −78° C., for a period of between 10 minutes and 48 hours, preferably for 1 hour.

Step D involves the oxidation of an alcohol of formula 4 to obtain an aldehyde of formula 5. The oxidation is conducted in the presence of: 1) an oxidizing reagent, preferably a mild oxidizing reagent such as the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for 3 hours.

Step E involves the olefination of an aldehyde of formula 5 to obtain a diene of formula 6. The olefination is conducted in the presence of: 1) a halogenated silyl propene such as 1-bromo-1-trimethylsilyl-2-propene; 2) a chromium(II) reagent such as chromium(II)chloride; and 3) a polar organic solvent, preferably an ether such as tetrahydrofuran, at a temperature of between −100° C. and 40° C., preferably at 20° C., for a period of between 10 minutes and 48 hours, preferably for 3 hours.

Step F involves the hydrolysis of a diene of formula 6 to obtain an alcohol of formula 7. The hydrolysis is conducted in the presence of: 1) a protic acid, preferably a hydrogen halide such as hydrochloric acid; and 2) a polar organic solvent, preferably an ether such as tetrahydrofuran, at a temperature of between −10° C. and 40° C., preferably at 20° C., for a period of between 10 minutes and 48 hours, preferably for 1 hour.

Step G involves the oxidation of an alcohol of formula 7 to obtain an aldehyde of formula 8. The oxidation is conducted in the presence of: 1) an oxidizing reagent, preferably a mild oxidizing reagent such as the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for 3 hours.

Step H involves the propionate addition reaction of an aldehyde of formula 8 to obtain an imide of formula 10. The propionate addition reaction is conducted in the presence of: 1) a propanimide of formula 9; 2) a Lewis acid, preferably a boron-containing Lewis acid such as dibutylborontriflate; 3) a weak base, preferably an amine base such as triethylamine; and 4) an inert organic solvent, preferably a polar organic solvent such as methylene chloride, at a temperature of between −100° C. and 20° C., preferably from −78° C. to 0° C., for a period of between 10 minutes and 48 hours, preferably for 2 hours.

Step I involves the silylation of an alcohol of formula 10 to obtain a silyl ether of formula 11. The silylation is conducted in the presence of: 1) a silylating reagent, preferably a t-butyldimethylsilylating reagent such as t-butyldimethylsilyltriflate; 2) a weak base, preferably a nitrogen-containing base, more preferably a pyridine base such as 2,6-lutidine; and 3) an inert organic solvent, preferably a halogenated hydrocarbon such as methylene chloride, at a temperature of between −100° C. and 5° C., preferably at −20° C., for a period of between 10 minutes and 48 hours, preferably for 2 hours.

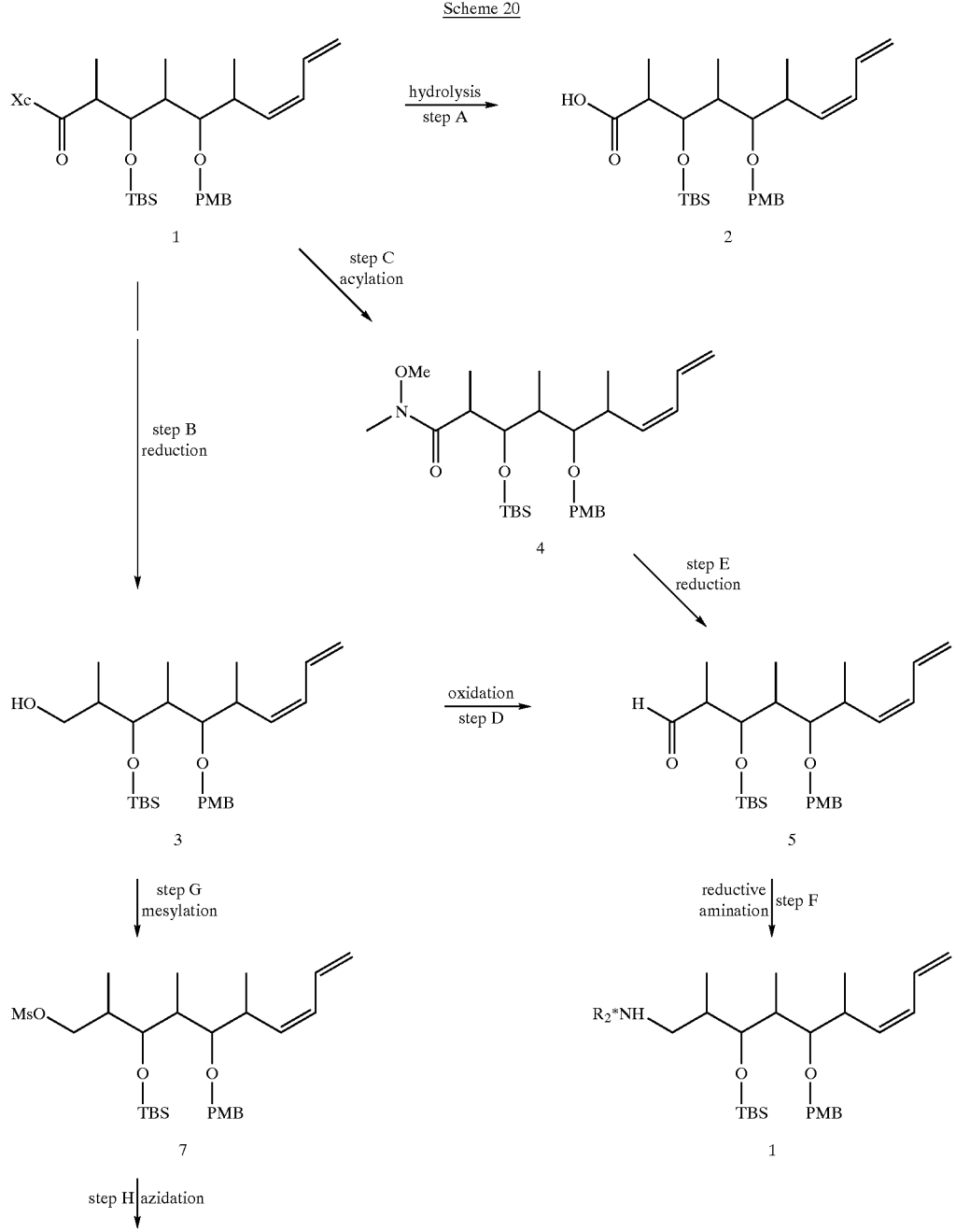

Scheme 20

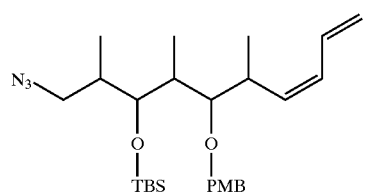

8 step I | reduction

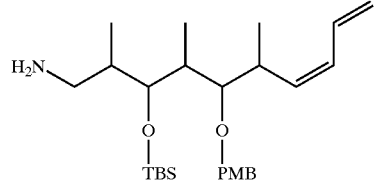

9

As to the individual steps in Scheme 20, Step A involves the hydrolysis of an imide of formula 1 to obtain a carboxylic acid of formula 2. The hydrolysis is conducted in the presence of: 1) a strong base, preferably a hydroxide salt such as lithium hydroxide; 2) an oxidant, preferably a peroxide such as hydrogen peroxide; and 3) a polar organic solvent, preferably an ether such as tetrahydrofuran, at a temperature of between −20° C. and 40° C., preferably from −10° C. to 25° C., for a period of between 10 minutes and 48 hours, preferably for 18 hours.

Step B involves the reduction of an imide of formula 1 to obtain an alcohol of formula 3. The reduction is conducted in the presence of: 1) a hydride reducing agent such as lithium borohydride; 2) a protic organic solvent, preferably a lower alkanol such as ethanol; and 3) a polar organic solvent, preferably an ether such as tetrahydrofuran, at a temperature of between −20° C. and 40° C., preferably at 25° C., for a period of between 10 minutes and 48 hours, preferably for 18 hours.

Step C involves the acylation of an imide of formula 1 to obtain an amide of formula 4. The acylation is conducted in the presence of: 1) N,O-dimethylhydroxylamine hydrochloride; 2) an organoaluminum reagent such as trimethylaluminum; and 3) a polar organic solvent, preferably an ether such as tetrahydrofuran, at a temperature of between −78° C. and 40° C., preferably at −20° C., for a period of between 10 minutes and 8 hours, preferably for 2 hours.

Step D involves the oxidation of an alcohol of formula 3 to obtain an aldehyde of formula 5. The oxidation is conducted in the presence of: 1) an oxidizing reagent, preferably a mild oxidizing reagent such as the combinations of oxalyl chloride, DMSO and triethylamine; sulfur trioxide-pyridine complex, DMSO and triethylamine; and 2,2,6,6-tetramethyl-1-piperidinyloxy free radical and diacetoxyiodobenzene; and 2) an inert organic solvent, preferably a polar organic solvent such as methylene chloride, at a temperature of between −78° C. and 40° C., preferably from −20° C. to 25° C., for a period of between 10 minutes and 48 hours, preferably for 3 hours.

Step E involves the reduction of an amide of formula 4 to obtain an aldehyde of formula 5. The reduction is conducted in the presence of: 1) a metal hydride, preferably an aluminum hydride such as lithium aluminum hydride or diisobutylaluminum hydride; and 2) a polar organic solvent, preferably an ether such as tetrahydrofuran, at a temperature of between −100° C. and 10° C., preferably from −78° C. to 0° C., for a period of between 10 minutes and 8 hours, preferably for 2 hours.

Step F involves the reductive amination of an aldehyde of formula 5 to obtain an amine of formula 6. The reductive amination is conducted in the presence of: 1) an amine of formula $R_5NH_2$, where $R_5$ is as defined above; 2) a reducing agent, preferably a hydride, more preferably a borohydride salt such as sodium borohydride; and 3) a polar organic solvent, preferably a protic organic solvent such as ethanol, at a temperature of between 0° C. and 40° C., preferably from 5° C. to 25° C., for a period of between 10 minutes and 48 hours, preferably for 16 hours.

Step G involves the mesylation of an alcohol of formula 3 to obtain a mesylate of formula 7. The mesylation is conducted in the presence of: 1) methanesulfonyl chloride; 2) a base, preferably an amine base such as triethylamine; and 3) a polar organic solvent, preferably a halogenated hydrocarbon such as such as methylene chloride, at a temperature of between −20° C. and 40° C., preferably from 0° C. to 5° C., for a period of between 10 minutes and 8 hours, preferably for 2 hours.

Step H involves the azidation of a mesylate of formula 7 to obtain an azide of formula 8. The azidation is conducted in the presence of: 1) an azide salt such as sodium azide; and 2) a polar organic solvent such as DMF, at a temperature of between 25° C. and 150° C., preferably at 90° C., for a period of between 10 minutes and 48 hours, preferably for 16 hours.

Step I involves the reduction of an azide of formula 8 to obtain an amine of formula 9. The azidation is conducted in the presence of: 1) a reducing agent, preferably a phosphine such as triphenylphoshine in the presence of water; and 2) a polar organic solvent such as tetrahydrofuran, at a temperature of between 0° C. and 100° C., preferably from 25° C. to 60° C., for a period of between 10 minutes and 48 hours, preferably for 16 hours.

Although the product of each reaction described above may, if desired, be purified by conventional techniques such as chromatography or recrystallization (if a solid), the crude product of one reaction is advantageously employed in the following reaction without purification.

As is evident to those skilled in the art, compounds of formula I contain asymmetric carbon atoms. It should be understood, therefore, that the individual stereoisomers are contemplated as being included within the scope of this invention.

As indicated above, all of the compounds of formula I are anti-tumor agents and are, therefore, useful in inhibiting the growth of various lymphomas, sarcomas, carcinomas, myelomas, and leukemia cell lines. The anti-tumor activity of the compounds of formula I may be demonstrated employing the Anchorage Dependent Growth Monolayer Assay (ADGMA) which measures the growth inhibitory effects of test compounds on proliferation of adherent cell monolayers. This assay was adapted from the 60 cell line assay used by the National Cancer Institute (NCI) with the following modifications: 1) four cell lines representative for the important tumor types, viz., MIP 101 colon carcinoma, HCT 116 colon carcinoma, 1A9 ovarian carcinoma and 1A9PTX22 ovarian carcinoma, were utilized; and 2) a tetrazolium derivative, viz., MTT, was utilized to determine cell density.

The ADGMA compares the number of viable cells following a 3-day exposure to a test compound relative to the number of cells present at the time the test compound was added. Cell viability is measured using a tetrazolium derivative, viz., 3-[4,5-dimethylthiazol-2-yl]-2,5-diphenyl-tetrazolium bromide (MTT) that is metabolically reduced in the presence of an electron coupling agent (PMS; phenazine methosulfate) by viable cells to a water-soluble formazan derivative. The absorbance at 540 nm (A540) of the formazan derivative is proportional to the number of viable cells. The $IC_{50}$ for a test compound is the concentration of compound required to reduce the final cell number to 50% of the final control cell number. If cell proliferation is inhibited, the assay further defines compounds as cytostatic (cell number after 3-day compound incubation>cell number at time of compound addition) or cytotoxic (cell number after 3-day compound incubation<cell number at time of compound addition).

The HCT 116 colon carcinoma cell line was obtained from the American Type Culture Collection (ATCC, Rockville, Md.). The MIP 101 colon carcinoma cell line was obtained from Dr. Robert Kramer (Bristol Meyers Squibb) and was previously described (Niles R M, Wilhelm S A, Steele G D JR, Burke B, Christensen T, Dexter D, O'Brien M J, Thomas P, Zamcheck N. Isolation and characterization of an undifferentiated human colon carcinoma cell line (MIP-101). Cancer Invest. 1987;5(6):545–52.). The 1A9 and the 1A9PTX22 ovarian tumor cell lines were obtained from Dr. Tito Fojo, Medicine Branch, Division of Clinical Sciences, National Cancer Institute, National Institutes of Health, Bethesda, Md. 20892. The 1A9 is a clone of the ovarian carcinoma cell line, A2780 (Giannakakou P, Sackett, D L, Kang Y-K, Zhan Z, Buters J T M, Fojo T, Poruchynsky M S. Paclitaxel-resistant human ovarian cancer cells have mutant δ-tubulins that impaired paclitaxel-driven polymerization. J. Biol. Chem. 1997, 272(4):17118–17125). The 1A9PTX22 subline was isolated as an individual clone from the 1A9 cell line in a single step selection by exposure to 5 ng/mL paclitaxel in the presence of 5 μg/mL of verapamil. All cell lines were used between passages 4–20 following thawing. MIP-101 colon carcinoma, HCT 116 colon carcinoma, 1A9 ovarian carcinoma and 1A9PTX22 ovarian carcinoma cell lines are maintained and plated in RPMI 1640 medium containing 10% fetal bovine serum.

Cells are trypsinized and counted using a hemacytometer to determine cell concentrations. Cells were then plated in their respective maintenance media (200 μL/well) in 96-well plates at the following concentrations: MIP-101, 2000 cells/well; HCT 116, 2000 cells/well; 1A9, 10000 cells/well; and 1A9PTX22, 10000 cells/well. The number of cells/well was determined in preliminary experiments, and resulted in 75–90% of confluency by day 4 after plating. Initial cell densities, assayed one day after plating, are roughly 0.10–0.20 A540 absorbance units greater than the media blank. Ninety-six well plates were seeded on day 0 and the test compounds are added on day 1. A "time 0" plate was created that received media only in row A and one cell line/row in rows B–E. The "time 0" plate was processed 24 hours after plating (at the time when drugs were added to experimental plates), as follows: 5 micoliters of the MTT stock solution (0.5 mg/mL in PBS) was added to each well and then incubated for three hours at 37° C., 5% CO2, in a humidified environment. Media was then carefully and completely removed. Plates were allowed to dry in the dark. DMSO (dimethylsulfoxide) was added to each well (100 μL/well) and plates were placed on an orbital shaker for 2 hours. Plates were read in the 96-well plate reader at 540 nm in a Molecular Devices plate reader utilizing Softmax Version 2.35 in absorbance mode-endpoint L-1, using DMSO as a blank. One day following plating, test compounds were added (in a final 1:10 dilution) to the test plates and subsequently serial diluted 10 times. Control plate received 1:10 dilution of the solvent (10% DMSO/90% RPMI 1640) only. Three days after addition of test compounds, all the experimental plates and the control plate were processed as described above for the "time 0" plate. $IC_{50}$ values are determined from graphs of percent net growth as a function of compound concentration. Percent net growth is calculated as (Cell+Drug $A_{540}$–Initial 540/Cell+Drug Vehicle 540–Initial 540).

The following $IC_{50}$ values (average of two or more separate experiments) in μM were obtained:

| Compound | MIP101 | HCT116 | 1A9 | 1A9PTX22 |
| --- | --- | --- | --- | --- |
| Ex. 1 | 3.8 | 0.2 | 0.03 | 0.18 |
| Ex. 2 | 20 | 13 | 4 | 6 |

-continued

| Compound | MIP101 | HCT116 | 1A9 | 1A9PTX22 |
|---|---|---|---|---|
| paclitaxel (a known antineoplastic compound) | 0.2 | 0.0003 | 0.047 | 0.001 |

The precise dosage of the compounds of formula I to be employed for inhibiting tumors depends upon several factors including the host, the nature and the severity of the condition being treated, the mode of administration and the particular compound employed. However, in general, satisfactory inhibition of tumors is achieved when a compound of formula I is administered parenterally, e.g., intraperitoneally, intravenously, intramuscularly, subcutaneously, intratumorally, or rectally, or enterally, e.g., orally, preferably intravenously or orally, more preferably intravenously at a single dosage of 1–300 mg/kg body weight per cycle (cycle=3–6 weeks) or, for most larger primates, a single dosage of 50–5000 mg per treatment cycle. A preferred intravenous single dosage per 3–6 week treatment cycle is 1–75 mg/kg body weight or, for most larger primates, a daily dosage of 50–1500 mg. A typical intravenous dosage is 45 mg/kg, once every three weeks.

Usually, a small dose is administered initially and the dosage is gradually increased until the optimal dosage for the host under treatment is determined. The upper limit of dosage is that imposed by side effects and can be determined by trial for the host being treated.

The compounds of formula I may be combined with one or more pharmaceutically acceptable carriers and, optionally, one or more other conventional pharmaceutical adjuvants and administered enterally, e.g., orally, in the form of tablets, capsules, caplets, etc. or parenterally, e.g., intraperitoneally or intravenously, in the form of sterile injectable solutions or suspensions. The enteral and parenteral compositions may be prepared by conventional means.

The compounds of formula I may be formulated into enteral and parenteral pharmaceutical compositions containing an amount of the active substance that is effective for inhibiting tumors, such compositions in unit dosage form and such compositions comprising a pharmaceutically acceptable carrier.

The compounds according to the invention can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. In particular, a compound of formula (I) can be administered, for example, in the case of tumor therapy in combination with chemotherapy, radiotherapy, immunotherapy, surgical intervention or a combination of these. Long-term therapy is equally possible as is adjuvant therapy in the context of other treatment strategies, as described above. Other possible treatments are therapy to maintain the patient's status after tumor regression, or even chemopreventive therapy, for example, in patients at risk.

Therapeutic agents for possible combination are especially one or more anti-proliferative, cytostatic or cytotoxic compounds, for example, a chemotherapeutic agent or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g., PKI166, the VEGF receptor tyrosine kinase, e.g., PTK787, or the PDGF receptor tyrosine kinase, e.g., STI571, a cytokine, a negative growth regulator, such as TGF-β or IFN-β, an aromatase inhibitor, e.g., letrozole or anastrozole, an inhibitor of the interaction of an SH2 domain with a phosphorylated protein, anti-estrogens, topoisomerase I inhibitors, such as irinotecan, topoisomerase II inhibitors, microtubule active agents, e.g., paclitaxel, discodermolide or an epothilone, alkylating agents, anti-neoplastic anti-metabolites, such as gemcitabine or capecitabine, platin compounds, such as carboplatin or cisplatin, antiangiogenic compounds, gonadorelin agonists, anti-androgens, bisphosphonates, e.g., AREDIA® or ZOMETA® and trastuzumab. The structure of the active agents identified by code nos., generic or trade names may be taken from the actual edition or the standard compendium "The Merck Index" or from databases, e.g., Patents International, e.g, IMS World Publications. The corresponding content thereof is hereby incorporated by reference.

The following examples show representative compounds encompassed by this invention and their synthesis. However, it should be clearly understood that it is for purposes of illustration only.

EXAMPLE 1

Synthesis of (2R,3S,4S,5S,7S,8Z,10S,11S,12S,13Z, 16S,17R,18S,19S,20S)-19-[(aminocarbonyl)oxy]-3, 5,7,11,17-pentahydroxy-2,3,4,10,12,14,16,18,20-nonamethyl-21-(phenylmethoxy)-8,13-heneicosadienoic acid δ-lactone.

a) Preparation of (5R,6S,7Z,10S,11R)-11-[(1R,2S,3S)-2-[(4-methoxyphenyl)methoxy]-1,3-dimethyl-4-(phenylmethoxy)butyl]-5-[(1S)-2-[(4-methoxyphenyl)methoxy]-1-methylethyl]-2,2,3,3,6,8,10,13,13,14,14-undecamethyl-4,12-dioxa-3,13-disilapentadec-7-ene.

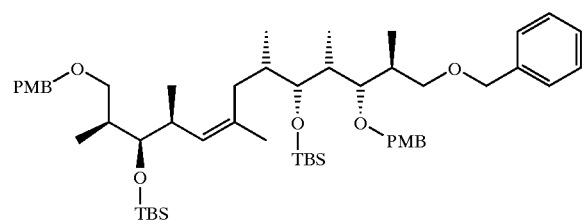

NaH (12 mg, 0.49 mmol, 2 eq) is added to a solution of (2S,3S,4R,5R,6S,8Z,10S,11R,12S)-5,11-bis[[(1,1-dimethylethyl)dimethylsilyl]oxy]-3,13-bis[(4-methoxyphenyl)methoxy]-2,4,6,8,10,12-hexamethyl-8-tridecen-1-ol (200 mg, 0.245 mmol, 1 eq) in DMF (3 mL) at −78° C. The reaction is slowly warm to 23° C. and is stirred for 1 h. Benzyl bromide (84 mg, 0.49 mmol, 2 eq) and potassium iodide (cat. 1 mg) are added and stirred for 18 h.

The solvent is removed. The crude product is chromatographed (from hexane to 10% EtOAc in hexane) to give 204 mg (80%) of the desired compound as a colorless oil.

¹H NMR (200 MHz, CDCl₃), δ 7.38–7.16 (m, 9H), 6.88–6.79 (d, J=10, 4H), 5.01–4.97 (d, J=8, 1H), 4.46–4.34 (m, 6H), 3.76 (s, 6H), 3.52–3.14 (m, 8H), 32.52–2.44 (m, 1H), 2.29–2.21 (m, 1H), 2.08–1.86 (m, 4H), 1.64–1.53 (m, 5H), 1.03–1.01 (d, J=4, 3H). 0.90–0.86 (m, 25H), 0.70–0.68 (d, J=4, 3H), 0.03 to −0.01 (m, 12H); ¹³C NMR (200 MHz, CDCl₃), δ 159.04, 138.73, 131.76, 131.37, 131.21, 131.04, 129.06, 129.02, 128.31, 127.54, 127.43, 113.74, 113.68, 82.43, 78.35, 74.45, 73.06, 72.70, 72.52, 72.32, 55.27, 55.26, 39.00, 38.78, 37.07, 37.00, 35.62, 34.78, 26.27, 26.15, 23.15, 18.52, 18.39, 17.08, 15.64, 14.50, 12.84, 11.06, −3.27, −3.86, −3.89. Mass spectrum (ESI), m/z 905, 922 (m+NH₃).

b) Preparation of (2S,3R,4S,5Z,8S,9R,10R,11S,12S)-3,9-bis [[(1,1-dimethylethyl)dimethylsilyl]oxy]-2,4,6,8,10,12-hexamethyl-13-(phenylmethoxy)-5-tridecene-1,11-diol.

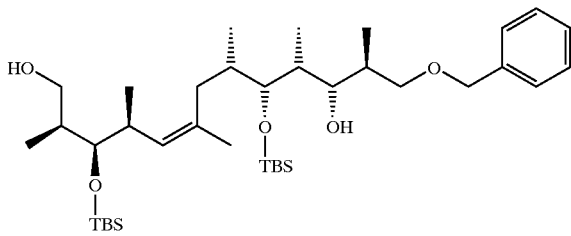

Water (3 mL) is added to a solution of (5R,6S,7Z,10S,11R)-11-[(1R,2S,3S)-2-[(4-methoxyphenyl)methoxy]-1,3-dimethyl-4-(phenylmethoxy)butyl]-5-[(1S)-2-[(4-methoxyphenyl)methoxy]-1-methylethyl]-2,2,3,3,6,8,10,13,13,14,14-undecamethyl-4,12-dioxa-3,13-disilapentadec-7-ene (1.0 g, 1.19 mmol) in CH₂Cl₂ (30 mL) at 23° C. and stirred for 5 min. DDQ (1.62 g, 7.14 mmol, 6 eq) is added at once and stirred for 15 min. The product mixture is concentrated. The residue is filtered through celite and washed with hexane. The hexane layers are dried and concentrated. The crude product is chromatographed (from hexane to 10% EtOAc in hexane) to give 630 mg (89%) of the desired compound as a colorless oil.

¹H NMR (200 MHz, CDCl₃), δ 7.23–7.16 (m, 5H), 4.94–4.91 (d, J=6, 1H), 4.43 (s, 2H), 3.57–3.30 (m, 8H), 2.54–2.10 (m, 2H), 1.89–1.56 (m, 8H), 1.12–1.10 (d, J=4, 2H), 0.90–0.65 (m, 32H), 0.03 to −0.01 (m, 12H); ¹³C NMR (200 MHz, CDCl₃), δ 137.85, 133.43, 130.42, 128.45, 127.76, 127.67, 81.58, 78.85, 76.60, 75.68, 73.44, 65.42, 38.63, 38.40, 37.07, 36.73, 36.37, 34.65, 26.25, 26.18, 25.37, 18.50, 18.35, 17.39, 15.85, 13.70, 12.94, 9.65, −3.49, −3.55, −3.89. Mass spectrum (ESI), m/z 665, 682 (m+NH₃).

c) Preparation of (2R,3R,4S,5Z,8S,9R,10R,11S,12S)-3,9-bis[[(1,1-dimethylethyl)dimethylsilyl]oxy]-11-hydroxy-2,4, 6,8,10,12-hexamethyl-13-(phenylmethoxy)-5-tridecenal.

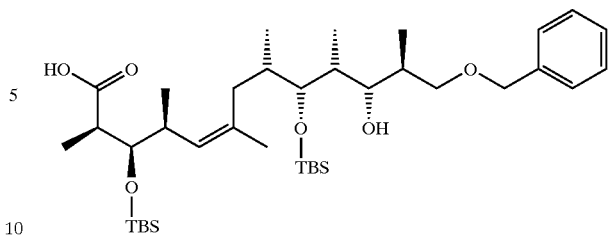

TEMPO (21 mg, 0.136 mmol, 0.2 eq) is added to a solution of (2S,3R,4S,5Z,8S,9R,10R,11S,12S)-3,9-bis[[(1, 1-dimethylethyl)dimethylsilyl]oxy]-2,4,6,8,10,12-hexamethyl-13-(phenylmethoxy)-5-tridecene-1,11-diol (450 mg, 0.68 mmol) in CH₂Cl₂ (4 mL) and stirred for 5 min at 23° C. BAIB (263 mg, 0.816 mmol, 1.2 eq) is added to the reaction mixture and stirred for 2 h. CH₂Cl₂ (7 mL) and saturated Na₂S₂O₃ are added to the mixture. The organic layer is separated, washed with brine and dried. The solvent is removed to give 438 mg of crude product. The crude product is used for the next step.

Mass spectrum (ESI), m/z 663, 680(m+NH₃).

d) Preparation of (2Z,4S,5S,6S,7Z,10S,11R,12R,13S,14S)-5,11-bis[[(1,1-dimethylethyl)dimethylsilyl]oxy]-13-hydroxy-4,6,8,10,12,14-hexamethyl-15-(phenylmethoxy)-2,7-pentadecadienoic acid methyl ester.

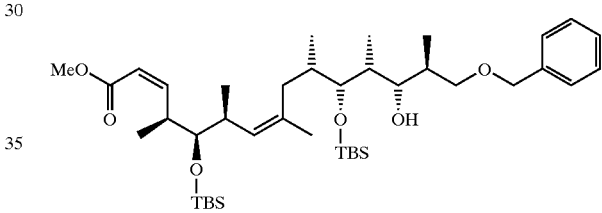

18-Crown-6 (349 mg, 1.32 mmol, 2 eq) is added to a solution of bis(2,2,2-trifluoroethyl) (methoxycarbonylmethyl)phosphonate (355 mg, 1.78 mmol, 2.7 eq) in toluene (7 mL) at 23° C. and stirred for 5 min. The mixture is cooled to −20° C. KHMDS (1.78 mmol, 2.7 eq, 0.5 M in toluene) is added dropwise and stirred for 30 min. The mixture is warmed to 0° C. and stirred for 30 min. Then the mixture is cooled to −20° C., a solution of crude (2R,3R,4S,5Z,8S,9R,10R,11S,12S)-3,9-bis[[(1,1-dimethylethyl)dimethylsilyl]oxy]-11-hydroxy-2,4,6,8,10, 12-hexamethyl-13-(phenylmethoxy)-5-tridecenal in toluene (3 mL) is added to the mixture and stirred for 5 min. The mixture is warmed to 0° C. and stirred for 4 h. Saturated NH₄Cl (15 mL) is added, and the resultant mixture is washed with brine, dried and concentrated. The crude product is chromatographed (10% EtOAc in hexane) to give 266 mg (two-step: 52%) of the desired compound as a colorless oil.

¹H NMR (200 MHz, CDCl₃), δ 7.26–7.19 (m, 5H), 6.33–6.26 (t, J=6, 1H), 5.64–5.60 (d, J=8, 1H), 4.86–4.83 (d, J=7, 1H), 4.44 (s, 2H), 3.59–3.24 (m, 11H), 2.27–2.06 (m, 2H), 1.88–1.48 (m, 8H), 0.94–0.60 (m, 32H), 0.02 to −0.01 (m, 12H); ¹³C NMR (200 MHz, CDCl₃), δ 166.48, 152.52, 137.85, 132.96, 130.15, 128.46, 127.76, 127.66, 118.47, 80.64, 78.81, 76.61, 75.90, 73.45, 50.86, 38.45, 37.90, 37.44, 36.33, 36.27, 34.58, 26.23, 23.14, 18.49, 18.45, 18.27, 18.22, 13.72, 13.12, 9.50, −3.36, −3.57, −3.62. Mass spectrum (ESI), m/z 719, 736 (m+NH₃).

e) Preparation of (2Z,4S,5S,6S,7Z,10S,11R,12R,13S,14S)-13-[(aminocarbonyl)oxy]-5,11-bis[[(1,1-dimethylethyl)dimethylsilyl]oxy]-4,6,8,10,12,14-hexamethyl-15-(phenylmethoxy)-2,7-pentadecadienoic acid methyl ester.

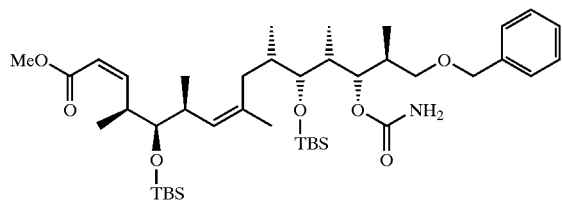

Trichloroacetyl isocyanate (106 mg, 0.56 mmol, 1.5 eq) is added to a solution of (2Z,4S,5S,6S,7Z,10S,11R,12R,13S,14S)-5,11-bis[[(1,1-dimethylethyl)dimethylsilyl]oxy]-13-hydroxy-4,6,8,10,12,14-hexamethyl-15-(phenylmethoxy)-2,7-pentadecadienoic acid methyl ester (266 mg, 0.37 mmol) in CH₂Cl₂ (5 mL) at 23° C. The mixture is stirred for 30 min. The solvent is removed. The residue is chromatographed (10% EtOAc in hexane) to give 208 mg (74%) of the desired compound as a white foam.

¹H NMR (200 MHz, CDCl₃), δ 7.24–7.19 (m, 5H), 6.33–6.26 (t, J=6, 1H), 5.64–5.61 (d, J=8, 1H), 4.84–4.81 (d, J=7, 1H), 4.66–4.63 (m, 1H), 4.48–4.40 (m, 4H), 3.59–3.16 (m, 8H), 2.30–1.82 (m, 4H), 1.56–1.51 (m, 6H), 0.94–0.57 (m, 32H), 0.04 to −0.01 (m, 12H); ¹³C NMR (200 MHz, CDCl₃), δ 166.51, 156.80, 152.49, 138.52, 132.86, 130.06, 128.30, 127.66, 127.48, 118.46, 80.58, 77.68, 76.91, 76.59, 73.24, 72.29, 50.89, 37.90, 37.45, 37.39, 36.28, 36.10, 34.83, 31.59, 26.20, 22.89, 22.66, 18.47, 18.29, 18.21, 14.75, 14.14, 12.97, 10.39, −3.37, −3.60, −3.64. Mass spectrum (ESI), m/z 762, 779 (m+NH₃).

f) Preparation of (2Z,4S,5S,6S,7Z,10S,11R,12R,13S,14S)-5,11-bis[[(1,1-dimethylethyl)dimethylsilyl]oxy]-4,6,8,10,12,14-hexamethyl-15-(phenylmethoxy)-2,7-pentadecadiene-1,13-diol-13-carbamate.

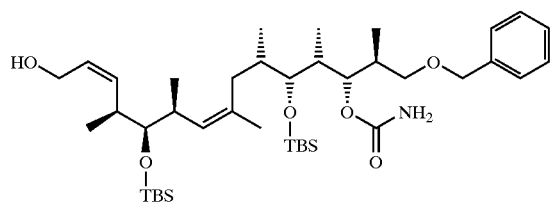

A solution of (2Z,4S,5S,6S,7Z,10S,11R,12R,13S,14S)-13-[(aminocarbonyl)oxy]-5,11-bis[[(1,1-dimethylethyl)dimethylsilyl]oxy]-4,6,8,10,12,14-hexamethyl-15-(phenylmethoxy)-2,7-pentadecadienoic acid methyl ester (208 mg, 0.27 mmol) in CH₂Cl₂ (4 mL) is treated with DIBAL-H (1.08 mmol, 4 eq, 1 N in hexane) at −78° C. The mixture is stirred for 2 h. Saturated Rochelle's salt solution is added to the mixture. The mixture is extracted with ether, washed with brine and dried over MgSO₄. The solvent is removed. The residue is chromatographed (10% to 20% EtOAc in hexane) to give 152 mg (77%) of the desired compound as a slightly yellow oil.

¹H NMR (200 MHz, CDCl₃), δ 7.28–7.20 (m, 5H), 5.53–5.45 (m, 1H), 4.94–4.90 (d, J=8, 1H), 4.71–4.42 (m, 4H), 4.08–4.03 (m, 2H), 3.48–3.18 (m, 4H), 2.61–1.57 (m, 12H), 0.94–0.63 (m, 32H), 0.02–0.0 (m, 12H); ¹³C NMR (200 MHz, CDCl₃), δ 157.40, 138.90, 135.02, 133.05, 128.93, 128.71, 128.10, 127.70, 81.22, 77.85, 73.69, 73.01, 59.37, 38.31, 37.56, 37.45, 37.38, 36.91, 36.52, 34.81, 32.00, 26.64, 23.16, 19.76, 18.91, 18.27, 15.09, 14.55, 12.79, 10.83, −2.64, −3.09, −3.21. Mass spectrum (ESI), m/z 734, 751 (m+NH₃).

g) Preparation of unsaturated (2Z,4S,5S,6S,7Z,10S,11R,12R,13S,14S)-13-[(aminocarbonyl)oxy]-5,11-bis[[(1,1-dimethylethyl)dimethylsilyl]oxy]-4,6,8,10,12,14-hexamethyl-15-(phenylmethoxy)-2,7-pentadecadienal.

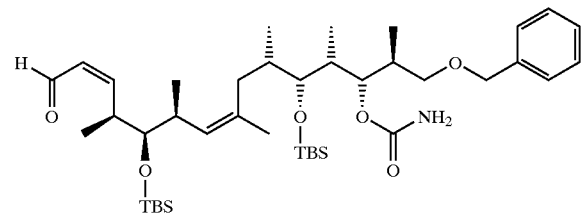

A solution of (2Z,4S,5S,6S,7Z,10S,11R,12R,12S,14S)-5,11-bis[[(1,1-dimethylethyl)dimethylsilyl] oxy]-4,6,8,10,12,14-hexamethyl-15-(phenylmethoxy)-2,7-pentadecadiene-1,13-diol-13-carbamate (198 mg, 0.37 mmol) in CH₂Cl₂ (2 mL) is added to a solution of Dess-Martin reagent (138 mg, 0.324 mmol, 1.2 eq) in CH₂Cl₂ (2 mL) at 23° C. The mixture is stirred for 1 h. Saturated Na₂S₂O₃ is added to the mixture. The organic layer is separated, washed with brine and dried over MgSO₄. The solvent is removed. The residue is chromatographed (10% EtOAc in hexane) to give 190 mg (95%) of the desired compound as a colorless oil. This aldehyde is used immediately. Mass spectrum (ESI), m/z 732, 751 (m+NH₃).

h) Preparation of (2R,3S,4R,7S,8Z,10S,11S,12S,13Z,16S,17R,18R,19S,20S)-19-[(aminocarbonyl)oxy]-3,11,17-tris[[(1,1-dimethylethyl)dimethylsilyl]oxy]-7-hydroxy-N-methoxy-N,2,4,10,12,14,16,18,20-nonamethyl-5-oxo-21-(phenylmethoxy)-8,13-heneicosadienamide.

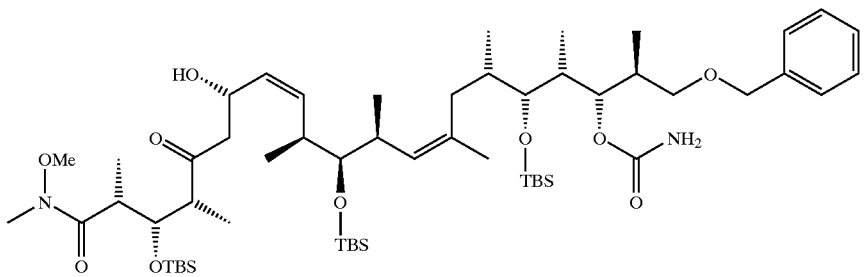

A solution of (+)-DIP-Cl (963 mg, 3.0 mmol, 11 eq) in ether (2 mL) is treated with fresh distilled Et$_3$N (320 mg, 3.16 mmol, 11.7 eq) at −5° C. and stirred for 30 min. A solution of (2R,3S,4R)-3-[[(1,1-dimethylethyl)dimethylsilyl]oxy]-N-methoxy-N-methyl-2,4-trimethyl-5-oxo-hexanamide (895 mg, 2.7 mmol, 10 eq) in ether (2 mL) is added through a cannula. The mixture is stirred for 2 h at −5° C. Then the mixture is cooled to −78° C. A solution of (2Z,4S,5S,6S,7Z,10S,11R,12R,13S,14S)-13-[(aminocarbonyl)oxy]-5,11-bis[[(1,1-dimethylethyl)dimethylsilyl]oxy]-4,6,8,10,12,14-hexamethyl-15-(phenylmethoxy)-2,7-pentadecadienal (190 mg, 0.26 mmol) in ether (2 mL) is added dropwise to the mixture and stirred for 3 h. The mixture is warmed to −20° C., MeOH (4 mL), phosphate buffer (pH=7.4, 4 mL) and H$_2$O$_2$ (30%, 4 mL) are added to quench the reaction and the resultant mixture is stirred for 2 h at −20° C. The organic layer is extracted with EtOAc, washed with brine and dried over MgSO$_4$. The solvent is removed. The crude product is chromatographed (20% EtOAc in hexane) to give 173 mg (60%) of the desired compound as a colorless oil.

$^1$H NMR (200 MHz, CDCl$_3$), δ 7.25–7.18 (m, 5H), 5.46–5.38 (m, 1H), 5.29–5.22(t, J=7, 1H), 5.00–4.97 (d, J=6, 1H), 4.74–4.44 (m, 4H), 4.35–4.27 (m, 2H), 4.25–4.22 (m, 1H), 3.66 (s, 3H), 3.66–2.73 (m, 7H), 2.73–2.38 (m, 6H), 2.21–1.56(m, 9H), 1.12–0.63 (m, 48H), 0.04 to −0.04 (m, 18H); $^{13}$C NMR (200 MHz, CDCl$_3$), δ 213.43, 175.88, 156.89, 138.55, 136.00, 132.09, 131.26, 129.67, 128.29, 127.66, 127.46, 80.66, 77.04, 76.61, 74.02, 73.26, 72.63, 64.92, 61.30, 60.40, 53.13, 49.08, 38.19, 37.62, 37.11, 36.19, 36.02, 34.59, 32.00, 26.26, 26.24, 26.01, 23.00, 19.76, 18.63, 18.49, 18.47, 18.18, 16.49, 14.95, 14.68, 12.34, 11.04, 10.45, −3.22, −3.29, −3.55, −3.87, −4.07, −4.42. Mass spectrum (ESI), m/z 1063.

i) Preparation of (2R,3S,4S,5S,7S,8Z,10S,11S,12S,13Z, 16S,17R,18R,19S,20S)-19-[(aminocarbonyl)oxy]-3,11,17-tris[[(1,1-dimethylethyl)dimethylsilyl]oxy]-5,7-dihydroxy-N-methoxy-N, 2,4,10,12,14,16,18,20-nonamethyl-21-(phenylmethoxy)-8, 13-heneicosadienamide.

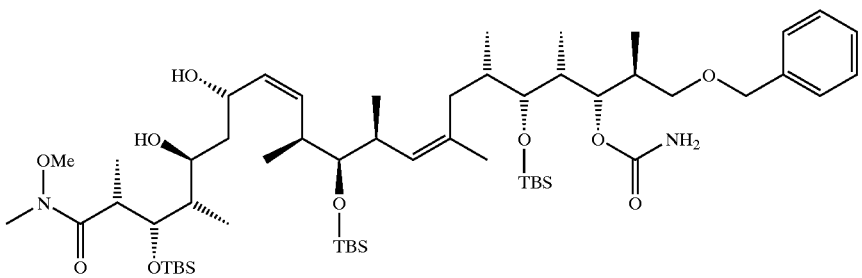

A solution of tetramethylammonium triacetoxyborohydride (263 mg, 1 mmol, 10 eq) in MeCN/HOAc(1:1, 1.1 mL) is stirred for 1 h at 23° C. and cooled to −30° C. A solution of (2R,3S,4R,7S,8Z,10S,11S,12S,13Z,16S,17R,18R,19S, 20S)-19-[(aminocarbonyl)oxy]-3,11,17-tris[[(1,1-dimethylethyl)dimethylsilyl]oxy]-7-hydroxy-N-methoxy-N,2,4,10,12,14,16,18,20-nonamethyl-5-oxo-21-(phenylmethoxy)-8,13-heneicosadienamide (103 mg, 0.1 mmol) in MeCN (1 mL) is added dropwise. The mixture is stirred for 14 h at −30° C. Saturated Rochelle's salt solution is added and the resultant stirred for 30 min. Then the mixture is warmed to 23° C. CH$_2$Cl$_2$ (5 mL) is added to the mixture. The organic layer is separated, washed with brine and dried over MgSO$_4$. The solvent is removed. The crude product is chromatographed (20% EtOAc in hexane) to give 80 mg (80%) of the desired compound as a colorless oil.

$^1$H NMR (200 MHz, CDCl$_3$), δ 7.26–7.21 (m, 5H), 5.42–5.29 (m, 2H), 4.96–4.92 (d, J=8, 1H), 4.67–4.41 (m, 6H), 4.12–4.07 (m, 1H), 3.67 (s, 3H), 3.46–3.05 (m, 8H), 2.64–1.87 (m, 6H), 2.21–1.53(m, 10H), 1.26–0.62 (m, 48H), 0.06 to −0.06 (m, 18H); $^{13}$C NMR (200 MHz, CDCl$_3$), δ 175.75, 156.80, 138.51, 136.13, 132.13, 131.06, 129.91, 128.67, 127.36, 127.49, 80.63, 77.09, 76.59, 74.45, 73.89, 73.25, 72.71, 64.88, 61.38, 60.37, 53.14, 49.10, 38.21, 37.59, 37.13, 36.20, 36.05, 34.61, 32.02, 26.29, 26.25, 26.04, 23.03, 19.76, 18.71, 18.51, 18.46, 18.15, 16.48, 14.96, 14.62, 12.37, 11.00, 10.43, −3.30, −3.33, −3.46, −3.82. Mass spectrum (ESI), m/z 1065.

j) Preparation of (2R,3S,4S,5S,7S,8Z,10S,11S,12S,13Z, 16S,17R,18S,19S,20S)-19-[(aminocarbonyl)oxy]-3,5,7,11, 17-pentahydroxy-2,3,4,10,12,14,16,18,20-nonamethyl-21-(phenylmethoxy)-8,13-heneicosadienoic acid 6-lactone.

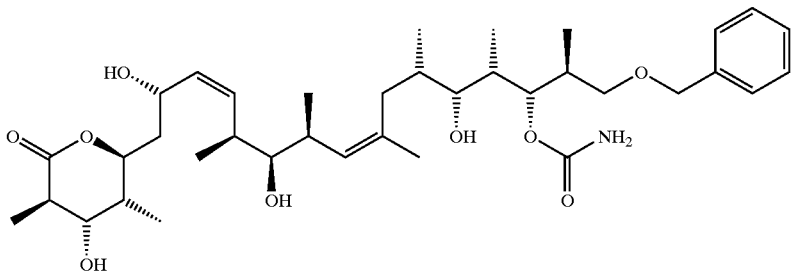

4 N HCl (0.5 mL) is added dropwise to a stirred solution of (2R,3S,4S,5S,7S,8Z,10S,11S,12S,13Z,16S,17R,18R,19S,20S)-19-[(aminocarbonyl)oxy]-3,11,17-tris[[(1,1-dimethylethyl)dimethylsilyl]oxy]-5,7-dihydroxy-N-methoxy-N, 2,4,10,12,14,16,18,20-nonamethyl-21-(phenylmethoxy)-8,13-heneicosadienamide (80 mg, 0.075 mmol) in isopropanol (0.5 mL) at 0° C. After being warmed to 23° C., the mixture is stirred for 40 h. The mixture is then cooled to 0° C. and saturated NaHCO₃ is added to neutralize the mixture to pH=7. The solvent is removed. The crude product is purified by HPLC to give 5 mg of the desired compound (15%) as a white powder.

$^1$H NMR (500 MHz, CDCl₃), δ 7.34–7.24 (m, 5H), 5.56–5.48 (m, 1H), 5.45–5.38(t, J=6, 1H), 5.23–5.14 (d, J=7, 1H), 4.84–4.70 (m, 3H), 4.69–4.62 (m, 1H), 4.52–4.44(m, 2H), 3.72 (b, 1H), 3.51–3.5.47 (m, 1H), 3.37–3.28 (m, 2H), 3.25–3.20 (m, 1H), 2.90–2.79 (m, 1H), 2.75–2.60 (m, 2H), 2.60–2.20 (m, 2H), 2.17–2.12 (m, 1H), 2.08–1.90 (m, 5H), 1.89–1.82 (m, 1H), 1.75–1.54 (m, 7H), 1.37–1.32 (m, 3H), 1.12–0.91 (m, 15H), 0.88–0.82 (m, 3H); $^{13}$C NMR (200 MHz, CDCl₃), δ 173.98, 157.20, 138.45, 134.45, 133.60, 132.82, 129.516, 128.32, 127.68, 127.51, 79.01, 77.46, 76.75, 75.75, 73.25, 73.17, 72.54, 64.45, 43.12, 40.93, 37.17, 36.48, 36.40, 36.16, 35.63, 35.48, 32.60, 23.35, 18.36, 15.92, 15.59, 14.45, 13.26, 12.59, 8.93. HRMS calcd for C₃₇H₆₀NO₉ (M+H)+662.4268, found 662.4284.

EXAMPLE 2

Synthesis of (2R,3S,4R,5S,7S,8Z)-13-[[(2R,3S,4S,5S,6S,7Z)-5-[(aminocarbonyl)oxy]-3-hydroxy-2,4,6-trimethyl-1-oxo-7,9-decadienyl]methylamino]-3,5,7,11-tetrahydroxy-2,4,10,12-tetramethyl-8-tridecenoic Acid 6-lactone.

a) Preparation of 1,2,4-trideoxy-3-O-[(1,1-dimethylethyl)dimethylsilyl]-5-O-[(4-methoxyphenyl)methyl]-2,4-dimethyl-1-(methylamino)-L-arabinitol.

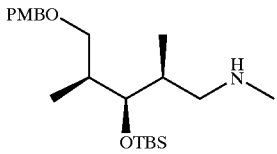

A solution of 2,4-dideoxy-3-O-[(1,1-dimethylethyl)dimethylsilyl]-5-O-[(4-methoxyphenyl) methyl]-2,4-dimethyl-L-arabinose (2.8 g, 7.37 mmol) in THF (10 mL) is added slowly to a stirred solution of methylamine (14.7 mL, 29.5 mmol) in THF at room temperature. After being stirred at room temperature for 20 min, sodium triacetoxyborohydride (2.3 g, 11.05 mmol), followed by acetic acid (10 drops) are added at room temperature. After being stirred at room temperature overnight, the reaction mixture is diluted with EtOAc (100 mL), and washed with saturated NaHCO₃ (2×30 mL), H₂O (50 mL), brine (50 mL) and dried over Na₂SO₄. After removal of the solvent in vacuo, the residue is chromatographed on silica gel with MeOH/CH₂Cl₂ (1/99) to give the desired compound (1.54 g, 52.9%) as a pale viscous oil.

$^1$H NMR (CDCl₃, 500 MHz), δ 7.25 (d, J=8.24 Hz, 2H), 6.87 (d, J=8.70 Hz, 2H), 4.42 (dd, J=18.76, 11.60 Hz, 2H), 3.80 (s, 3H), 3.62 (dd, J=6.11, 2.45 Hz, 1H), 3.51 (dd, J=9.16, 5.04 Hz, 1H), 3.24 (dd, J=9.00, 7.47 Hz, 1H), 2.53 (dd, J=11.59, 6.86 Hz, 1H), 2.40 (m, 1H), 2.63 (s, 3H), 1.96 (m, 1H), 1.80 (m, 1H), 0.98 (d, J=7.02 Hz, 1H), 0.95 (d, J=6.86 Hz, 3H), 0.88 (s, 9H), 0.87 (d, J=6.80, 3H), 0.04 (s, 3H), 0.03 (s, 3H); $^{13}$C NMR (CDCl₃, 125 MHz), δ 159.1, 130.8, 129.2, 129.1, 113.7, 75.4, 72.8, 72.7, 56.6, 55.3, 38.1, 36.4, 36.1, 26.1, 26.0, 18.4, 15.0, 13.0, −4.0, −4.1.

b) Preparation of 2,4-dideoxy-3,5-O-[(4-methoxyphenyl)methylene]-2,4-dimethyl-L-arabinitol.

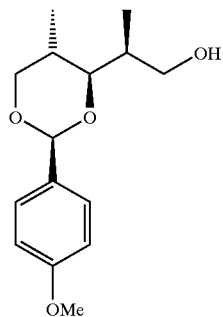

A suspension of LiAlH₄ (5.33 g, 37.95 mmol) in THF (250 mL) is cooled to −74° C. 2,4-dideoxy-3,5-O-[(4-methoxyphenyl)methylene]-2,4-dimethyl-L-arabinose (23.2 g, 87.88 mmol) in 50 mL of THF is added dropwise over 30 min at −70° C. to −74° C. The resultant solution is stirred at that temperature range for 1.5 h and then warmed to 0° C. The reaction is quenched with 6 mL of water in 90 mL of THF, 6 mL of 15% NaOH, and 30 mL of water at 0° C. to 10° C. The organic phase is separated and the aqueous phase is extracted with ethyl acetate (3×200 mL). The combined organic layers are washed with water (2×300 mL), brine (2×300 mL), dried over Na₂SO₄ and concentrated. The desired product (24.6 g, 105%) is obtained as a clear oil.

$^1$H NMR (300 MHz, CDCL₃), δ 7.38 (d, J=8.7 Hz, 2H), 6.88 (d, J=8.7 Hz, 2H), 5.48 (s, 1H), 4.11 (m, 1H), 3.8–3.65

(m, 3H), 3.80 (s, 3H), 3.52 (apparent t, J=11.3 Hz, 1H), 2.17–1.92 (m, 3H), 1.05 (d, J=7.16 Hz, 3H), 0.77 (d, J=6.8 Hz, 3H); $^{13}$C NMR (CDCl$_3$, 75 MHz), δ 159.9, 131.1, 127.3, 121.3, 113.6, 101.1, 84.7, 73.2, 66.8, 55.3, 35.6, 30.4, 11.9, 9.72.

c) Preparation of 2,4-dideoxy-1-O-[(1,1-dimethylethyl) dimethylsilyl]-3,5-O-[(4-methoxyphenyl)methylene]-2,4-dimethyl-L-arabinitol.

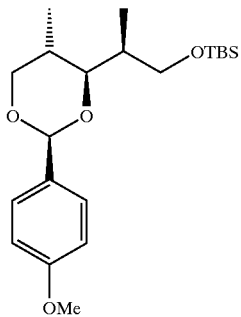

A solution of 2,4-dideoxy-3,5-O-[(4-methoxyphenyl) methylene]-2,4-dimethyl-L-arabinitol (24.5 g, 92.48 mmol), 2,6-lutidine (17.84 g, 166.46 mmol) and methylene chloride (400 mL) is cooled to −20° C. TBSOTf (36.67 g, 138.72 mmol) is added over 30 min. After stirring for an additional 2 h at 0° C., the mixture is diluted with ether (400 mL), washed with aqueous NaHSO$_4$, brine, and concentrated. Flash chromatography affords the desired product (30 g, 86%) as a white solid.

$^1$H NMR (300 MHz, CDCl$_3$), δ 7.37 d, J=8.7 Hz, 2H), 6.85 (d, J=8.7 Hz, 2H), 5.38 (s, 1H), 4.10 (dd, J=11.3, 4.9, 1H), 3.77 (s, 3H), 3.66–3.60 (m, 2H), 3.51–3.44 (m, 2H), 2.07–1.88 (m, 2H), 0.90 (d, J=7.54 Hz, 3H), 0.87 (s, 9H), 0.72 (d, J=6.8 Hz, 3H), 0.004 (s, 6H); $^{13}$C NMR (CDCl$_3$, 75 MHz), δ 159.7, 131.6, 127.3, 121.3, 113.4, 100.9, 81.4, 73.3, 64.8, 55.3, 36.6, 30.3, 26.0, 18.3, 12.1, 9.73, −5.33, −5.36.

d) Preparation of 2,4-dideoxy-1-O-[(1,1-dimethylethyl) dimethylsilyl]-3-O-[(4-methoxyphenyl)methyl]-2,4-dimethyl-L-arabinitol.

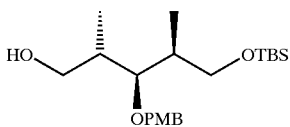

A solution of 2,4-dideoxy-1-O-[(1,1-dimethylethyl) dimethylsilyl]-3,5-O-[(4-methoxyphenyl)methylene]-2,4-dimethyl-L-arabinitol (29 g, 76.3 mmol) and methylene chloride (500 mL) is cooled to −73° C., and DIBAL (1.0 M in hexane, 763 mL, 763 mmol) is added dropwise over 1.5 h. After 1 additional hour at −78° C., the reaction mixture is warmed to 0° C. The reaction is quenched very slowly with saturated Rochelle's salt. The solution is separated. The aqueous phase is extracted with ethyl acetate (2×200 mL). The combined organic phase is washed with brine (2×200 mL), and concentrated. Flash chromatography affords the desired product (24.5 g, 84%) as a clear oil.

$^1$H NMR (300 MHz, CDCl$_3$), δ 7.22 (d, J=7.9 Hz, 2H), 6.82 (d, J=8.7 Hz, 2H), 4.50(dd, J=26.4, 10.9, 2H), 3.74 (s, 3H), 3.59–3.44 (m, 5H), 2.75 (apparent t, J=5.80, 1H), 1.92–1.76 (m, 1H), 0.87–0.84 (m, 3H), 0.85 (s, 9H), 0.825 (d, J=1.9 Hz, 3H), 0.00 (s, 6H); $^{13}$C NMR (CDCl$_3$, 75 MHz), δ 159.3, 130.7, 129.5, 113.9, 83.6, 74.6, 67.0, 65.6, 55.3, 38.6, 37.8, 25.9, 18.2, 14.9, 10.7, −5.31, −5.38.

e) Preparation of 2,4-dideoxy-5-O-[(1,1-dimethylethyl) dimethylsilyl]-3-O-[(4-methoxyphenyl)methyl]-2,4-dimethyl-L-lyxose.

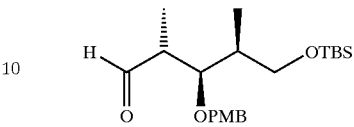

A solution of 2,4-dideoxy-1-O-[(1,1-dimethylethyl) dimethylsilyl]-3-O-[(4-methoxyphenyl)methyl]-2,4-dimethyl-L-arabinitol (10.77 g, 28.19 mmol), DMSO (30 mL), NEt$_3$ (11.39 g, 112.76 mmol) and methylene chloride is cooled to −10° C., and treated with SO$_3$-Pyr (13.45 g, 84.58 mmol)in DMSO (60 mL) over 40 min. After additional 2 h at 0° C., the mixture is diluted with ether (300 mL), washed with 1 M aqueous NaHSO$_4$ (100 mL), brine (100 mL), and concentrated. Flash chromatography (5% ethyl acetate in hexane) gives the desired compound (9 g, 84%) as a colorless oil.

$^1$H NMR (300 MHz, CDCl$_3$), δ 9.70 (d, J=2.26 Hz, 1H), ⌷⌶d, J=8.3 Hz, 2H), 6.81 (d, J=8.3 Hz, 2H), 4.45 (dd, J=20.7, 10.9, 2H), 3.79 (dd, J=7.91, 3.76, 1H), 3.74 (s, 3H), 3.56–3.44 (m, 2H), 2.71–2.59 (m, 1H), 1.89–1.76 (m, 1H), 0.98 (d, J=7.16 Hz, 3H), 0.86 (d, J=8 Hz, 3H), 0.85 (s, 9H), 0.002 (s, 6H); $^{13}$C NMR (CDCl$_3$, 75 MHz), δ 204.9, 159.2, 130.7, 129.3, 113.8, 79.8, 74.0, 65.0, 55.3, 49.3, 38.4, 25.9, 18.2, 11.23, 10.98, −5.35, −5.41.

f) Preparation of the (1,1-dimethylethyl)[[(2S,3S,4S,5Z)-3-[(4-methoxyphenyl)methoxy]-2,4-dimethyl-5,7-octadienyl] oxy]dimethyl-silane.

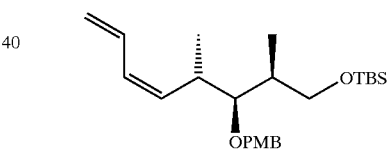

A suspension consisting of CrCl$_2$ (12.93 g, 105.38 mmol) and 700 mL anhydrous THF is cooled to 0° C. 2,4-dideoxy-5-O-[(1,1-dimethylethyl)dimethylsilyl]-3-O-[(4-methoxyphenyl)methyl]-2,4-dimethyl-L-lyxose (8.9 g, 23.42 mmol) in 40 mL THF is added dropwise. (1-Bromoallyl) trimethylsilane (22.61, 117.1 mmol) is added neat. After 3 h at room temperature, the reaction mixture is cooled to 10° C. Methanol (270 mL) and 6 N aqueous KOH (550 mL) are added in sequence, keeping the reaction temperature less than 20° C. during the addition. The mixture is stirred overnight at room temperature. The organic layer is separated. The aqueous layer is extracted with ether (3×400 mL). The combined organic phase is washed with brine, dried over NaSO$_4$, and concentrated. Flash chromatography gives the desired compound (6.74 g, 71.2%) as a clear oil.

$^1$H NMR (300 MHz, CDCl$_3$), δ 7.20 (d, J=8.7 Hz, 2H), 6.81 (d, J=8.7 Hz, 2H), 6.61 (dt, J=16.96, 10.92 Hz, 1H), 5.97 (t, J=10.92 Hz, 1H), 5.46 (t, J=10.55 Hz, 1H), 5.09 (dd, J=33.5, 17.0 Hz, 2H), 4.45 (dd, J=27.5, 9.4 Hz, 2H), 3.76 (s,

3H), 3.51–3.32 (m, 3H), 2.97–2.82 (m, 1H), 1.85–1.76 (m, 1H), 0.97 (d, J=7.16 Hz, 3H), 0.88 (d, J=7.9 Hz, 3H), 0.87 (s, 9H), 0.001 (s, 6H); $^{13}$C NMR (CDCl3, 75 MHz), δ 161.79, 138.13, 134.77, 131.52, 131.07, 119.22, 115.79, 85.2, 76.6, 67.8, 57.5, 40.9, 37.8, 28.2, 20.6, 13.8, −3.13, −3.15.

g) Preparation of (2S,3S,4S,5Z)-3-[(4-methoxyphenyl)methoxy]-2,4-dimethyl-5,7-octadien-1-ol.

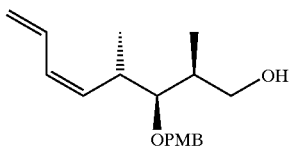

A solution of (1,1-dimethylethyl)[[(2S,3S,4S,5Z)-3-[(4-methoxyphenyl)methoxy]-2,4-dimethyl-5,7-octadienyl]oxy]dimethylsilane (6.74 g, 16.68 mmol) and THF (70 mL) is cooled to 0° C. 4 N aqueous HCl (70 mL) is added to the solution dropwise to maintain the reaction temperature at less than 5° C. The mixture is stirred at 0° C. for 1 h. The mixture is quenched by the addition of saturated aqueous $NaCO_3$. The organic phase is separated. The aqueous phase is extracted with ethyl acetate (5×100 mL). The combined organic phase is washed with brine, dried over $NaSO_4$ and concentrated. Flash chromatography gives the desired compound (4.17 g, 86%) as a clear oil.

$^1$H NMR (300 MHz, CDCl3), δ 7.25 (d, J=8.7 Hz, 2H), 6.86 (d, J=8.7 Hz, 2H), 6.67 (dt, J=21.5, 11.3 Hz, 1H), 6.04 (t, J=11.31 Hz, 1H), 5.55 (t, J=10.55 Hz, 1H), 5.16 (dd, J=34.3, 16.95 Hz, 2H), 4.53 (dd, J=36.6, 10.9, 2H), 3.80 (s, 3H), 3.65–3.49 (m, 2H), 3.40 (dd, J=5.7, 3.8 Hz, 1H), 3.05–2.95 (m, 1H), 2.03–1.90 (m, 1H), 1.83 (t, J=5.7 Hz, 1H), 1.02 (d, J=6.8 Hz, 3H), 0.95 (d, J=6.8 Hz, 3H); $^{13}$C NMR (CDCl$_3$, 75 MHz), δ 159.2, 135.4, 132.5, 130.8, 129.6, 129.1, 117.5, 113.7, 84.2, 73.9, 66.1, 55.3, 37.7, 35.1, 18.6, 11.5.

h) Preparation of (2R,3S,4S,5Z)-3-[(4-methoxyphenyl)methoxy]-2,4-dimethyl-5,7-octadienal.

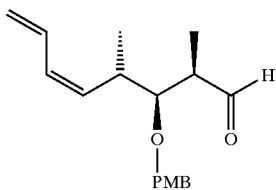

A solution of (2S,3S,4S,5Z)-3-[(4-methoxyphenyl)methoxy]-2,4-dimethyl-5,7-octadien-1-ol (2.0 g, 6.9 mmol), DMSO (2.1 mL), NEt$_3$ (2.79 g, 27.59 mmol) and methylene chloride (20 mL) is cooled to 0° C., and is treated with SO$_3$-Pyr (3.29 g, 20.69 mmol) and DMSO (8 mL) over 10 min. After additional 2 h at 0° C., the mixture is diluted with ether (200 mL), washed with 1 M aqueous NaHSO$_4$ (100 mL), brine (100 mL), and concentrated. Flash chromatography (1% to 10% ethyl acetate in hexane) gives the desired compound (1.95 g, 98.2%) as a colorless oil.

$^1$H NMR (300 MHz, CDCl$_3$), δ 9.69 (d, J=1.1 Hz, 1H), ☐☐☐d, J=8.7 Hz, 2H), 6.86 (d, J=8.7 Hz, 2H), 6.55 (dt, J=17.0, 10.2 Hz, 1H), 6.05 (t, J=10.9 Hz, 1H), 5.45 (t, J=10.55 Hz, 1H), 5.16 (dd, J=30.9, 16.95 Hz, 2H), 4.475 (dd, J=18.5, 10.9, 2H), 3.80 (s, 3H), 3.71 (t, J=4.9 Hz, 1H), 3.03–2.90 (m, 1H), 2.64–2.55 (m, 1H), 1.16 (d, J=7.2 Hz, 3H), 1.06 (d, J=6.9 Hz, 3H); $^{13}$C NMR (CDCl$_3$, 75 MHz), δ 204.2, 159.2, 133.8, 132.1, 130.3, 130.1, 129.4, 118.1, 113.7, 81.9, 73.6, 55.3, 49.5, 35.5, 18.3, 9.2.

i) Preparation of (4R)-3-[(2R,3S,4S,5S,6S,7Z)-3-hydroxy-5-[(4-methoxyphenyl)methoxy]-2,4,6-trimethyl-1-oxo-7,9-decadienyl]-4-(phenylmethyl)-2-oxazolidinone.

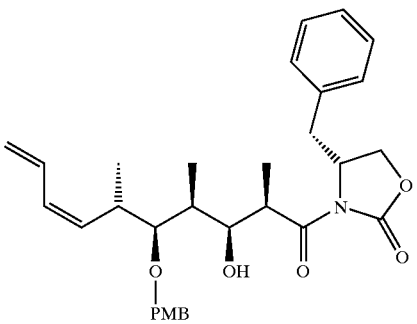

A solution of (R)-4-benzyl-3-propionyl-2-oxazolidinone (2.18 g, 9.34 mmol) and methylene chloride (15 mL) is cooled to −20° C. (n-Bu)$_2$BOTf (1.0 M in DCM, 8.7 mL, 8.7 mmol) is introduced dropwise. The reaction is allowed to warm to 0° C. NEt$_3$ (1.15 g, 11.34 mmol) is added and the mixture is stirred at 0° C. for 1 h, then cooled to −78° C. A solution of (2R,3S,4S,5Z)-3-[(4-methoxyphenyl)methoxy]-2,4-dimethyl-5,7-octadienal (1.95 g, 6.77 mmol) in DCM (10 mL) is added dropwise at −70° C. for 10 min. After 1 h at −74° C., the mixture is warmed to 0° C. The reaction is quenched with pH 7 buffer (15 mL). The mixture is slowly treated with a solution of 30% H$_2$O$_2$ in MeOH (1:2, 15 mL) at 0° C., stirred for 40 min at room temperature, and concentrated. The residue is extracted with ethyl acetate (3×100 mL). The combined organic phase is washed with saturated aqueous NaHCO$_3$, brine, and concentrated. Flash chromatography gives the desired compound (3.4 g, 96.4%) as a clear oil.

$^1$H NMR (300 MHz, CDCl$_3$), δ 7.38–7.16 (m, 7H), 6.82 (d, J=8.7 Hz, 2H), 6.69 (dt, J=17.0, 10.2 Hz, 1H), 6.06 (t, J=11.3 Hz, 1H), 5.50 (t, J=10.55 Hz, 1H), 5.17 (dd, J=30.1, 16.95, Hz, 2H), 4.53 (dd, J=98.7, 10.9, 2H), 4.63–4.56 (m, 1H), 4.23–4.10 (m, 2H), 4.02–3.96 (m, 1H), 3.83 (t, J=6.4 Hz, 1H), 3.78 (s, 3H), 3.38–3.33(m, 1H), 3.25–3.15 (m, 2H), 3.07–2.95 (m, 1H), 2.74 (dd, J=13.6, 9.8 Hz, 1H), 1.84–1.73 (m, 1H), 1.29 (d, J=7.2 Hz, 3H), 1.02 (d, J=6.8 Hz, 3H), 0.98 (d, J=6.8 Hz, 3H); $^{13}$C NMR (CDCl$_3$, 75 MHz), δ 176.8, 159.0, 152.7, 135.6, 135.1, 132.5, 130.7, 129.5, 129.4, 129.3, 128.9, 127.4, 117.7, 113.6, 86.3, 74.3, 73.8, 66.0, 55.3, 55.0, 40.6, 37.8, 37.7, 35.8, 18.14, 13.28.

j) Preparation of ((4R)-3-[(2R,3S,4R,5S,6S,7Z)-3-[[(1,1-dimethylethyl)dimethylsilyl]oxy]-5-[(4-methoxyphenyl)methoxy]-2,4,6-trimethyl-1-oxo-7,9-decadienyl]-4-(phenylmethyl)-2-oxazolidinone.

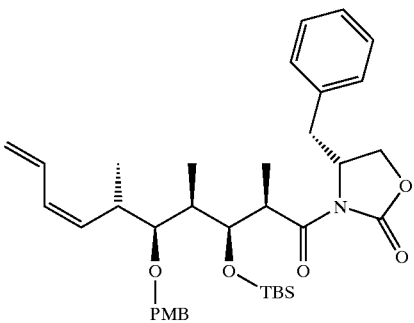

A solution of (4R)-3-[(2R,3S,4S,5S,6S,7Z)-3-hydroxy-5-[(4-methoxyphenyl)methoxy]-2,4,6-trimethyl-1-oxo-7,9-decadienyl]-4-(phenylmethyl)-2-oxazolidinone (3.4 g, 6.53 mmol), 2,6-lutidine (3.5 g, 32.65 mmol) and methylene chloride (100 mL) is cooled to 0° C. TBSOTf (7.12 g, 26.94 mmol) is added over 30 min and the resultant mixture is allowed to react overnight at 0° C. The mixture is diluted with ether (300 mL), washed with aqueous NaHSO$_4$, brine, and concentrated. Flash chromatography affords the desired compound (3.6 g, 87%) as an oil.

$^1$H NMR (300 MHz, CDCl$_3$), δ 7.25–7.05 (m, 7H), 6.74 (d, J=8.7 Hz, 2H), 6.58 (dt, J=16.5, 10.2 Hz, 1H), 5.86 (t, J=11.3 Hz, 1H), 5.49 (t, J=10.55 Hz, 1H), 5.10–5.01(m, 3H), 4.44–4.38 (m, 1H), 4.41 (s, 2H), 4.00–3.87 (m, 4H), 3.69 (s, 3H), 3.26 (dd, J=7.5, 3 Hz, 1H), 2.96–2.84 (m, 1H), 2.59 (dd, J=13.6, 9.8 Hz, 1H), 1.56–1.46 (m, 1H), 1.13(d, J=6.4 Hz, 3H), 1.01 (d, J=7.2 Hz, 3H), 0.92 (d, J=7.2 Hz, 3H), 0.86 (s, 9H), 0.035 (d, J=6.4 Hz, 6H); $^{13}$C NMR (CDCl$_3$, 75 MHz), δ 175.7, 158.9, 152.8, 135.4, 134.3, 133.1, 131.3, 129.5, 129.4, 129.0, 128.9, 127.3, 116.8, 113.6, 82.9, 74.5, 73.6, 65.9, 55.5, 55.3, 43.1, 42.1, 37.7, 35.6, 26.3, 25.7, 19.1, 18.5, 14.9, 10.27, −3.4, −3.6.

k) Preparation of (2R,3S,4R,5S,6S,7Z)-3-[[(1,1-dimethylethyl)dimethylsilyl]oxy]-5-[(4-methoxyphenyl)methoxy]-2,4,6-trimethyl-7,9-decadienoic acid.

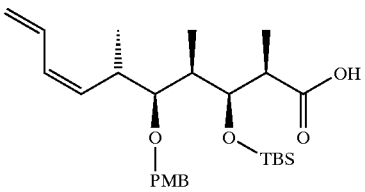

A solution of (4R)-3-[(2R,3S,4R,5S,6S,7Z)-3-[[(1,1-dimethylethyl)dimethylsilyl]oxy]-5-[(4-methoxyphenyl)methoxy]-2,4,6-trimethyl-1-oxo-7,9-decadienyl]-4-(phenylmethyl)-2-oxazolidinone), THF (15 mL) and water (5 mL) is cooled to 10° C. Hydrogen peroxide (50%, 20 mL) is added dropwise, followed by the addition of LiOH (0.575 g). The mixture is stored at 10° C. overnight. The reaction is quenched with the addition of saturated aqueous Na$_2$SO$_3$. The mixture is acidified by the addition aqueous HCl (12 M) to pH 1, then is extracted with ether. The combined organic phase is washed with brine, dried over Na2SO4, and concentrated. Flash chromatography gives the desired compound (1.34 g, 83%) as a white solid.

δ 7.26 (d, J=8.7, 2H), 6.85 (d, J=8.7 Hz, 2H), 6.69 (dt, J=17.0, 10.9 Hz, 1H), 6.02 (t, J=11.3 Hz, 1H), 5.50 (t, J=10.55 Hz, 1H), 5.21 (d, J=16.5 Hz, 1H), 5.12 (d, J=10.2 Hz, 1H), 4.50 (dd, J=29.4, 10.2 Hz, 2H), 4.07 (t, J=4.5 Hz, 1H), 3.79 (s, 3H), 3.25 (t, J=5.3 Hz, 1H), 3.05–2.94 (m, 1H), 2.74–2.65 (m, 1H), 1.90–1.79 (m, 1H), 1.11 (d, J=7.2 Hz, 3H), 1.06 (d, J=6.8 Hz, 3H), 1.00 (d, J=6.8 Hz, 3H), 0.93 (s, 9H), 0.10 (d, J=7.9 Hz, 6H); $^{13}$C NMR (CDCl$_3$, 75 MHz), δ 238.3, 159.1, 134.4, 132.3, 130.8, 129.5, 117.7, 113.7, 83.3, 74.6, 74.1, 55.3, 43.5, 40.3, 35.5, 26.0, 18.5, 18.3, 11.6, 10.4, −4.05.

l) Preparation of 1,2,4-trideoxy-3-O-[(1,1-dimethylethyl)dimethylsilyl]-1-[[(2R,3S,4R,5S,6S,7Z)-3-[[(1,1-dimethylethyl)dimethylsilyl]oxy]-5-[(4-methoxyphenyl)methoxy]-2,4,6-trimethyl-1-oxo-7,9-decadienyl]methylamino]-5-O-[(4-methoxyphenyl)methyl]-2,4-dimethyl-L-arabinitol.

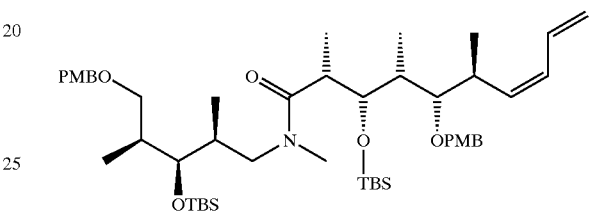

To a solution of 1,2,4-trideoxy-3-O-[(1,1-dimethylethyl)dimethylsilyl]-5-O-[(4-methoxyphenyl)methyl]-2,4-dimethyl-1-(methylamino)-L-arabinitol (1.23 g, 3.1 mmol) and (2R,3S,4R,5S,6S,7Z)-3-[[(1,1-dimethylethyl)dimethylsilyl]oxy]-5-[(4-methoxyphenyl)methoxy]-2,4,6-trimethyl-7,9-decadienoic acid (1.14 g, 2.4 mmol) in DMF (20 mL) at room temperature, benzotriazol-1-yl-oxyl-tris(dimethyamino)phosphonium hexafluorophosphate (BOP) (2.12 g, 4.8 mmol) and DIEA (1.86 g, 14.4 mmol) are added. After being stirred at room temperature overnight, the reaction mixture is purified by column chromatography on silica gel with hexane/EtOAc (90/10) to give the desired product (1.93 g, 94.5%) as a pale viscous oil.

$^1$H NMR (CDCl$_3$, 300 MHz), δ 7.22–7.17 (m, 4H), 6.83–6.76 (m, 4H), 6.70–6.59 (m, 1H), 5.96 (t, J=10.20 Hz, 1H), 5.58–5.45 (m, 1H), 5.16–5.05 (m, 2H), 4.57–4.46 (m, 1H), 4.35–4.34 (m, 2H), 4.16 (dd, J=9.04, 4.90 Hz, 1H), 3.75(s, 3H), 3.74 (s, 3H), 3.54 (t, J=5.65 Hz, 1H), 3.47–3.39 (m, 3H), 3.25–3.17 (m, 2H), 3.14–3.03 (m, 1H), 3.00–2.90 (m, 2H), 2.55 (s, 3H), 1.94–1.81 (m, 2H), 1.78–1.73 (m, 1H), 1.06 (t, J=6.03 Hz, 3H), 0.99 (d, J=7.16 Hz, 3H), 0.95–0.88 (m, 12H), 0.85–0.81 (m, 12H), 0.72 (d, J=6.78 Hz, 3H), 0.11 (s, 3H), 0.06 (s, 3H), 0.00 (s, 3H), −0.04 (s, 3H); $^{13}$C NMR (CDCl$_3$, 300 MHz), δ 176.3, 159.0, 158.9, 135.1, 133.2, 131.3, 130.9, 129.3, 129.2, 129.1, 116.9, 113.7, 113.5, 81.8, 75.8, 74.4, 73.7, 72.6, 72.6, 55.3, 40.9, 38.6, 38.5, 35.8, 35.7, 34.9, 29.7, 26.3, 26.1, 26.0, 18.5, 18.4, 18.4, 16.1, 15.0, 12.5, 8.6, −3.7, −3.7, −3.9, −4.2.

m) Preparation of 1,2,4-trideoxy-3-O-[(1,1-dimethylethyl)dimethylsilyl]-1-[[(2R,3S,4R,5S,6S,7Z)-3-[[(1,1-dimethylethyl)dimethylsilyl]oxy]-5-hydroxy-2,4,6-trimethyl-1-oxo-7,9-decadienyl]methylamino]-2,4-dimethyl-L-arabinitol.

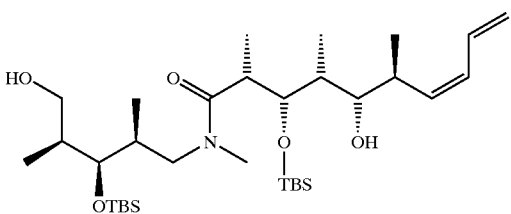

To a solution consisting of 1,2,4-trideoxy-3-O-[(1,1-dimethylethyl)dimethylsilyl]-1-[[(2R,3S,4R,5S,6S,7Z)-3-[[(1,1-dimethylethyl)dimethylsilyl]oxy]-5-[(4-methoxyphenyl)methoxy]-2,4,6-trimethyl-1-oxo-7,9-decadienyl]methylamino]-5-O-[(4-methoxyphenyl)methyl]-2,4-dimethyl-L-arabinitol (1.9 g, 2.2 mmol), CH$_2$Cl$_2$ (40 mL), and H$_2$O (1 mL) at room temperature, is added 2,3-dichloro-5,6-Dicyano-1,4-benzoquinone (DDQ), (2.53 g, 11.1 mmol). After stirring at room temperature for 10 min, the reaction mixture is purified by column chromatography on silica gel with hexane/EtOAc (90/10) to give the desired product (1.15 g, 82.6%) as a white solid.

$^1$H NMR (CDCl$_3$, 500 MHz), δ 6.57–6.45 (m, 1H), 6.03 (t, J=11.24 Hz, 1H), 5.20 (d, J=10.93 Hz, 1H), 5.13 (d, J=16.95 Hz, 1H), 5.03 (d, J=9.78 Hz, 1H), 4.04–3.91 (m, 1H), 3.54–3.45 (m, 4H), 3.22–3.16 (m, 1H), 3.07 (t, J=7.16 Hz, 1H), 2.93 (s, 3H), 2.67–2.59 (m, 1H), 2.45 (s, 1H), 2.10–1.96 (m, 1H), 1.80–1.72 (m, 1H), 1.52 (s, 1H), 0.98 (d, J=7.16 Hz 3H), 0.96 (d, J=7.16 Hz, 3H), 0.84 (d, J=6.77 Hz, 3H), 0.83–0.77 (m, 21H), 0.01 (s, 3H), 0.00 (s, 3H), 0.00 (s, 3H), –0.01 (s, 3H); $^{13}$C NMR (CDCl$_3$, 125 MHz), δ 176.3, 135.1, 132.2, 131.1, 118.2, 78.4, 76.2, 73.7, 65.7, 52.6, 40.3, 39.2, 37.0, 36.5, 36.2, 26.1, 26.1, 26.0, 18.25, 17.6, 17.3, 15.9, 15.5, 13.4, 9.0, –3.8, –3.9, –4.0, –4.1.

n) Preparation of 1,2,4-trideoxy-3-O-[(1,1-dimethylethyl)dimethylsilyl]-1-[[(2R,3S,4R,5S,6S,7Z)-3-[[(1,1-dimethylethyl)dimethylsilyl]oxy]-5-hydroxy-2,4,6-trimethyl-1-oxo-7,9-decadienyl]methylamino]-2,4-dimethyl-L-arabinitol.

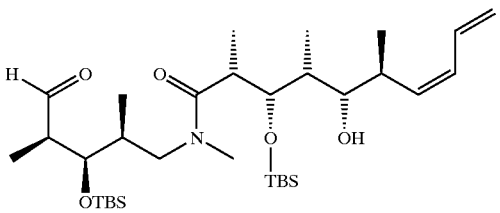

To a solution consisting of 1,2,4-trideoxy-3-O-[(1,1-dimethylethyl)dimethylsilyl]-1-[[(2R,3S,4R,5S,6S,7Z)-3-[[(1,1-dimethylethyl)dimethylsilyl]oxy]-5-hydroxy-2,4,6-trimethyl-1-oxo-7,9-decadienyl]methylamino]-2,4-dimethyl-L-arabinitol (1.8 g, 2.94 mmol), 2,2,6,6-tetramethyl-1-piperidinyloxy (TEMPO) (86 mg, 0.57 mmol), and CH$_2$Cl$_2$ (10 mL) at room temperature, is added iodobenzene diacetate (BAIB) (1.13 g, 3.51 mmol). The mixture is stirred at room temperature until TLC (hexane-EtOAc 95:5) indicates total consumption of the starting material. The mixture is diluted with CH$_2$Cl$_2$ (10 mL), and washed sequentially with saturated Na$_2$S$_2$O$_3$ (20 mL), 1 M NaHCO$_3$ (20 mL), then brine (20 mL). The solution is dried (Na$_2$SO$_4$) and concentrated in vacuo. The desired product (2.44 g) is obtained as an oil and is used in the next step without further purification.

$^1$H NMR (CDCl$_3$, 300 MHz), δ 9.62 (d, J=2.62 Hz, 1H), 6.52 (td, J=10.93, 16.95 Hz, 1H), 6.03 (t, J=10.92 Hz, 1H), 5.25–5.02 (m, 3H), 4.03 (q, J=3.76 Hz, 1H), 3.72 (q, J=5.65 Hz, 1H), 3.46 (d, J=7.91 Hz, 1H), 3.19–3.03 (m, 2H), 2.92 (s, 3H), 2.63 (q, J=7.53 Hz, 1H), 2.46 (td, J=2.63, 5.27 Hz, 1H), 2.01–1.90 (m, 1H), 1.79–1.75 (m, 1H), 1.48 (s, 1H), 1.19–1.47 (m, 4H), 1.02–0.96 (m, 6H), 0.83–0.73 (m, 24H), 0.00–0.05 (m, 12H); $^{13}$C NMR (CDCl$_3$, 75 MHz), δ 205.0, 176.7, 135.5, 132.6, 127.9, 118.8, 74.1, 51.3, 40.7, 39.6, 37.4, 36.9, 36.7, 32.0, 26.6, 26.4, 26.3, 23.1, 18.7, 18.7, 18.0, 14.3, 13.1, 12.4, 9.5, –3.4, –3.5, –3.7.

o) Preparation of (2Z,4S,5S,6S)-5-[[(1,1-dimethylethyl)dimethylsilyl]oxy]-7-[[(2R,3S,4R,5S,6S,7Z)-3-[[(1,1-dimethylethyl)dimethylsilyl]oxy]-5-hydroxy-2,4,6-trimethyl-1-oxo-7,9-decadienyl]methylamino]-4,6-dimethyl-2-heptenoic acid methyl ester.

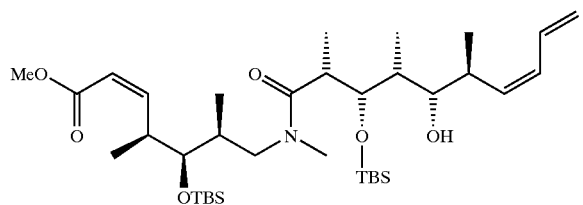

To a solution consisting of bis(2,2,2-trifluoroethyl)-2,2,5-(methoxycarbonylmethyl)phosphonate (715 mg, 2.25 mmol), 18-crown-6 (453 mg, 1.7 mmol), and toluene (5 mL) at –20° C., is slowly added a solution of potassium bis(trimethylsilyl)amide (0.5 M in toluene, 4.5 mL, 2.25 mmol). After stirring at 0° C. for 20 min, the mixture is cooled to –20° C., and a solution of 1,2,4-trideoxy-3-O-[(1,1-dimethylethyl)dimethylsilyl]-1-[[(2R,3S,4R,5S,6S,7Z)-3-[[(1,1-dimethylethyl) dimethylsilyl]oxy]-5-hydroxy-2,4,6-trimethyl-1-oxo-7,9-decadienyl]methylamino]-2,4-dimethyl-L-arabinitol (711 mg, 0.85 mmol) in toluene (3 mL) is added slowly. The mixture is stirred at 0° C. for 3 h, after which the mixture is quenched with saturated NH$_4$Cl (10 mL), and extracted with EtOAc (3×20 mL). The combined organic layers are then dried (Na$_2$SO$_4$), concentrated, and purified by column chromatography on silica gel with hexane/EtOAc (90/10) to give the desired compound (487 mg, 85.3%) as a thick colorless oil.

$^1$H NMR (CDCl$_3$, 500 MHz), δ 6.60–6.47 (m, 1H), 6.31 (t, J=12.06 Hz, 1H), 6.04 (t, J=10.92 Hz, 1H), 5.69 (dd, J=11.30, 3.01 Hz, 1H), 5.24 (t, J=10.55 Hz, 1H), 5.13 (d, J=7.32 Hz, 1H), 5.04 (d, J=10.17 Hz, 1H), 2H), 4.05 (dd, J=8.29, 4.52 Hz, 1H), 3.93 (dd, J=8.24, 4.14 Hz, 1H), 3.60 (s, 3H), 3.52 (d, J=7.91 Hz, 1H), 3.45–3.39 (m, 3H), 3.09–3.02 (m, 1H), 2.88 (s, 3H), 2.71–2.61 (m, 2H), 1.89–1.76 (m, 2H), 1.60 (dd, J=14.32, 3.77 Hz, 1H), 1.17 (d, J=3.01 Hz, 1H), 0.99 (d, J=7.06 Hz, 3H), 0.96 (d, J=4.14 Hz, 3H), 0.94 (d, J=4.03 Hz, 3H), 0.83 (s, 18H), 0.79–0.74 (m, 6H), 0.03–0.00 (m, 12H); $^{13}$C NMR (CDCl$_3$, 500 MHz), δ 176.5, 167.0, 153.0, 152.7, 131.6, 131.3, 118.8, 118.5, 78.2, 76.7, 74.3, 51.5, 51.3, 40.6, 39.7, 37.4, 37.3, 37.2, 36.0, 26.5, 26.4, 18.7, 18.7, 18.6, 18.0, 14.5, 13.8, 9.2, –3.2, –3.4, –3.5, –3.6.

p) Preparation of (2Z,4S,5S,6S)-7-[[(2R,3S,4R,5S,6S,7Z)-5-[(aminocarbonyl)oxy]-3-[[(1,1-dimethylethyl)

dimethylsilyl]oxy]-2,4,6-trimethyl-1-oxo-7,9-decadienyl]
methylamino]-5-[[(1,1-dimethylethyl)dimethylsilyl]oxy]-4,
6-dimethyl-2-heptenoic acid methyl ester.

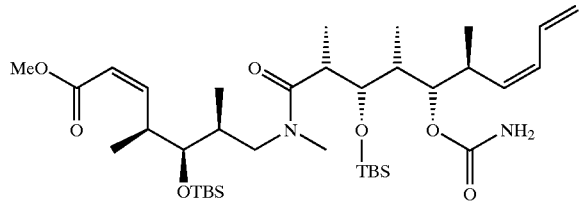

To a solution of (2Z,4S,5S,6S)-5-[[(1,1-dimethylethyl)
dimethylsilyl]oxy]-7-[[(2R,3S,4R,5S,6S,7Z)-3-[[(1,1-dimethylethyl)dimethylsilyl]oxy]-5-hydroxy-2,4,6-trimethyl-1-oxo-7,9-decadienyl]methylamino]-4,6-dimethyl-2-heptenoic acid methyl ester (1.8 g, 2.7 mmol) in CH$_2$Cl$_2$ (10 mL) at room temperature, is added trichloroacetyl isocyanate (763 mg, 4.05 mmol) in one portion. The mixture is stirred at room temperature for 1 h, and concentrated in vacuo. The residue is dissolved in MeOH (10 mL), and then K$_2$CO$_3$ (0.4 g) is added. After stirring at room temperature for 2 h, the mixture is concentrated in vacuo, then purified by column chromatography with silica gel eluted with hexane/EtOAc (70/30) to give the desired compound (1.77 g, 92.4%) as a colorless glassy solid.

$^1$H NMR (CDCl$_3$, 500 MHz), δ 6.65 (td, J=10.87, 16.71 Hz, 1H), 6.46–6.36 (m, 1H), 6.01 (t, J=10.87 Hz, 1H), 5.80 (dd, J=11.67, 8.04 Hz, 1H), 5.42 (q, J=11.11 Hz, 1H), 5.21–5.51 (m, 2H), 4.94 (t, J=5.51 Hz, 1H), 4.83 (dd, J=8.51, 3.46 Hz, 1H), 4.60 (s, 1H), 4.52 (s, 1H), 4.08 (dd, J=7.88, 3.15 Hz, 1H), 3.97 (dd, J=7.56, 1.42 Hz, 1H), 3.71 (s, 3H), 3.58–3.57 (m, 1H), 3.54 (t, J=3.63 Hz, 1H), 3.42–3.31 (m, 2H), 3.16–3.09 (m, 1H), 3.01–2.96 (m, 1H), 2.93 (s, 1H), 2.87 (t, J=7.10 Hz, 1H), 2.79–2.75 (m, 1H), 2.71 (s, 1H), 1.95–1.87 (m, 1H), 1.09 (d, J=3.62 Hz, 3H), 1.08 (d, J=3.74 Hz, 3H), 1.05 (d, J=8.36 Hz, 3H), 1.10 (d, J=6.94 Hz, 3H), 0.94 (s, 18H), 0.86 (d, J=7.25 Hz, 3H), 0.83 (d, J=6.94 Hz, 3H), 0.12 (s, 3H), 0.12 (s, 3H), 0.11 (s, 3H), 0.11 (s, 3H); $^{13}$C NMR (CDCl$_3$, 500 MHz), δ 175.8, 167.1, 157.3, 153.1, 133.4, 133.0, 130.7, 118.9, 117.8, 78.7, 77.7, 74.5, 51.6, 51.5, 41.0, 40.1, 38.7, 37.4, 37.3, 36.2, 35.8, 26.6, 26.5, 18.9, 18.8, 18.5, 14.4, 13.9, 10.6, −3.1, −3.4, −3.6.

q) Preparation of (2R,3S,4R,5S,6S,7Z)-5-[(aminocarbonyl)oxy]-3-[[(1,1-dimethylethyl)dimethylsilyl]oxy]-N-[(2S,3S,4S,5Z)-3-[[(1,1-dimethylethyl)dimethylsilyl]oxy]-7-hydroxy-2,4-dimethyl-5-heptenyl]-N,2,4,6-tetramethyl-7,9-decadienamide.

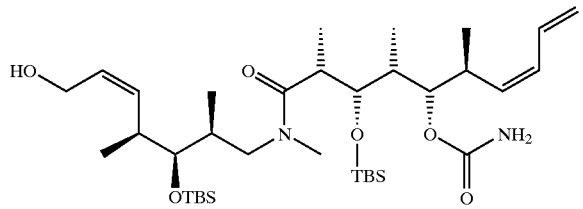

To a solution of (2Z,4S,5S,6S)-7-[[(2R,3S,4R,5S,6S,7Z)-5-[(aminocarbonyl)oxy]-3-[[(1,1-dimethylethyl)dimethylsilyl]oxy]-2,4,6-trimethyl-1-oxo-7,9-decadienyl]methylamino]-5-[[(1,1-dimethylethyl)dimethylsilyl]oxy]-4,6-dimethyl-2-heptenoic acid methyl ester (1.77 g, 2.5 mmol)

and CH$_2$Cl$_2$ (15 mL) cooled to −78° C., was added a solution consisting of diisobutylaluminum hydride (1.0 M in hexane, 7.5 mL, 7.5 mmol). After stirring at −40° C. for 4 h, the mixture is quenched by adding saturated potassium sodium tartrate (10 mL). The mixture is then extracted with CH$_2$Cl$_2$ (3×20 mL). The combined organic layers are then dried (Na$_2$SO$_4$), concentrated in vacuo, and chromatographed using silica gel eluted with hexane/EtOAc (70/30) to give the desired compound (1.04 mg, 61.4%) as a colorless glassy solid.

$^1$H NMR (CDCl$_3$, 500 MHz), δ 6.68–6.60 (m, 1H), 6.06–6.01 (m, 1H), 5.67–5.60 (m, 2H), 5.42 (t, J=9.77 Hz, 1H), 5.22 (d, J=6.86 Hz, 1H), 5.13 (d, J=5.83 Hz, 1H), 4.94 (t, J=5.83 Hz, 1H), 4.47 (s, 1H), 4.41–4.36 (m, 2H), 4.06 (dd, J=7.41, 3.47 Hz, 1H), 4.01–3.96 (m, 1H), 3.69 (dd, J=13.24, 11.83 Hz, 1H), 3.53 (dd, J=8.82, 4.25 Hz, 1H), 3.48 (dd, J=5.36, 2.36 Hz, 1H), 3.07 (dd, J=13.04, 4.25 Hz, 1H), 3.00–2.97 (m, 1H), 2.95 (s, 3H), 2.89–2.81 (m, 2H), 2.06–2.01 (m, 1H), 1.94–1.91 (m, 1H), 1.07 (d, J=6.94 Hz, 3H), 1.01 (d, J=6.78 Hz, 3H), 0.99 (d, J=6.94 Hz, 3H), 0.94 (s, 18H), 0.86 (d, J=7.25 Hz, 3H), 0.85 (d, J=7.05 Hz, 3H), 0.13 (s, 3H), 0.11 (s, 3H), 0.09 (s, 6H); $^{13}$C NMR (CDCl$_3$, 125 MHz), δ 176.2, 157.2, 134.9, 133.5, 132.9, 130.6, 128.7, 118.0, 79.3, 77.7, 74.4, 58.9, 50.4, 40.6, 40.0, 37.8, 37.7, 36.0, 35.9, 35.1, 34.3, 26.6, 26.5, 21.0, 18.4, 15.9, 14.7, 13.6, 10.7, −3.4, −3.5, −3.8.

r) Preparation of (2R,3S,4R,5S,6S,7Z)-5-[(aminocarbonyl)oxy]-3-[[(1,1-dimethylethyl)dimethylsilyl]oxy]-N-[(2S,3S,4S,5Z)-3-[[(1,1-dimethylethyl)dimethylsilyl]oxy]-2,4-dimethyl-7-oxo-5-heptenyl]-N,2,4,6-tetramethyl-7,9-decadienamide.

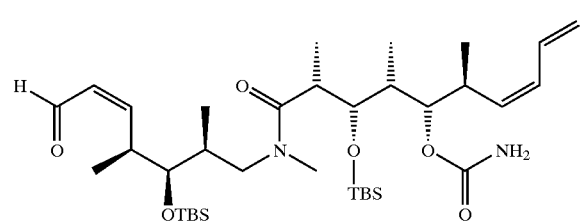

To a solution of Dess-Martin periodinane (199 mg, 0.47 mmol) and CH$_2$Cl$_2$ (4 mL) at room temperature, is added a solution of (2R,3S,4R,5S,6S,7Z)-5-[(aminocarbonyl)oxy]-3-[[(1,1-dimethylethyl)dimethylsilyl]oxy]-N-[(2S,3S,4S,5Z)-3-[[(1,1-dimethylethyl)dimethylsilyl]oxy]-7-hydroxy-2,4-dimethyl-5-heptenyl]-N,2,4,6-tetramethyl-7,9-decadienamide (200 mg, 0.29 mmol) and CH$_2$Cl$_2$ (1 mL). After stirring at room temperature for 1 h, the mixture is quenched by adding saturated NaHCO$_3$ (1 mL) followed by saturated Na$_2$S$_2$O$_3$ (1 mL). This mixture is then stirred at room temperature for 30 min, and then extracted with CH$_2$Cl$_2$ (4×10 mL). The combined organic layers are then dried (Na$_2$SO$_4$), concentrated in vacuo, and then chromatographed (silica gel eluted with hexane/EtOAc 90/10) to give the desired compound (150 mg, 75.2%) as a colorless glassy solid.

$^1$H NMR (CDCl$_3$, 300 MHz), δ 6.61–6.47 (m, 2H), 5.94–5.83 (m, 1H), 5.30 (t, J=9.80 Hz, 1H), 5.11–5.00 (m, 2H), 4.81 (t, J=5.66 Hz, 1H), 4.49 (s, 1H), 3.95 (dd, J=7.54, 3.02 Hz, 1H), 3.44 (t, J=3.76 Hz, 1H), 3.16–3.11 (m, 1H), 2.88 (m, 1H), 2.86 (s, 3H), 2.77 (t, 2.77 Hz, 1H), 2.64 (s,

1H), 1.94–1.72 (m, 2H), 1.20–1.13 (m, 2H), 1.05–0.97 (m, 6H), 0.89 (d, J=6.78 Hz, 3H), 0.83 (s, 9H), 0.81 (s, 9H), 0.78–0.74 (m, 6H), 0.03 (s, 3H), 0.01 (s, 3H), 0.00 (s, 3H), −0.04 (s, 3H); $^{13}$C NMR (CDCl$_3$, 75 MHz), δ 191.5, 175.8, 157.3, 155.9, 133.4, 133.0, 129.9, 117.8, 78.0, 77.7, 74.3, 52.6, 40.1, 37.4, 37.0, 36.8, 35.7, 26.6, 26.5, 26.5, 19.9, 18.8, 18.6, 15.8, 13.3, 10.6, −3.1, −3.2, −3.4, −3.4.

s) Preparation of (2R,3S,4R,7S,8Z,10S,11S,12S)-13-[[(2R, 3S,4R,5S,6S,7Z)-5-[(aminocarbonyl)oxy]-3-[[(1,1-dimethylethyl)dimethylsilyl]oxy]-2,4,6-trimethyl-1-oxo-7, 9-decadienyl]methylamino]-3,11-bis[[(1,1-dimethylethyl) dimethylsilyl]oxy]-7-hydroxy-N-methoxy-N,2,4,10,12-pentamethyl-5-oxo-8-tridecenamide.

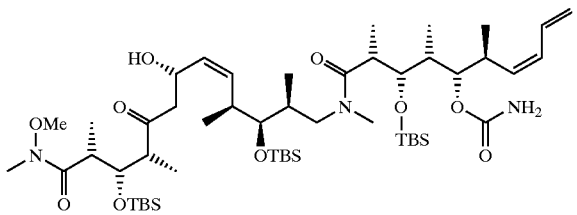

To a solution of (+)-β-chlorodiisopinocampheylborane (502 mg, 1.52 mmol) and ether (1.3 mL) cooled to −6° C., is added Et$_3$N (0.23 mL, 1.67 mmol). To this mixture is added a solution of (2R,3S,4R)-3-[[(1,1-dimethylethyl) dimethylsilyl]oxy]-N-methoxy-N-methyl-2,4-trimethyl-5-oxo-hexanamide and ether (1.5 mL). After stirring at 0° C. for 2 h, the mixture is cooled to −78° C. To this mixture is added a solution of (2R,3S,4R,5S,6S,7Z)-5-[(aminocarbonyl)oxy]-3-[[(1,1-dimethylethyl) dimethylsilyl]oxy]-N-[(2S,3S,4S,5Z)-3-[[(1,1-dimethylethyl)dimethylsilyl]oxy]-2,4-dimethyl-7-oxo-5-heptenyl]-N,2,4,6-tetramethyl-7,9-decadienamide (103 mg, 0.152 mmol) and ether. The mixture is stirred at −78° C. for 3 h, and then at −30° C. overnight. The reaction mixture is quenched by the sequential addition of MeOH (4 mL), a phosphate buffer (pH=7, 1.5 mL), then H$_2$O$_2$ (30%, 1.0 mL) at −78° C. The mixture is warmed to room temperature and stirred for 2 h. The mixture is extracted with CH$_2$Cl$_2$ (4×10 mL). The combined organic layers are then dried (Na$_2$SO$_4$), concentrated in vacuo, and then chromatographed (silica gel eluted with hexane/EtOAc 80/20) to give the desired compound (123 mg, 80.3%) as a colorless glassy solid.

$^1$H NMR (CDCl$_3$, 500 MHz), δ 6.69–6.61 (m, 1H), 6.03 (t, J=11.42 Hz, 1H), 5.58 (t, J=10.55 Hz, 1H), 5.44–5.40 (m, 2H), 5.22–5.19 (m, 1H), 5.17–5.13 (m, 1H), 4.95 (t, J=6.06 Hz 1H), 4.84–4.80 (m, 1H), 4.66–4.45 (m, 2H), 4.35 (dd, J=8.24, 4.12 Hz, 1H), 4.09 (dd, J=7.62, 3.20 Hz, 1H), 3.74 (s, 3H), 3.49–3.38 (m, 3H), 3.11 (s, 3H), 3.07–3.02 (m, 1H), 3.00–2.94 (m, 3H), 2.89–2.76 (m, 4H), 2.69–2.56 (m, 1H), 2.02–1.97 (M, 1H), 1.91–1.88 (m, 1H), 1.72–1.66 (m, 1H), 1.27 (s, 3H), 1.15–1.11 (m, 6H), 1.10–1.08 (m, 6H), 1.03–1.00 (m, 6H), 0.95 (s, 9H), 0.93 (s, 9H), 0.92 (s, 9H), 0.14 (s, 3H), 0.13 (s, 3H), 0.12 (s, 3H), 0.12 (s, 3H), 0.12 (s, 3H), 0.11 (s, 3H); $^{13}$C NMR (CDCl$_3$, 125 MHz), δ 212.6, 175.3, 157.0, 156.8, 135.4, 133.0, 132.5, 130.1, 129.8, 117.5, 78.1, 77.2, 74.1, 65.1, 61.3, 53.4, 51.8, 48.9, 40.3, 39.6, 36.8, 36.2, 35.9, 35.4, 29.7, 26.2, 26.2, 26.2, 26.1, 26.1, 25.9, 25.9, 19.7, 18.5, 18.4, 18.1, 15.6, 12.8, 10.2, 10.0, −3.6, −3.8, −3.8, −4.2, −4.5.

t) Preparation of (2R,3S,4S,5S,7S,8Z,10S,11S,12S)-13-[[(2R,3S,4R,5S,6S,7Z)-5-[(aminocarbonyl)oxy]-3-[[(1,1-dimethylethyl)dimethylsilyl]oxy]-2,4,6-trimethyl-1-oxo-7, 9-decadienyl]methylamino]-3,11-bis[[(1,1-dimethylethyl) dimethylsilyl]oxy]-5,7-dihydroxy-N-methoxy-N, 2,4,10,12-pentamethyl-8-tridecenamide.

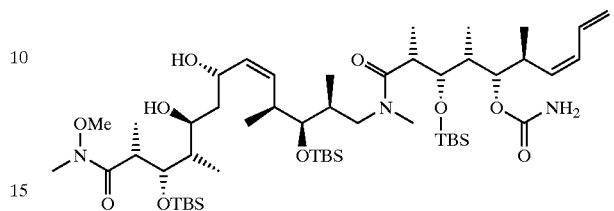

Tetramethylammonium triacetoxy borohydride (182 mg, 0.69 mmol) is first dissolved in a mixed solution of THF/ AcOH (1:1, 0.5 mL). After stirring at room temperature for 1 h, the mixture is cooled at −30° C., and then a solution of (2R,3S,4R,7S,8Z,10S,11S,12S)-13-[[(2R,3S,4R,5S,6S,7Z)-5-[(aminocarbonyl)oxy]-3-[[(1,1-dimethylethyl) dimethylsilyl]oxy]-2,4,6-trimethyl-1-oxo-7,9-decadienyl] methylamino]-3,11-bis[[(1,1-dimethylethyl)dimethylsilyl] oxy]-7-hydroxy-N-methoxy-N,2,4,10,12-pentamethyl-5-oxo-8-tridecenamide (50 mg, 0.049 mmol) in THF/AcOH (1:1, 0.5 mL) is added slowly. The reaction mixture is stirred at −30° C. for 3 h and at 0° C. overnight. The reaction mixture is quenched by adding saturated potassium sodium tartrate (0.5 mL). The mixture is extracted with CH$_2$Cl$_2$ (3×10 mL). The combined organic layers are neutralized by adding saturated NaHCO$_3$, dried (Na$_2$SO$_4$), concentrated in vacuo, then chromatographed (silica gel eluted with hexane/ EtOAc 95/5) to give the desired compound (39.1 mg, 78.4%) as a colorless glassy solid.

$^1$H NMR (CDCl$_3$, 500 MHz), δ 6.58–6.49 (m, 1H), 5.93–5.88 (m, 1H), 5.40–5.30 (m, 3H), 5.10–5.01 (m, 2H), 4.81 (t, J=5.52 Hz 1H), 4.71 (dd, J=8.51, 2.84 Hz, 1H), 4.59 (s, 1H), 4.55–4.41 (m, 3H), 4.10 (d, J=9.45, 1H), 3.96 (dd, J=7.56, 2.99 Hz, 1H), 3.86 (s, 1H), 3.83 (d, J=7.72 Hz, 1H), 3.63 (s, 3H), 3.33 (s, 1H), 3.30–3.23 (m, 4H), 3.08 (s, 3H), 3.03–2.94 (m, 2H), 2.86 (s, 3H), 2.77–2.69 (m, 2H), 2.63–2.58 (m, 2H), 1.86–1.81 (m, 2H), 1.80–1.76 (m, 2H), 1.68–1.62 (m, 2H), 1.57–1.48 (m, 2H), 1.43–1.39 (m, 1H), 1.07 (dd, J=6.94, 2.21 Hz, 3H), 0.98 (t, J=7.56 Hz, 3H), 0.93–0.88 (m, 6H), 0.83–0.80 (m, 18H), 0.75–0.69 (m, 9H), 0.06 to −0.05 (m, 18H); $^{13}$C NMR (CDCl$_3$, 125 MHz), δ 175.7, 175.6, 157.2, 134.2, 133.3, 133.2, 132.9, 131.9, 130.5, 117.9, 78.2, 77.8, 74.8, 74.6, 74.4, 74.2, 71.0, 66.1, 62.1, 52.8, 46.5, 40.6, 40.2, 37.7, 36.7, 35.8, 33.7, 32.8, 26.6, 26.5, 26.3, 19.9, 18.9, 18.8, 18.5, 18.4, 16.4, 16.0, 13.2, 12.3, 10.6, 10.4, −3.3, −3.4, −3.8, −4.1.

u) Preparation of (2R,3S,4R,5S,7S,8Z)-13-[[(2R,3S,4S,5S, 6S,7Z)-5-[(aminocarbonyl)oxy]-3-hydroxy-2,4,6-trimethyl-1-oxo-7,9-decadienyl]methylamino]-3,5,7,11-tetrahydroxy-2,4,10,12-tetramethyl-8-tridecenoic acid δ-lactone

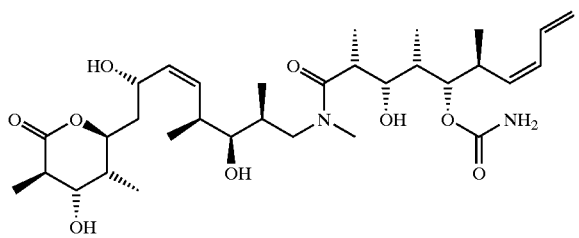

(2R,3S,4S,5S,7S,8Z,10S,11S,12S)-13-[[(2R,3S,4R,5S,6S,7Z)-5-[(aminocarbonyl)oxy]-3-[[(1,1-dimethylethyl)dimethylsilyl]oxy]-2,4,6-trimethyl-1-oxo-7,9-decadienyl]methylamino]-3,11-bis[[(1,1-dimethylethyl)dimethylsilyl]oxy]-5,7-dihydroxy-N-methoxy-N,2,4,10,12-pentamethyl-8-tridecenamide (115 mg, 0.114 mmol) is dissolved in a solution consisting of isopropanol (15 mL) and HCl (4 N,12 mL) at room temperature. After stirring at room temperature for 60 h, the mixture is cooled at −15° C., and diluted with EtOAc (50 mL). The solution is neutralized by adding solid NaHCO$_3$ in very small portions at −15° C., and is then extracted with EtOAc (6×30 mL). The combined organic layers are dried (Na$_2$SO$_4$), concentrated in vacuo, then purified by HPLC on a reverse phase column (Nova-Pak C18, Waters) eluted with CH$_3$CN/H$_2$O (32:68) to give the desired compound (40.7 mg, 49.5%) as a colorless glassy solid.

$^1$H NMR (CDCl$_3$, 500 MHz), δ 6.64 (dd, J=16.86, 10.40 Hz, 1H), 6.05 (t, J=10.72 Hz, 1H), 5.52 (dd, J=11.03, 7.56 Hz, 1H), 5.31–5.22 (m, 2H), 5.15 (d, J=10.14 Hz, 1H), 4.90 (s, 1H), 4.76 (s, 1H), 4.66–4.62 (m, 1H), 4.60 (d, J=9.62 Hz, 1H), 4.52 (m, 1H), 4.03–3.96 (m, 2H), 3.75 (s, 1H), 3.63 (d, J=8.83 Hz, 1H), 3.28 (d, J=7.09 Hz, 1H), 3.07 (s, 3H), 3.02 (d, J=6.62 Hz, 1H), 2.91 (d, J=4.26 Hz, 1H), 2.83–2.78 (m, 1H), 2.69–2.61 (m, 4H), 2.35 (s, 1H), 1.99–1.91 (m, 3H), 1.89–1.85 (m, 2H), 1.35 (d, J=7.26 Hz, 3H), 1.16 (d, J=7.10 Hz, 3H), 1.13 (d, J=6.77 Hz, 3H), 1.10 (d, J=6.94 Hz, 3H), 1.01 (d, J=6.78 Hz, 3H), 0.94 (dd, J=10.87, 6.62 Hz, 2H), 0.90 (d, J=6.47 Hz, 3H), 0.87 (d, J=6.78 Hz, 3H); $^{13}$C NMR (CDCl$_3$, 500 MHz), δ 180.0, 174.5, 157.3, 135.8, 134.4, 132.7, 130.7, 118.3, 73.5, 73.2, 72.7, 72.3, 65.5, 51.6, 43.5, 41.5, 36.6, 36.3, 35.6, 35.1, 35.0, 33.5, 32.7, 30.1, 18.0, 17.3, 15.8, 12.8, 10.9, 10.5, 9.7.

Following are the corresponding structures of the compounds of Examples 1 and 2:

EXAMPLE 1

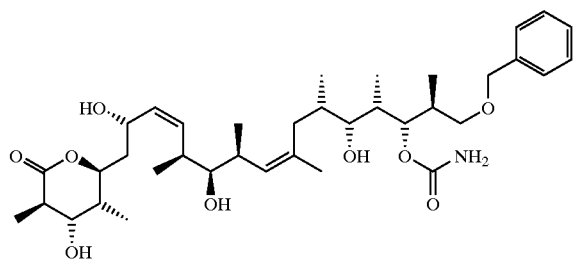

EXAMPLE 2

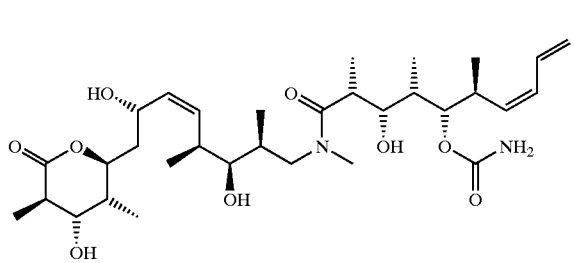

What is claimed is:
1. A compound of formula I

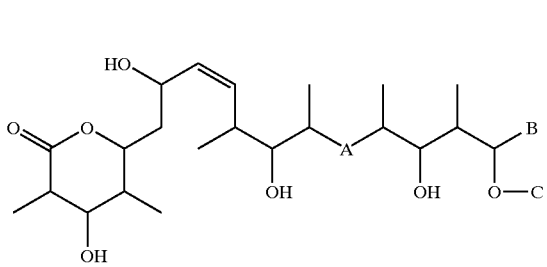

where A is —CH=C(R$_1$)CH$_2$—, —CH$_2$N(R$_2$)CH$_2$—, —CH$_2$N(R$_2$)C(O)—, —C(O)N(R$_2$)CH$_2$—, —CH$_2$N(CO$_2$R$_3$)CH$_2$— or —CH$_2$N(COR$_2$)CH$_2$—;

B is —CH(R$_1$)CH=CHCH=CH$_2$, —CH(R$_2$)R$_1$, —CH(R$_1$)CH=CHR$_2$, —CH(R$_1$)CH=CHC(O)OR$_2$, —CH(R$_1$)CH=CHC(O)N(R$_1$)R$_2$, —CH(R$_1$)CH$_2$OR$_2$ or Ar;

C is H, —C(O)N(R$_1$)R$_2$, —C(O)NHCH$_2$(CH$_2$)$_n$N(CH$_3$)$_2$, or —C(O)NHCH$_2$(CH$_2$)$_n$-4-morpholino;

R$_1$ is H or (C$_{1-6}$)alkyl;

R$_2$ is H, (C$_{1-6}$)alkyl, (C$_{2-6}$)alkenyl, (C$_{2-6}$)alkynyl, (C$_{1-6}$)alkyl-Ar or Ar;

R$_3$ is (C$_{1-6}$)alkyl, (C$_{1-6}$)alkyl-Ar or Ar;

Ar is an aromatic or heteroaromatic ring selected from

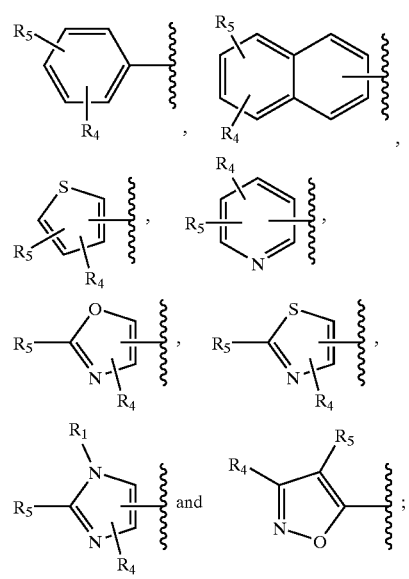

R$_4$ and R$_5$ are, independently, H, (C$_{1-6}$)alkyl, OH, O(C$_{1-6}$)alkyl, OCH$_2$(CH$_2$)$_n$OH, O(CH$_2$)$_n$CO$_2$H, OCH$_2$(CH$_2$)$_n$N(CH$_3$)$_2$, OCH$_2$(CH$_2$)$_n$-4-morpholino, F, Cl, Br or CF$_3$; and n is 1 or 2;

with the proviso that when A is —CH=C(CH$_3$)CH$_2$— or —CH=CHCH$_2$—, then either:

B cannot be —CH(CH$_3$)CH=CHCH=CH$_2$, —CH(CH$_3$)CH$_2$Ph, —CH(CH$_3$)Ph, —CH(CH$_3$)-n-Bu,

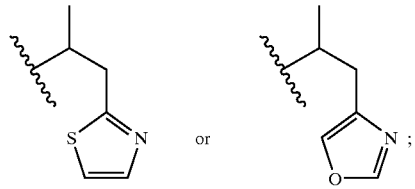

or C cannot be —C(O)N(R$_1$)R$_2$ or H;

or an acid or base addition salt thereof, where possible.

2. A compound according to claim 1 of formula Ia

Ia

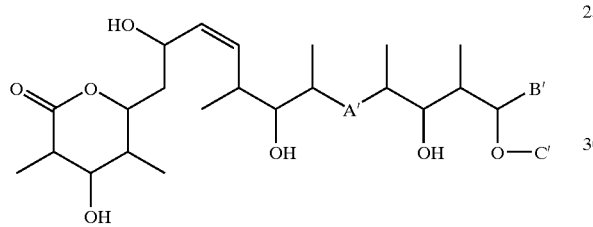

where A' is —CH=C(R$_1$')CH$_2$—, —CH$_2$N(R$_2$')C(O)—, —C(O)N(R$_2$')CH$_2$—, —CH$_2$N(CO$_2$R$_3$)CH$_2$— or —CH$_2$N(COR$_2$')CH$_2$—;

B' is —CH(R$_1$')CH=CHCH=CH$_2$, —CH(R$_2$')R$_1$', —CH(R$_1$')CH=CHR$_2$', —CH(R$_1$')CH$_2$OR$_2$' or Ar';

C' is H, —C(O)N(R$_1$')R$_2$', —C(O)NHCH$_2$(CH$_2$)$_n$N(CH$_3$)$_2$, or —C(O)NHCH$_2$(CH$_2$)$_n$-4-morpholino;

R$_1$' is H or (C$_{1-6}$)alkyl;

R$_2$' is H, (C$_{1-6}$)alkyl, (C$_{2-6}$)alkenyl, (C$_{2-6}$)alkynyl, (C$_{1-6}$)alkyl-Ar' or Ar';

R$_3$' is (C$_{1-6}$)alkyl, (C$_{1-6}$)alkyl-Ar' or Ar';

Ar' is an aromatic or heteroaromatic ring selected from

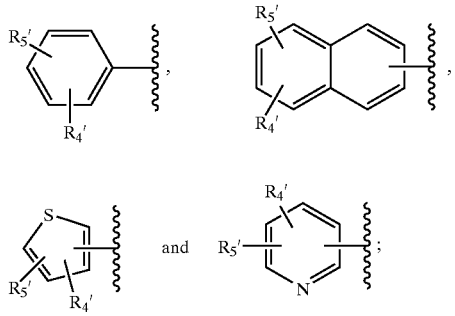

R$_4$' and R$_5$' are, independently, H, (C$_{1-6}$)alkyl, OH, O(C$_{1-6}$)alkyl, OCH$_2$(CH$_2$)$_n$ OH, O(CH$_2$)$_n$ CO$_2$H, OCH$_2$(CH$_2$)$_n$ N(CH$_3$)$_2$, OCH$_2$(CH$_2$)$_n$-4-morpholino, F, Cl, Br or CF$_3$; and n is 1 or 2;

with the proviso that when A' is —CH=C(CH$_3$)CH$_2$— or —CH=CHCH$_2$—, then either:

B' cannot be —CH(CH$_3$)CH=CHCH=CH$_2$, —CH(CH$_3$)CH$_2$Ph, —CH(CH$_3$)Ph, —CH(CH$_3$)-n-Bu,

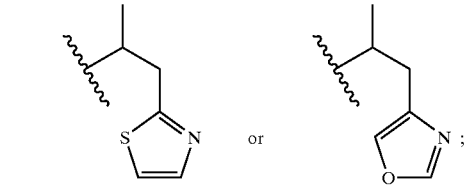

or C' cannot be —C(O)N(R$_1$')R$_2$' or H;

or an acid or base addition salt thereof, where possible.

3. A compound according to claim 2 of formula Ib

Ib

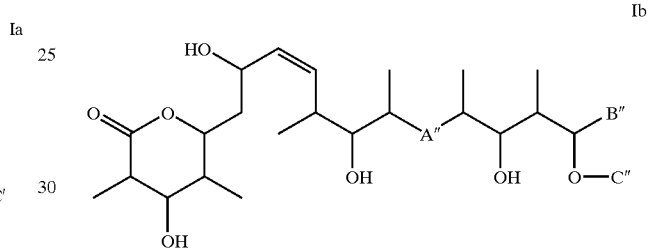

where A" is —CH=C(R$_1$")CH$_2$—, —CH$_2$N(R$_2$")C(O)— or —C(O)N(R$_2$")CH$_2$—;

B" is —CH(R$_1$")CH=CHCH=CH$_2$, —CH(R$_2$")R$_1$", —CH(R$_1$")CH=CHR$_2$", —CH(R$_1$")CH$_2$OR$_2$" or Ar";

C" is H, —C(O)N(R$_1$")R$_2$", —C(O)NHCH$_2$(CH$_2$)$_n$N(CH$_3$)$_2$ or —C(O)NHCH$_2$(CH$_2$)$_n$-4-morpholino;

R$_1$" is H or —CH$_3$;

R$_2$" is H, (C$_{1-6}$)alkyl, (C$_{2-6}$)alkenyl, (C$_{2-6}$)alkynyl, (C$_{1-6}$)alkyl-Ar" or Ar";

Ar" is an aromatic or heteroaromatic ring selected from

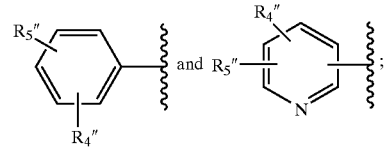

R$_4$" and R$_5$" are, independently, H, (C$_{1-6}$)alkyl, OH, O(C$_{1-6}$)alkyl, OCH$_2$(CH$_2$)$_n$OH, O(CH$_2$)$_n$CO$_2$H, OCH$_2$(CH$_2$)$_n$N(CH$_3$)$_2$, OCH$_2$(CH$_2$)$_n$-4-morpholino, F, Cl, Br or CF$_3$; and n is 1 or 2;

with the proviso that when A" is —CH=C(CH$_3$)CH$_2$— or —CH=CHCH$_2$—, then either:

B" cannot be —CH(CH$_3$)CH=CHCH=CH$_2$, —CH(CH$_3$)CH$_2$Ph, —CH(CH$_3$)Ph, —CH(CH$_3$)-n-Bu,

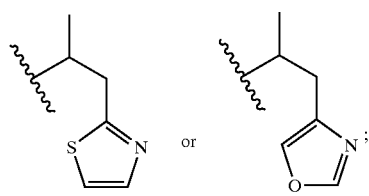

or C''' cannot be —C(O)N(R$_1$'')R$_2$'' or H;

or an acid or base addition salt thereof, where possible.

4. A compound according to claim 3 of formula Ic

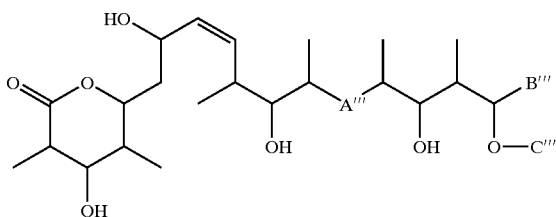

Ic where A''' is —CH=C(R$_1$''')CH$_2$—, —CH$_2$N(R$_2$''')C(O)— or —C(O)N(R$_2$''')CH$_2$—;

B''' is —CH(R$_1$''')CH=CHCH=CH$_2$, —CH(R$_2$''')R$_1$''', —CH(R$_1$''')CH=CHR$_2$''', —CH(R$_1$''')CH$_2$OR$_2$''' or Ar''';

C''' is H or —C(O)N(R$_1$''')R$_2$''';

R$_1$''' is H or CH$_3$;

R$_2$''' is H, (C$_{1-6}$)alkyl, (C$_{2-6}$)alkenyl, (C$_{2-6}$)alkynyl, (C$_{1-6}$)alkyl-Ar''' or Ar''';

Ar''' is an aromatic ring selected having the formula

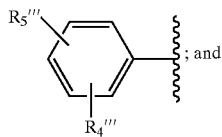; and

R$_4$''' and R$_5$''' are, independently, H, (C$_{1-6}$)alkyl, OH, O(C$_{1-6}$)alkyl, F, Cl, Br or CF$_3$;

with the proviso that when A''' is —CH=C(CH$_3$)CH$_2$— or —CH=CHCH$_2$—, then either:

B''' cannot be —CH(CH$_3$)CH=CHCH=CH$_2$, —CH(CH$_3$)CH$_2$Ph, —CH(CH$_3$)Ph, —CH(CH$_3$)-n-Bu,

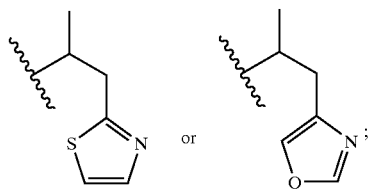

or C''' cannot be —C(O)N(R$_1$''')R$_2$''' or H;

or an acid or base addition salt thereof, where possible.

5. A compound according to claim 1 of formula I, or a pharmaceutically acceptable acid or base addition salt thereof, where possible.

6. A compound according to claim 2 of formula Ia, or a pharmaceutically acceptable acid or base addition salt thereof, where possible.

7. A compound according to claim 3 of formula Ib, or a pharmaceutically acceptable acid or base addition salt thereof, where possible.

8. A compound according to claim 4 of formula Ic, or a pharmaceutically acceptable acid or base addition salt thereof, where possible.

9. A compound selected from

19-[(aminocarbonyl)oxy]-3,5,7,11,17-pentahydroxy-2,3,4,10,12,14,16,18,20-nonamethyl-21-(phenylmethoxy)-8,13-heneicosadienoic acid δ-lactone and 13-[[5-[(aminocarbonyl)oxy]-3-hydroxy-2,4,6-trimethyl-1-oxo-7,9-decadienyl]methylamino]-3,5,7,11-tetrahydroxy-2,4,10,12-tetramethyl-8-tridecenoic acid δ-lactone, or a pharmaceutically acceptable acid or base addition salt thereof.

10. A compound selected from (2R,3S,4S,5S,7S,8Z,10S,11S,12S,13Z,16S,17R,18S,19S,20S)-19-[(aminocarbonyl)oxy]-3,5,7,11,17-pentahydroxy-2,3,4,10,12,14,16,18,20-nonamethyl-21-(phenylmethoxy)-8,13-heneicosadienoic acid δ-lactone and (2R,3S,4R,5S,7S,8Z)-13-[[(2R,3S,4S,5S,6S,7Z)-5-[(aminocarbonyl)oxy]-3-hydroxy-2,4,6-trimethyl-1-oxo-7,9-decadienyl]methylamino]-3,5,7,11-tetrahydroxy-2,4,10,12-tetramethyl-8-tridecenoic acid δ-lactone, or a pharmaceutically acceptable acid or base addition salt thereof.

11. A pharmaceutical composition comprising a pharmaceutically acceptable carrier or diluent and a therapeutically effective amount of a compound according to claim 5, or a pharmaceutically acceptable acid or base addition salt thereof, where possible.

12. A pharmaceutical composition comprising a pharmaceutically acceptable carrier or diluent and a therapeutically effective amount of a compound according to claim 6, or a pharmaceutically acceptable acid or base addition salt thereof, where possible.

13. A pharmaceutical composition comprising a pharmaceutically acceptable carrier or diluent and a therapeutically effective amount of a compound according to claim 7, or a pharmaceutically acceptable acid or base addition salt thereof, where possible.

14. A pharmaceutical composition comprising a pharmaceutically acceptable carrier or diluent and a therapeutically effective amount of a compound according to claim 8, or a pharmaceutically acceptable acid or base addition salt thereof, where possible.

15. A pharmaceutical composition comprising a pharmaceutically acceptable carrier or diluent and a therapeutically effective amount of a compound according to claim 9, or a pharmaceutically acceptable acid or base addition salt thereof, where possible.

16. A pharmaceutical composition comprising a pharmaceutically acceptable carrier or diluent and a therapeutically effective amount of a compound according to claim 10, or a pharmaceutically acceptable acid or base addition salt thereof, where possible.

* * * * *